US012213979B2

(12) United States Patent
Joseph et al.

(10) Patent No.: US 12,213,979 B2
(45) Date of Patent: Feb. 4, 2025

(54) BIOMARKERS OF METHOTREXATE-INDUCED IMMUNE TOLERANCE

(71) Applicant: Genzyme Corporation, Cambridge, MA (US)

(72) Inventors: Alexandra Joseph, Lexington, MA (US); Johnson Tran, Sacramento, CA (US); Susan M. Richards, Sudbury, MA (US)

(73) Assignee: Genzyme Corporation, Cambridge, MA (US)

( * ) Notice: Subject to any disclaimer, the term of this patent is extended or adjusted under 35 U.S.C. 154(b) by 1179 days.

(21) Appl. No.: 16/955,391

(22) PCT Filed: Dec. 21, 2018

(86) PCT No.: PCT/US2018/067098
§ 371 (c)(1),
(2) Date: Jun. 18, 2020

(87) PCT Pub. No.: WO2019/126647
PCT Pub. Date: Jun. 27, 2019

(65) Prior Publication Data
US 2021/0008074 A1 Jan. 14, 2021

Related U.S. Application Data

(60) Provisional application No. 62/609,986, filed on Dec. 22, 2017.

(51) Int. Cl.
*A61K 31/519* (2006.01)
*A61K 9/00* (2006.01)
*A61K 31/365* (2006.01)
*A61K 31/52* (2006.01)
*A61K 31/675* (2006.01)
*A61K 31/69* (2006.01)
*A61K 38/13* (2006.01)
*A61K 38/47* (2006.01)
*A61K 39/395* (2006.01)
*A61P 3/00* (2006.01)
*C12Q 1/6883* (2018.01)
*G01N 33/68* (2006.01)
*A61K 39/00* (2006.01)

(52) U.S. Cl.
CPC .......... *A61K 31/519* (2013.01); *A61K 9/0019* (2013.01); *A61K 31/365* (2013.01); *A61K 31/52* (2013.01); *A61K 31/675* (2013.01); *A61K 31/69* (2013.01); *A61K 38/13* (2013.01); *A61K 38/47* (2013.01); *A61K 39/395* (2013.01); *A61K 39/3955* (2013.01); *A61P 3/00* (2018.01); *C12Q 1/6883* (2013.01); *C12Y 302/0102* (2013.01); *C12Y 302/01022* (2013.01); *G01N 33/6893* (2013.01); *A61K 2039/54* (2013.01); *A61K 2039/545* (2013.01); *C12Q 2600/158* (2013.01); *G01N 2800/38* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,016,043 | A | 4/1977 | Schuurs |
| 4,018,653 | A | 4/1977 | Mennen |
| 4,275,149 | A | 6/1981 | Litman |
| 4,318,980 | A | 3/1982 | Boguslaski |
| 4,424,279 | A | 1/1984 | Bohn |
| 4,737,456 | A | 4/1988 | Weng |
| 7,001,994 | B2 | 2/2006 | Zhu |
| 7,723,296 | B2 | 5/2010 | Zhu |
| 7,786,277 | B2 | 8/2010 | Zhu |
| 8,399,657 | B2 | 3/2013 | Zhu |
| 8,759,501 | B2 | 6/2014 | Zhu |
| 8,841,427 | B2 | 9/2014 | Zhu |
| 9,469,850 | B2 | 10/2016 | Zhu |
| 9,687,531 | B2 | 6/2017 | Zhu |

(Continued)

FOREIGN PATENT DOCUMENTS

| | | | | |
|---|---|---|---|---|
| WO | WO-2012158362 A1 | * | 11/2012 | ........... A61K 31/519 |
| WO | 2019126647 A1 | | 6/2019 | |

OTHER PUBLICATIONS

Allman, D. et al. (Feb. 2004). "Alternative Routes To Maturity: Branch Points And Pathways For Generating Follicular And Marginal Zone B Cells," Immunol Rev 197(1): 147-160.

Banugaria, S.G. et al. (Jun. 25, 2013). "Algorithm For The Early Diagnosis And. Treatment Of Patients With Cross Reactive Immunologic Material-Negative Classic Infantile Pompe Disease: A Step Towards Improving The Efficacy Of ERT," PLoS One 8(6):e67052, 11 pages.

Burrow, T.A. et al. (Feb. 2015). "CNS, Lung, And Lymph Node Involvement In Gaucher Disease Type 3 After 11 Years Of Therapy: Clinical, Histopathologic, And Biochemical Findings," Molecular Genetics and Metabolism 114(2):233-241, 22 pages.

(Continued)

*Primary Examiner* — Sharon X Wen
(74) *Attorney, Agent, or Firm* — MORRISON & FOERSTER LLP

(57) ABSTRACT

The present application provides methods of treating a disease, such as Pompe disease, in a subject, comprising detecting an erythropoiesis biomarker in a sample of the subject after administration of methotrexate and a therapeutic agent to the subject, and administering further treatment with or without concurrently administering additional immune tolerance induction or immunosuppression therapy based on the level of the erythropoiesis biomarker. Further provided by the present application are methods and kits for assessing the level of immune tolerance to a therapeutic agent in a subject based on detection of an erythropoiesis biomarker after administration of methotrexate and the therapeutic agent to the subject.

18 Claims, 27 Drawing Sheets

(56) References Cited

U.S. PATENT DOCUMENTS

| | | | | |
|---|---|---|---|---|
| 11,672,802 | B2* | 6/2023 | Joseph | A61P 37/06 514/249 |
| 2014/0135337 | A1 | 5/2014 | Joseph | |

OTHER PUBLICATIONS

Chen, K. et al. (Oct. 13, 2009). "Resolving The Distinct Stages In Erythroid Differenhation Based On Dynamic Changes In Membrane Protein Expression During Erythropoiesis," Proc Natl Acad Sci USA 106(41):17413-17418.

Collins, P.W. et al. (May 2009). "Rituximab And Immune Tolerance In Severe Hemophilia A: A Consecutive National Cohort," Journal of Thrombosis and Haemostasis 7(5): 787-794.

Cremel et al. (Feb. 25, 2013, e-pub. Jan. 7, 2013). "Red Blood Cells as Innovative Antigen Carrier to Induce Specific Immune Tolerance," Int J Pharm.443(1-2):39-49.

Cremel, M., et al. (Aug. 2015, e-pub. Jun. 6, 2015). "Innovative Approach In Pompe Disease Therapy: Induction Of Immune Tolerance By Antigen-Encapsulated Red Blood Cells," International Journal of Pharmaceutics 491(1-2):69-77.

Cronstein, B.N. (Jun. 2005). "Low-Dose Methotrexate: A Mainstay In The Treatment Of Rheumatoid Arthritis," Pharmacological Reviews 57(2):163-172.

Daugas, E. et al. (Dec. 6, 2001). "Erythrocytes: Death Of A Mummy," Cell Death & Differentiation 8(12):1131-1133.

Dong, H. et al. (May 2011). "CD71 Is Selectively And Ubiquitously Expressed At High Levels In Erythroid Precursors Of All Maturation Stages: A Comparative Immunochemical Study With Glycophorin A And Hemoglobin A," The American Journal Of Surgical Pathology 35(5):723-732.

Dormer, P. et al. (Apr. 1982). "Differential Effect Of High-Dose Methotrexate On Erythropoiesis And Granulocytopoiesis In Humans," Cancer Res. 42(4):1604-1607.

Elahi, S. et al. (Dec. 5, 2013, e-pub Nov. 6, 2013). "Immunosuppressive CD71+ Erythroid Cells Compromise Neonatal Host Defence Against Infection," Nature 504(7478):158-162.

Ernst, P.B. et al. (Aug. 15, 2010). "Much Ado About Adenosine: Adenosine Synthesis And Function In Regulatory T Cell Biology," The Journal of Immunology 185(4):1993-1998.

Franchini, M. et al. (2008). "Immune Tolerance With Rituximab In Congenital Haemophilia With Inhibitors: A Systematic Literature Review Based On Individual Patients' Analysis," Haemophilia 14(5):903-912.

Garman, R.D. et al. (2004). "Methotrexate Reduces Antibody Responses To Recombinant Human α-Galactosidase A Therapy In A Mouse Model Of Fabry Disease," Clin. Exp. Immunol. 137(3):496-502.

Getts, D.R. et al. (Dec. 2013). "Exploiting Apoptosis For Therapeutic Tolerance Induction," The Journal of Immunology 191(11):5341-5346.

Grimm, A.J. et al. (Oct. 29, 2015). "Memory Of Tolerance And Induction Of Regulatory T Cells By Erythrocyte-Targeted Antigens," Scientific Reports: 15907, 11 pages.

Han, K.L. et al. (Jan. 2013, e-pub Dec. 7, 2012). "Adenosine A2A Receptor Agonist-Mediated Increase In Donor-Derived Regulatory T Cells Suppresses Development Of Graft-Versus-Host Disease." The Journal of Immunology 190(1):458-468.

International Preliminary Examination Report Issued on Jun. 23, 2020 for International Application No. PCT/US2018/067098 filed on Dec. 21, 2018, nine pages.

International Search Report and Written Opinion of the International Searching Authority mailed Apr. 4, 2019, for PCT Patent Application No. PCT/US2018/067098, filed Dec. 21, 2018, 17 pages.

Joly, M.S. et al. (Oct. 14, 2014). "Transient Low-Dose Methotrexate Generates B Regulatory Cells That Mediate Antigen-Specific Tolerance To Alglucosidase Alfa," The Journal of Immunology 193(8):3947-3958.

Joseph, A. et al. (2008). "Immune Tolerance Induction To Enzyme-Replacement Therapy By Co-Administration Of Short-Term, Low-Dose Methotrexate In A Murine Pompe Disease Model," Clin. Exp. Immunol. 152(1):138-146.

Joseph, A. et al. (Jul. 15, 2012, e-pub Jun. 18, 2012). "Transient Low-Dose Methotrexate Induces Tolerance To Murine Anti-Thymocyte Globulin And Together They Promote Long-Term Allograft Survival," The Journal of Immunology 189(2):732-743.

Kazi, Z.B. et al. (Feb. 1, 2016). "Prophylactic Immune Modulation In Infantile [Rho]Ompe Disease Using Low-Dose Methotrexate Induction: A Safe, Inexpensive, Widely Accessible, And Efficacious Strategy", Molecular Genetics and Metabolism 117(2): S65-S66.

Kazi, Z.B. et al. (Apr. 2019). "An Immune Tolerance Approach Using Transient Low-Dose Methotrexate In The ERT-Naïve Setting Of Patients Treated With A Therapeutic Protein: Experience In Infantile-Onset Pompe Disease," Genetics in Medicine 21(4):887-895.

Kina, T. et al. (May 2000). "The Monoclonal Antibody TER-119 Recognizes A Molecule Associated With Glycophorin A And Specifically Marks The Late Stages Of Murine Erythroid Lineage," British Journal Of Haematology 109(2):280-287.

Kishnani, P.S. et al. (Jan. 9, 2007). "Recombinant Human Acid A-Glucosidase: Major Clinical Benefits In Infantile-Onset Pompe Disease," Neurology 68(2):99-109.

Kontos, S. et al. (Jan. 2, 2013). "Engineering Antigens For In Situ Erythrocyte Binding Induces T-Cell Deletion," Proceedings of the National Academy of Sciences 110(1):E60-E68.

Koulnis, M. et al. (Aug. 5, 2011). "Identification And Analysis Of Mouse Erythroid Progenitors Using The CD71/TER119 Flow-Cytometric Assay," JoVE (Journal of Visualized Experiments) 54:e2809, 6 pages.

Kremer, J. M. (May 2004). "Toward A Better Understanding Of Methotrexate," Arthritis Rheum 50(5): 1370-1382.

Lorentz, K.M. et al. (Jul. 17, 2015). "Engineered Binding To Erythrocytes Induces Immunological Tolerance To *E. coli* Asparaginase," Science Advances 1(6):e1500112, 10 pages.

Mendelsohn, N. et al. (Jan. 8, 2009). "Elimination of Antibodies to Recombinant Enzyme in Pompe's Disease", NEJM 360(2):194-195.

Messinger, Y.H. et al. (Jan. 2012). "Successful Immune Tolerance Induction To Enzyme Replacement Therapy In CRIM-Negative Infantile Pompe Disease," Genet Med 14(1):135-142.

Nandakumar, S.K. et al. (Apr. 2016, e-pub. Feb. 5, 2016). "Advances In Understanding Erythropoiesis: Evolving Perspectives," British Journal Of Haematology 173(2):206-218.

Pan, B. T. et al. (Jul. 1983). "Fate Of The Transferrin Receptor During Maturation Of Sheep Reticulocytes In Vitro: Selective Externalization Of The Receptor," Cell 33(3):967-978.

Raposo, C.J. et al (Apr. 4, 2022). "Engineered RBCs Encapsulating Antigen Induce Multi-Modal Antigen-Specific Tolerance and Protect Against Type 1 Diabetes," Frontiers in Immunology 13(869669):1-17.

Schäkel, K. et al. (Jun. 1, 2006). "Human 6-Sulfo Lacnac-Expressing Dendritic Cells Are Principal Producers Of Early Interleukin-12 And Are Controlled By Erythrocytes," Immunity 24(6):767-777.

Taylor, W.J. et al. (Jul. 1, 2008). "Drug Use And Toxicity In Psoriatic Disease: Focus On Methotrexate," The Journal of Rheumatology 35(7):1454-1457.

Testa, U. (2004). "Apoptotic Mechanisms In The Control Of Erythropoiesis," Leukemia 18(7):1176-1199.

Tran, J.Q. et al. (2020). "Expansion Of Immature, Nucleated Red Blood Cells By Transient Low-Dose Methotrexate Immune Tolerance Induction In Mice," British Society for Immunology, Clinical and Experimental Immunology 203:409-423.

Van Putten, L. M. (1958). "The Life Span Of Red Cells In The Rat And The Mouse As Determined By Labeling With DFP32 In Vivo." Blood 13(8): 789-794.

Yi, T. et al. (Oct. 20, 2015). "Splenic Dendritic Cells Survey Red Blood Cells for Missing Self-CD47 to Trigger Adaptive Immune Responses." Immunity 43(4): 764-775, 23 pages.

(56) References Cited

OTHER PUBLICATIONS

Kavitha, C. et al. (Sep. 1, 2017). "Low-Dose Methotrexate In Myeloproliferative Neoplasm Models," Haematologica 102(9):e336-e339.

* cited by examiner

BIOMARKERS OF METHOTREXATE-INDUCED IMMUNE TOLERANCE

CROSS-REFERENCE TO RELATED APPLICATIONS

This application is a National Phase application under 35 U.S.C. § 371 of International Application No. PCT/US2018/067098, filed Dec. 21, 2018, which claims the priority benefit of U.S. Provisional Application No. 62/609,986, filed Dec. 22, 2017, the disclosure of each of which is hereby incorporated by reference in its entirety.

FIELD OF THE INVENTION

The present invention relates generally to immunology, and more specifically to methods of treating a subject with a therapeutic agent and assessing immune tolerance to the therapeutic agent induced by methotrexate based on detection of erythropoiesis biomarkers.

BACKGROUND OF THE INVENTION

Methotrexate has an established history in the treatment of malignant and autoimmune diseases (See, e.g., Kremer 2004). It was first described for the treatment of cancer during the 1940's, and high-dose courses of methotrexate continue to be used to treat a number of neoplastic conditions. In autoimmunity, continuous weekly low-dose methotrexate is used to treat diseases such as rheumatoid arthritis and psoriasis, among others (reviewed in Cronstein 2005; Taylor et. al. 2008). More recent studies, however, have uncovered an alternative use of methotrexate inducing immune tolerance. A transient low-dose methotrexate immune tolerance induction (ITI) regimen has been shown to induce immune tolerance to enzyme replacement therapies (ERTs), such as recombinant human acid-α-glucosidase (rhGAA, alglucosidase alfa) (Garman, Munroe et. al. 2004; Joseph, Munroe et. al. 2008). Concurrent administration of transient low-dose methotrexate treatment and a therapeutic biologic has also been shown to induce long-term immune tolerance to the biologic, as demonstrated with murine anti-thymocyte globulin used to treat transplant rejection in allogeneic cardiac transplantation (Joseph, Neff et. al. 2012). In clinical observations in high-risk, classic infantile-onset Pompe patients, an immune tolerance protocol in which transient low-dose methotrexate co-administered with Rituximab (monoclonal antibody that depletes B cells) and, optionally, intravenous immunoglobulin (IVIG), has been successful in providing lasting reduction of anti-drug antibodies (ADA) to rhGAA (Mendelsohn, Messinger et. al. 2009, Messinger, Mendelsohn et. al. 2012, Banugaria, Prater et. al. 2013). As Rituximab alone has generally not been able to reproducible induce long-lived immune tolerance, methotrexate is thought to contribute to successful immune tolerance in the clinical regimen (Franchini, Mengoli et. al. 2008, Collins, Mathias et. al. 2009).

Pompe disease is caused by a deficiency of the lysosomal acid α-glucosidase (GAA) gene. High-risk, classic infantile-onset Pompe patients lack endogenous GAA, an enzyme that breaks down glycogen in the lysosome. Lack of functional GAA results in neuromuscular pathology that arises from an over-accumulation of glycogen in muscle tissue. Without treatment, disease progression in these patients is rapid, with muscle deterioration (myopathy) that leads to respiratory weakness ultimately requiring invasive ventilation, heart failure, and death generally within the first year of life. Enzyme-replacement therapy with rhGAA has been effective in treating Pompe disease (Kishnani, Corzo et. al. 2007). However, rhGAA monotherapy in high-risk, classic infantile-onset Pompe patients typically leads to high titers of ADA against rhGAA that interfere with treatment reduce efficacy. To date, long-term immune tolerance to rhGAA. has been successfully induced in clinical studies in a handful of classical infantile-onset Pompe patients by co-administration of transient low-dose methotrexate with Rituximab and IVIG. In these studies, patients have continued to be ADA-free for more than 35 months of age with ongoing treatment (Mendelsohn, Messinger et. al. 2009; Messinger, Mendelsohn et. al. 2012; Banugaria, Prater et. al. 2013). However, the extent of immune modulation required to mitigate the ADA responses varied amongst the patients with the extent of prior enzyme replacement therapy: patients who previously received ERT prior to immune tolerance treatment required further immune modulation (Messinger, Mendelsohn et. al. 2012). Though clinical observations remain limited in number, it is clear that successful ERT in high-risk, infantile-onset Pompe patients is more likely to be successful the earlier in ERT that immune tolerance is achieved, so as to limit the development and potential entrenchment of ADA immune response to rhGAA (Banugaria, Prater et. al. 2013). However, the tools available for monitoring immune tolerance to guide immunomodulatory therapy can be of limited utility in these patients: anti-drug antibodies are the primary markers of the extent (or lack) of tolerance, but such antibodies typically do not appear for weeks to months after treatment with a therapeutic biologic commences. At this point, critical time may have already been lost for effectively inducing and maintaining immune tolerance. The absence of markers of immune tolerance that arise earlier in therapy is of particular concern for patients such as high risk, infantile-onset Pompe patients, who rapidly deteriorate in the absence of effective therapy.

Accordingly, there is a need for improved methods of assessing immune tolerance (such as early induction of immune tolerance) to guide strategies for reducing undesirable immune response in patients receiving therapeutics capable of provoking immune responses, including therapeutic biologics such as rhGAA for Pompe disease.

The disclosures of all publications, patents, patent applications and published patent applications referred to herein are hereby incorporated herein by reference in their entirety.

BRIEF SUMMARY OF THE INVENTION

The present invention provides methods of treatment and methods of assessing the level of immune tolerance to a therapeutic agent based on detection of an erythropoiesis biomarker.

Accordingly, one aspect of the present application provides a method for treating a subject in need of treatment with a -therapeutic agent, comprising: (a) administering to the subject an effective amount of methotrexate; (b) administering to the subject an effective amount of the therapeutic agent; (c) detecting an erythropoiesis biomarker in a sample obtained from the subject between at least one day and about 30 days after administration of methotrexate; and d) continuing further treatment with the therapeutic agent with or without administering additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, wherein if the level of the erythropoiesis biomarker is approximately equal to or less than that of a control, step (d) comprises administering the additional immune tolerance induction therapy or the immunosuppression therapy concurrently with further treatment with the therapeutic agent; or wherein if the level of the erythropoiesis biomarker is elevated with respect to that of a control, step (d) comprises continuing further treatment with the therapeutic agent without administering the additional immune tolerance induction therapy or the immunosuppression therapy. In some embodiments, wherein if the level of the erythropoiesis biomarker is approximately elevated with respect to that of a control, step (d) comprises administering the additional immune tolerance induction therapy or the immunosuppression therapy concurrently with further treatment with the therapeutic agent: or wherein if the level of the erythropoiesis biomarker is equal to or less than that of a control, step (d) comprises continuing further treatment with the therapeutic agent without administering the additional immune tolerance induction therapy or the immunosuppression therapy In some embodiments, there is provided a method for treating a subject in need of treatment with a therapeutic agent, comprising (a) administering to the subject an effective amount of methotrexate; (b) administering to the subject an effective amount of the therapeutic agent; c) detecting an erythropoiesis biomarker in a sample obtained from the subject between at least one day and about 30 days after administration of methotrexate; (d) if the level of the erythropoiesis biomarker is approximately equal to or less titan that of a control, administering the additional immune tolerance induction therapy or the immunosuppression therapy concurrently with further treatment with the therapeutic agent; or (e) if the level of the erythropoiesis biomarker is elevated with respect to that of a control, continuing further treatment with the therapeutic agent without administering the additional immune tolerance induction therapy or the immunosuppression therapy. In some embodiments, the erythropoiesis biomarker is the level of immature nucleated red blood cells, immature reticulocyte fraction, or cellular nucleic acid contents. In some embodiments, if the level of immature nucleated red blood cells initially decreases before the level of immature nucleated red blood cells is elevated, further treatment with the therapeutic agent is continued without administering the additional immune tolerance induction therapy or the immunosuppression therapy In some embodiments, wherein the methotrexate is administered in a single cycle, wherein the level of immature nucleated red blood cells decreases by about one, about two, about three, about four, about five, about six, or about seven days before the level of immature nucleated red blood cells becomes elevated. In some embodiments, wherein the methotrexate is administered in two or more cycles, wherein the level of immature nucleated red blood cells decreases by about one to about 14 days before the level of immature nucleated red blood cells becomes elevated in some embodiments, wherein the methotrexate is administered in two, three, four, five or more cycles, wherein the level of immature nucleated red blood cells decreases by about one to about 14 days before the level of immature nucleated red blood cells becomes elevated.

In some embodiments, there is provided a method for treating a subject in need of treatment with a therapeutic agent, comprising: (a) administering to the subject an effective amount of methotrexate; (b) administering to the subject an effective amount of the therapeutic agent; (c) detecting an erythropoiesis biomarker in a sample obtained from the subject between at least one day and about 30 days after administration of methotrexate; (d) if the level of the erythropoiesis biomarker is approximately elevated with respect to that of a control, administering additional immune tolerance induction therapy or immunosuppression therapy concurrently with further treatment with the therapeutic agent; or (e) if the level of the erythropoiesis biomarker is equal to or less than that of a control, continuing further treatment with the therapeutic agent without administering additional immune tolerance induction therapy or immunosuppression therapy. In some embodiments, the erythropoiesis biomarker is hematocrit.

In some embodiments according to any one of the methods described above, the detecting the erythropoiesis biomarker is detecting the expression of a gene associated with erythropoiesis, wherein the gene associated with erythropoiesis is one or more of hemopoiesis, iron ion homeostasis, regulation of erythrocyte differentiation, and heme metabolism. In some embodiments, the gene associated with erythropoiesis is a gene encoding transferrin receptor, transferrin, Ly76 (antigen for Ter-119), CD44, CD235a, ALAS2, or GATA-1. In some embodiments, the transferrin receptor is transferrin receptor 1 (CD71). In some embodiments, detecting the gene associated with erythropoiesis comprises detecting an RNA transcript of the gene associated with erythropoiesis or detecting a protein product of the gene associated with erythropoiesis. In some embodiments, the protein product is hemoglobin.

In some embodiments according to any one of the methods described above, the erythropoiesis biomarker is a co-factor associated with erythropoiesis. In some embodiments, the co-factor associated with erythropoiesis is porphyrin, a porphyrin-containing compound, or a tetrapyrrole.

In some embodiments according to any one of the methods described above, the therapeutic agent is a polypeptide, a nucleic acid, a virus, a gene therapy, a lipid, a liposome, or a carbohydrate. In some embodiments, the therapeutic agent is a therapeutic polypeptide. In some embodiments, the therapeutic polypeptide is an antibody or antigen-binding fragment thereof. In some embodiments, the antibody is a monoclonal antibody. In some embodiments, the antibody is a. lymphocyte-depleting agent. In some embodiments, the antibody is alemtuzumab. In some embodiments, the therapeutic polypeptide is an enzyme. In some embodiments, the enzyme is human alpha galactosidase A. In some embodiments, the enzyme is human acid α-glucosidase.

In some embodiments according, to any one of the methods described above, the subject has a lysosomal storage disease. In some embodiments, the subject has Pompe disease. In some embodiments, the subject has infantile-onset Pompe disease, such as classic infantile-onset Pompe disease. In some embodiments, the Pompe disease is cross reactive immunological material (CRIM)-negative. In. some embodiments, the method further comprises administering an initial immune tolerance induction therapy concurrently with administration of the therapeutic agent, wherein the therapeutic agent is human acid α-glucosidase. In some embodiments, the initial immune tolerance induction therapy comprises administering one or more of rituximab and IVIG In some embodiments, there is provided a method of treating Pompe disease in a subject (e.g., human.) in need thereof, comprising: (a) administering to the subject an effective amount of methotrexate; (b) administering to the subject an effective amount of human acid α-glucosidase; (c) detecting an erythropoiesis biomarker in a sample obtained from the subject at least one day to about 30 days after administration of methotrexate; (d) if the level of the erythropoiesis biomarker is approximately equal to or less than that of a control, administering additional immune tolerance induction therapy or immunosuppression therapy concurrently with further treatment with the human acid α-glucosidase; or (e) if the level of the erythropoiesis biomarker is elevated with respect to that of a control, continuing further treatment with the human acid α-glucosidase without administering additional immune tolerance induction therapy or immunosuppression therapy. In some embodiments, the erythropoiesis biomarker is the level of immature nucleated red blood cells, immature reticulocyte fraction, or cellular nucleic acid contents. In some embodiments, if the level of immature nucleated red blood cells initially decreases before the level of immature nucleated red blood cells is elevated, further treatment with the therapeutic agent is continued without administering the additional immune tolerance induction therapy or the immunosuppression therapy. In some embodiments, wherein the methotrexate is administered in a single cycle, wherein the level of immature nucleated red blood cells decreases by about one, about two, about three, about four, about five, about six, or about seven days before the level of immature nucleated red blood cells becomes elevated. In some embodiments, wherein the methotrexate is administered in two or more cycles, wherein the level of immature nucleated red blood cells decreases by about one to about 14 days before the level of immature nucleated red blood cells becomes elevated. In some embodiments, wherein the methotrexate is administered in two, three, four, five or more cycles, wherein the level of immature nucleated red blood cells decreases by about one to about 14 days before the level of immature nucleated red blood cells becomes elevated.

In some embodiments, there is provided a method of treating Pompe disease in a subject (e.g, human) in need thereof, comprising: (a) administering to the subject an effective amount of methotrexate: (b) administering to the subject an effective amount of human acid α-glucosidase; (c) detecting an erythropoiesis biomarker in a sample obtained from the subject at least one day to about 30 days after administration of methotrexate; (d) if the level of the erythropoiesis biomarker is approximately elevated with respect to that of a control, administering additional immune tolerance induction therapy or immunosuppression therapy concurrently with further treatment with die human acid α-glucosidase; or (e) if the level of the erythropoiesis biomarker is equal to or less than that of a control, continuing further treatment with the human acid α-glucosidase without administering additional immune tolerance induction therapy or immunosuppression therapy. In some embodiments, the erythropoiesis biomarker is hematocrit. In some embodiments, detecting the erythropoiesis biomarker is detecting the expression of a gene associated with erythropoiesis, wherein the gene associated with erythropoiesis is a gene associated with one or more of hemopoiesis, iron ion homeostasis, regulation of erythrocyte differentiation, and hem metabolism. In some embodiments, detecting the gene associated with erythropoiesis comprises detecting an RNA transcript of the gene associated with erythropoiesis or detecting a protein product of the gene associated with erythropoiesis. In some embodiments, the protein product is hemoglobin.

In some embodiments, there is provided a method of treating Pompe disease in a subject (e. g , human) in need thereof, comprising: (a) administering to the subject an effective amount of methotrexate; (b) administering to the subject an effective amount of human acid α-glucosidase; (c) detecting an erythropoiesis biomarker in a sample obtained from the subject at least one day to about 30 days after administration of methotrexate; (d) if the level of the erythropoiesis biomarker is approximately equal to or less than that of a control, administering additional immune tolerance induction therapy or immunosuppression therapy concurrently with further treatment with the human acid α-glucosidase; or (e) if the level of the erythropoiesis biomarker is elevated with respect to that of a control, continuing further treatment with the human acid α-glucosidase without administering additional immune tolerance induction therapy or immunosuppression therapy. In some embodiments, detecting the erythropoiesis biomarker is detecting the expression of a gene associated with erythropoiesis, wherein the gene associated with erythropoiesis is a gene associated with one or more of hemopoiesis, iron ion homeostasis, regulation of erythrocyte differentiation, and heme metabolism. In some embodiments, the gene associated with erythropoiesis is a gene encoding transferrin receptor, transferrin, Ly76 (antigen for Ter-119), CD-44, CD235a, ALAS2, or GATA-1. In some embodiments, the transferrin receptor is transferrin receptor 1 (CD71). In some embodiments, detecting the gene associated with erythropoiesis comprises detecting an RNA transcript of the gene associated with erythropoiesis or detecting a protein product of the gene associated with erythropoiesis. In some embodiments, the erythropoiesis biomarker is a co-factor associated with erythropoiesis. In some embodiments, the co-factor associated with erythropoiesis is porphyrin, a porphyrin-containing compound, or a tetrapyrrole.

In some embodiments according to any one of the methods of treating Pompe disease described above, the Pompe disease is infantile-onset Pompe disease. In some embodiments, the Pompe disease is classic infantile-onset Pompe disease. In some embodiments, the subject is CRIM-negative.

In some embodiments according to any one of the methods of treating Pompe disease, the method further comprises monitoring one or more of anti-human acid α-glucosidase antibody, CD19 levels, or disease progression.

In some embodiments according to any one of the methods described above, the sample is a blood sample. In some embodiments, the blood sample is a blood fraction comprising peripheral blood mononuclear cells (PBMC). In some embodiments, the Hood sample is a serum sample or a plasma sample and detecting the biomarker is detecting the expression of a gene associated with erythropoiesis.

In some embodiments according to any one of the methods described above, the control is a historical control or a placebo control.

In some embodiments according to any one of the methods described above, the subject is human.

In some embodiments according to any one of the methods described above, the effective amount of methotrexate is administered in a single cycle or in three cycles. In some embodiments, the methotrexate is administered in a single cycle. In some embodiments, the methotrexate is administered in a two, three, four, five or more cycles, in some embodiments, a cycle of methotrexate consists of 1 day of methotrexate administration or 2, 3, 4, 5, 6, 7, 8, 9, 10, or 11 consecutive days of methotrexate administration.

In some embodiments according to any one of the methods described above, the methotrexate is administered to the subject at a time selected from one or more of before, during, and after administration of the therapeutic agent. In some embodiments, the methotrexate is administered between 48 hours prior to and 48 hours after the administration of the therapeutic agent treatment. In some embodiments, the methotrexate is administered concurrently with administration of the therapeutic agent and about 24 and about 48 hours after administration of the therapeutic agent.

In some embodiments according to any one of the methods described above, the methotrexate is administered at about 0.1 mg/kg to about 5 mg/kg.

In some embodiments according to any one of the methods described above, the sample is obtained from the subject at least about one day to about 30 days following the last administration. of the methotrexate. In some embodiments, the sample is obtained from the subject at about 7 days to about 14 days following the last administration of the methotrexate. In some embodiments, samples are obtained on a plurality of days following the last administration of the methotrexate. In some embodiments, a sample is obtained on one or more of day 1, day 2, day 3, day 4 day 5, day 6, day 7, day 14, day 21, or day 28 following the last administration of the methotrexate, In some embodiments according to any one of the methods described above, step (d) further comprises administering an agent that depletes T-cells, B-cells, or plasma cells. In some embodiments, the agent that depletes plasma cells is bortezomib. In some embodiments, step (d) comprises one or more of: (a) administering an effective amount of one or more of rituximab, intravenous immunoglobulin (IVIG), cyclophosphamide, bortezomib, azathioprine, cyclosporine, mycophenolate, and a corticosteroid and (b) administering an antigen-specific tolerance strategy. In some embodiments, the antigen-specific tolerance strategy comprises administering more frequent doses of the therapeutic agent or a higher dose of the therapeutic agent or both. In some embodiments, a higher dose of the therapeutic agent is administered concomitantly with IVIG.

One aspect of the present application provides a method of assessing the level of immune tolerance in a subject with Pompe disease, comprising: (a) obtaining a sample from the subject, wherein the subject has previously been administered at least one cycle of methotrexate treatment and at least one dose of the therapeutic agent and (b) detecting an erythropoiesis biomarker in the sample, wherein the level of the erythropoiesis biomarker in the sample with respect to the level of a control indicates an induction of immune tolerance. In some embodiments, step (b) comprises contacting the sample with an agent that binds to an erythropoiesis biomarker.

One aspect of the present application provides a method of assessing the level of immune tolerance to a therapeutic agent in a subject in need of the therapeutic agent, comprising: (a) administering to the subject an effective amount of methotrexate; (b) administering to the subject an effective amount of the therapeutic agent; and (c) detecting an erythropoiesis biomarker in a sample obtained from the subject, wherein. a level of the erythropoiesis biomarker in the sample with respect to the level of a control indicates induction of immune tolerance in the subject to the therapeutic agent.

One aspect of the present application. provides a method of assessing the level of immune tolerance to a therapeutic agent in a subject m need of the therapeutic agent, comprising: (a) administering to the subject an of amount of methotrexate; (b) administering to the subject an effective amount of the therapeutic agent; (c) detecting an erythropoiesis biomarker in a sample obtained from the subject at least one day to about 30 days after administration of methotrexate; and (d) identifying the .level of immune tolerance to the therapeutic agent in the subject based on the level of the biomarker detected in step c).

In some embodiments according to any one of the methods of assessing described above, a change in the level of the erythropoiesis biomarker is associated with induction of erythropoiesis. in some embodiments, if the level of the erythropoiesis biomarker is approximately equal to or less than that of a control, the subject is in need of additional immune tolerance induction therapy or immunosuppression therapy concurrently with further treatment with the therapeutic agent; or if the level of the erythropoiesis biomarker is elevated with respect to that of a control, the subject is not in need of additional immune tolerance induction therapy or immunosuppression therapy. In some embodiments, if the level of the erythropoiesis biomarker is approximately elevated with respect to that of a control, the subject is in need of additional immune tolerance induction therapy or immunosuppression therapy concurrently with further treatment with the therapeutic agent; or wherein if the level of the erythropoiesis biomarker is equal to or less than that of a control, the subject is not in need of additional immune tolerance induction therapy or immunosuppression therapy, Further provided are compositions, kits and articles of manufacture for use in any one of the methods described herein.

These and other aspects and advantages of the present invention will become apparent from the subsequent detailed description and the appended claims. It is to be understood that one, some, or all of the properties of the various embodiments described herein may be combined to form other embodiments of the present invention,

BRIEF DESCRIPTION OF THE DRAWINGS

from live Ter-119+ live events identified: (I) proerythroblasts (Ter-119$^{intermediate}$, CD44$^{high}$), (II) basophilic erythroblasts (Ter-119+, CD44$^{high}$), (III) polychromatic erythroblasts (Ter-119+, CD44$^{intermediate}$FSC$^{intermediate}$), (IV) orthochromatic erythroblasts and reticulocytes (Ter-119+, CD44$^{intermediate}$FSC$^{low}$), and (V) mature red blood cells (Ter-119+, CD44$^{low}$FSC$^{low}$). FIG. 5D shows the numbers of erythroid cells in bloods samples of mice on day 2 after rhGAA initiation. FIG. 5E shows the numbers of erythroid cells in bloods samples of mice on day 7 after rhGAA initiation. Each blood sample was derived from a 25 µL collection from the systemic blood compartment. FIG. 5F shows the numbers of erythroid cells in bone marrow samples of mice on day 4 after rhGAA initiation. FIG. 5H shows the numbers of erythroid cells in bone marrow samples of mice on day 7 after rhGAA initiation.

(FIG. 11A) 200 million total erythrocytes from the blood of donor mice, 9 days after rhGAA initiation, were purified by leukoreduction. Donor erythrocytes purified from blood were ≥99.9% pure. (FIG. 11B) 75 million total erythrocytes from the spleen of donor mice, 7 days after rhGAA. initiation, were purified by positive selection with Ter-119 microbeads. Donor erythrocytes purified from spleen were ≥93.3% pure. (FIG. 11C Dosed control mice with rhGAA in the presence and absence of transient low-dose methotrexate ITI regimen. Highest titer value removed. This data is from a single experiment. Student t tests were performed and significance is noted as *≤0.05. Vertical bars represent standard error of the mean. AUC: area under curve.

DETAILED DESCRIPTION OF THE INVENTION

Figure 1A:
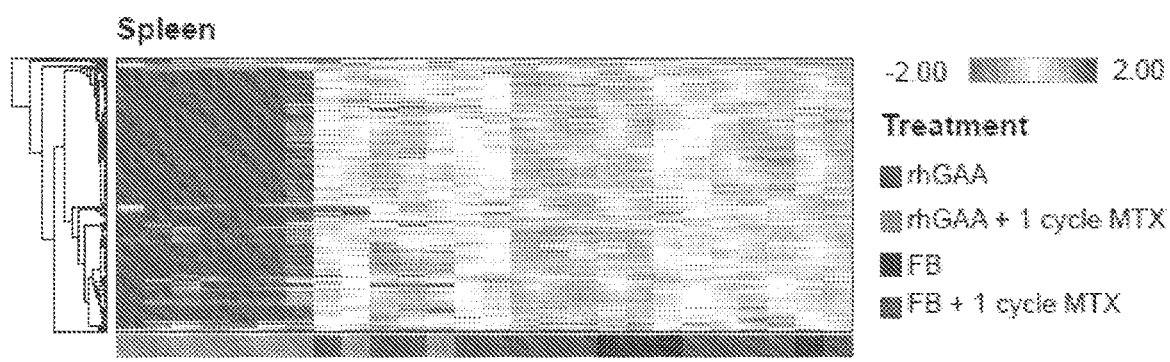
FIG. 1A shows a heat map of a subset of gene expression levels associated with erythropoiesis in spleen samples of Mice in various experimental groups.

The present application provides methods of treating a disease (such as Pompe disease) in a subject with a therapeutic agent and methods of assessing the level of immune tolerance to a therapeutic agent in a subject comprising detection of an erythropoiesis biomarker after administration of methotrexate and the therapeutic agent.

Anti-drug antibody (ADA) immune responses can reduce drug efficacy and negatively impact patient safety. To mitigate the accumulation of ADA, an immune tolerance induction ("ITI") regimen comprising transient low-dose methotrexate treatment has been developed for administration alongside and within the first week of a treatment with a therapeutic biologic (Garman, Munroe et. al. 2004; Joseph, Munroe et. al. 2008). Long-term immune tolerance to enzyme-replacement therapies (such as alglucosidase alfa) and antibody therapies such as anti-thymocyte globulin) were demonstrated with the transient low-dose methotrexate regimen (Id; Joseph, Neff et. al. 2012).

Aspects of the invention relate to the discovery that erythropoiesis triggered by transient low-dose methotrexate administration is associated with induction of immune tolerance. The methods and kits described herein are useful for reducing undesired immune responses in patients receiving therapeutics such as enzyme replacement therapies that generate anti-drug antibodies (ADA).

The present disclosure describes molecular and cellular responses in the spleen, blood, and bone marrow to transient low-dose methotrexate (an exemplary ITI regimen) in the context of treatment with a therapeutic biologic, i.e, recombinant human acid α-glucosidase (rhGAA, alglucosidase alfa) treatment, an enzyme-replacement therapy used to treat Pompe disease. Transcriptional and proteomic analyses described herein uncovered upregulation of transcriptional and protein signatures in blood and spleen indicative of erythropoiesis after treatment with transient lose dose methotrexate (an exemplary ITI regimen). Cellular studies confirmed a significant expansion of Ter-119$^+$CD71$^+$ immature, nucleated red blood cells (RBCs) in the spleen and blood upon transient low-dose methotrexate treatment. Moreover, immunofluorescence analysis suggested an increased proportion of nucleated cells, including hematopoietic precursors, in the splenic red. pulp. Conversely, tissue mass spectrometry imaging (tMSI) showed reduced detection of proteins related to mature RBCs in the spleen. Notably, the timing of expansion of these RBCs coincided with the significant enrichment of regulator, B cells, which have previously been demonstrated to have the capacity to confer immune tolerance in treatment-naive animals. Further analysis described. herein shows that transfusion of erythroid cells derived from animals treated with transient low-dose methotrexate conferred immune tolerance to the nave recipients. Thus, erythropoiesis biomarkers described herein can be used to assess immune tolerance to a therapeutic agent and/or to guide administration of additional immune tolerance induction or immunosuppression therapy in conjunction with further administration of the therapeutic agent in patients that have received methotrexate and the therapeutic agent.

Accordingly, one aspect of the present application provides a method for treating a subject in need of treatment with a therapeutic agent (such as a subject with Pompe disease in need of treatment with human acid α-glucosidase), comprising: (a) administering to the subject an effective amount of methotrexate, (b) administering to the subject an effective amount of the therapeutic agent; (c) detecting an erythropoiesis biomarker in a sample obtained from the subject between at least one day and about 30 days after administration of methotrexate; and (d) continuing further treatment with the therapeutic agent with or without administering additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, if the level of the erythropoiesis biomarker is approximately equal to or less than that of a control, step (d) comprises administering the additional immune tolerance induction therapy or the immunosuppression therapy concurrently with further treatment with the therapeutic agent; or if the level of the erythropoiesis biomarker is elevated with respect to that of a control, step (d) comprises continuing further treatment with the therapeutic agent without administering the additional immune tolerance induction therapy or the immunosuppression therapy. In some embodiments, if the level of the erythropoiesis biomarker is approximately elevated with respect to that of a control, step (d) comprises administering the additional immune tolerance induction therapy or the immunosuppression therapy concurrently with further treatment with the therapeutic agent; or if the level of the erythropoiesis biomarker is equal to or less than that of a control, step (d) comprises continuing further treatment with the therapeutic agent without administering the additional immune tolerance induction therapy or the immunosuppression therapy.

In another aspect of the present application, there is provided a method for assessing the level of immune tolerance to a therapeutic agent in a subject in need of the therapeutic agent (such as a subject with Pompe disease in need of treatment with human acid α-glucosidase), comprising: (a) administering to the subject an effective amount of methotrexate; (b) administering to the subject a therapeutically effective amount of the therapeutic agent; and (c) detecting an erythropoiesis biomarker in a sample obtained from the subject, wherein a level of the erythropoiesis biomarker the sample with respect to the level of a control indicates induction of immune tolerance in the subject to the therapeutic agent.

Also provided are kits and articles of manufacture useful for the methods described herein.

I. Definitions

The term "detecting" is used herein in the broadest sense to include both qualitative and quantitative measurements of a target molecule. Detecting includes identifying the mere presence of the target molecule in a sample as well as determining whether the target molecule is present in the sample at detectable levels.

The terms "polypeptide" and "protein" are used interchangeably herein to refer to polymers of amino acids of any length. The polymer may he linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc:), as well as other modifications known in the art. The terms "polypeptide" and "protein" as used herein specifically encompass antibodies. In some examples, a protein comprises multiple polypeptides or polymer chains.

The term "biomarker" as used herein refers to an indicator, e.g., predictive, diagnostic, and/or prognostic, which can be detected in a sample. The biomarker may serve as an indicator of a. particular subtype of a disease, condition, or biological response (e.g., undesired immune response to a therapeutic agent) characterized by certain, molecular, pathological, histological, and/or clinical features. In some embodiments, a biomarker is a gene. In some embodiments, a biomarker is a population or subset of cells. Biomarkers include, but are not limited to, polynucleotides (e. DNA, and/or RNA), polynucleotide copy number alterations (e.g., DNA copy numbers), polypeptides, polypeptide and polynucleotide modifications (e.g. posttranslational modifications), carbohydrates, glycolipid-based molecular markers, cells, and/or populations of cells, The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

The term "housekeeping biomarker" refers to a biomarker or group of biomarkers polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methylphosphonates, phosphotriesters, phosphoamidates, carbamates, etc.) and with charged linkages (e.g., phosphorothioate, phosphorodithioate, etc.), those containing pendant moieties, such as, for example, proteins (e.g., nucleases, toxins, antibodies, signal peptides, ply-L-lysine, etc.), those with intercalators acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may he replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may he synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and thereafter promotes polymerization of a complementary nucleic acid, generally by providing a free 3'—OH group.

The term "small molecule" refers to any molecule with a molecular weight of about 2000 Daltons or less, preferably of about 500 Daltons or less.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and. combinations thereof.

By "tissue sample" or "cell sample" is meant a collection of similar cells obtained from a tissue or compartment of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

"reference sample", "reference cell", "reference tissue", "control sample", "control cell", or "control tissue", as used herein, refers to a sample, cell, tissue, standard, or level that is used for comparison purposes.

For the purposes herein a "section" of a tissue sample is meant a single part or piece of a tissue sample, e.g a thin slice of tissue or cells cut from a tissue sample. it is understood that multiple sections of tissue samples may be taken and subjected to analysis, provided that it is understood that the same section of tissue sample may be analyzed at both morphological and. molecular levels, or analyzed with respect to both polypeptides and polynucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., $K_d$ values or expression). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between. two numeric -values such that one of skill in the art would consider the difference between the two -values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

An "effective amount" of an agent refers to an amount effective, at dosages and for periods of time necessary, to achieve the desired physiological result.

A "therapeutically effective amount" refers to an amount of a therapeutic agent to treat or prevent a disease or condition in a subject. In some embodiments, a therapeutically effective amount of the therapeutic agent may extend survival (including overall survival and progression free survival); result in an objective response (including a complete response or a partial response); relieve to at least in part one or more signs or symptoms of the disease or condition; and/or improve the quality of life of the subject.

The term "pharmaceutical composition" refers to a preparation which is in such form as to permit the biological activity of an active ingredient contained therein to be effective, and which contains no additional components which are unacceptably toxic to a subject to which the formulation would be administered, "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, As used herein, "treatment" (and grammatical variations thereof such as "treat" or "treating") refers to clinical intervention in an attempt to alter the natural course of the individual being treated, and can be performed during the course of clinical pathology. Desirable effects of treatment include, but are not limited to, preventing recurrence of disease, alleviation of symptoms, diminishment of any direct or indirect pathological consequences of the disease, decreasing the rate of disease progression, amelioration or palliation of the disease state, and remission or improved, prognosis.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., Mice and rats). In certain embodiments, the individual or subject is a human.

The term "concurrently" is used herein to refer to administration of two or more therapeutic agents, where at least part of the administration overlaps in time, or where administration does not strictly overlap in time but where one agent remains at a systemic level sufficient to continue to exert a physiological effect while at least a second agent is administered. Accordingly, concurrent administration includes a dosing regimen in which the administration of one or more agent(s) continues after discontinuing the administration of one or more other agent(s) or in which one or more agent(s) is administered after one or more other agent(s) have been administered but remain at systemic levels sufficient to continue to exert a physiological effect.

By "reduce or inhibit" is meant the ability to cause an overall decrease of about any of 5%, 10%, 20%, 30%, 40%, 50%, 60%, 70%, 75%, 80%, 85%, 90%, 95%, or greater.

By "increase or elevate" is meant the ability to cause an overall increase of about any of 5%, 10%, 20%, 30%, 40%, 50%, 50%, 70%, 75%, 80%, 85%, 90%, 95%, or greater.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or condition (e.g., cancer), or a probe for specifically detecting a biomarker described herein. In certain embodiments, the manufacture or kit is promoted, distributed, or sold as a unit for performing the methods described herein.

The phrase "based on" when used herein means that the information about one or more biomarkers is used to inform a treatment decision., information provided on a package insert, or marketing/promotional guidance, etc.

An antibody "which binds" an antigen of interest, e.g. a, host cell protein, is one that binds the antigen with sufficient affinity such that the antibody is useful as an assay reagent, e.g., as a capture antibody or as a detection antibody. Typically, such an antibody does not significantly cross-react with other polypeptides (e.g., oilier antigens).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a target molecule compared to binding of a control molecule, which generally is a molecule composed of similar structural elements that does not have binding activity (e.g., a control protein that is not identical to a target protein).

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic, binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "antibody" herein is used in the broadest sense and specifically covers monoclonal antibodies, polyclonal antibodies, half-antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and the include plural referents unless the context clearly dictates otherwise.

II. Methods of Treatment and Assessment

Provided herein are methods of treating a subject in need of treatment with a therapeutic agent based on detection of an erythropoiesis biomarker in a sample from the subject after administration of the therapeutic agent and methotrexate.

In some embodiments, there is provided a method for treating a subject (such as a human subject) in need of treatment with a therapeutic agent, comprising: (a) administering to the subject an effective amount of methotrexate, (b) administering to the subject an effective amount of the therapeutic agent, (c) detecting an erythropoiesis biomarker in a sample obtained from the subject between at least one day and about 30 days (such as about 7 days to about 14 days) after administration of methotrexate; and (d) continuing further treatment with the therapeutic agent with or without administering, additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, if the level of the erythropoiesis biomarker is approximately equal to or less than that of a control, step (d) comprises administering the additional immune tolerance induction therapy or the immunosuppression therapy concurrently with further treatment with the therapeutic agent; or if the level of the erythropoiesis biomarker is elevated with respect to that of a control, step (d) comprises continuing further treatment with the therapeutic agent without administering the additional immune tolerance induction therapy or the immunosuppression therapy. In some embodiments, the erythropoiesis biomarker is the level of immature nucleated red blood cells, immature reticulocyte fraction, or cellular nucleic acid contents. In some embodiments, if the level of the erythropoiesis biomarker is approximately elevated with respect to that of a control, step (d) comprises administering the additional immune tolerance induction therapy or the immunosuppression therapy concurrently with further treatment with the therapeutic agent; or if the level of the erythropoiesis biomarker is equal to or less than that of a control, step (d) comprises continuing further treatment with the therapeutic agent without administering the additional immune tolerance induction therapy or the immunosuppression therapy. In some embodiments, the erythropoiesis biomarker is hematocrit. In some embodiments, said detecting an erythropoiesis biomarker comprises detecting expression of a gene associated with erythropoiesis, wherein the gene is associated with one or more of hemopoiesis, iron ion homeostasis, regulation of erythrocyte differentiation, and here metabolism. In some embodiments, the gene associated with erythropoiesis is a gene encoding transferrin receptor (such as CD71), transferrin, Ly76, CD44, CD235a, ALAS2, or GATA-1. In some embodiments, the erythropoiesis biomarker is a co-factor associated with erythropoiesis, such as porphyrin, a porphyrin-containing compound, or a tetrapyrrole. In some embodiments, the effective amount of methotrexate is administered in a single cycle or in three cycles. In some embodiments, the effective amount of methotrexate is administered in one, two, three, four, five or more cycles. In some embodiments the methotrexate is administered between 48 hours prior to and 48 hours (such as about 24 and about 48 hours) after the administration of the therapeutic agent treatment. In some embodiments, the methotrexate is administered at a dose of 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy (e.g., more frequent and/or higher dose of the therapeutic, optionally with concomitant IVIG).

In some embodiments, there is provided a method for treating a subject in need of treatment with a therapeutic polypeptide (such as a monoclonal antibody or enzyme), comprising: (a) administering to the subject an effective amount of methotrexate; (b) administering to the subject an effective amount of the therapeutic polypeptide; (c) detecting an erythropoiesis biomarker in a sample obtained from the subject between at least one day and about 30 days (such as about 7 days to about 14 days) after administration of methotrexate; and (d) continuing further treatment with the therapeutic polypeptide with or without administering additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, if the level of the erythropoiesis biomarker is approximately equal to or less than that of a control, step (d) comprises administering the additional immune tolerance induction therapy or the immunosuppression therapy concurrently with further treatment with the therapeutic polypeptide; or if the level of the erythropoiesis biomarker is elevated with respect to that of a control, step (d) comprises continuing further treatment with the therapeutic polypeptide without administering the additional immune tolerance induction therapy or the immunosuppression therapy. In some embodiments, the erythropoiesis biomarker is the level of immature nucleated red blood cells, immature reticulocyte fraction, or cellular nucleic acid contents. In some embodiments, if the level of the erythropoiesis biomarker is approximately elevated with respect to that of a control, step (d) comprises administering the additional immune tolerance induction therapy or the immunosuppression therapy concurrently with further treatment with the therapeutic polypeptide; or if the level of the erythropoiesis biomarker is equal to or less than that of a control, step (d) comprises continuing further treatment with the therapeutic polypeptide without administering the additional immune tolerance induction therapy or the immunosuppression therapy. In some embodiments, the erythropoiesis biomarker is hematocrit. In some embodiments, said detecting an erythropoiesis biomarker comprises detecting expression of a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. In some embodiments, the erythropoiesis biomarker is a co-factor associated with erythropoiesis, such as porphyrin, a porphyrin-containing compound, or a tetrapyrrole. In some embodiments, the effective amount of methotrexate is administered in a single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the therapeutic polypeptide treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy more frequent and/or higher dose of the therapeutic, optionally with concomitant IVIG). In some embodiments, the therapeutic polypeptide is a lymphocyte-depleting agent, such as alemtuzumab. In some embodiments, the therapeutic polypeptide is an enzyme, such as human alpha galactosidase A, or human acid α-glucosidase.

In some embodiments, there is provided a method for treating a subject (such as a human subject) in need of treatment with a therapeutic polypeptide (such as a monoclonal antibody or enzyme), comprising: (a) administering to the subject an effective amount of methotrexate; (b) administering to the subject an effective amount of the therapeutic polypeptide; (c) detecting immature nucleated red blood cells in a sample obtained from the subject between at least one day and about 30 days after administration of methotrexate; and (d) if the level of the immature nucleated red blood cells is approximately equal to or less than that of a control, administering additional immune tolerance induction therapy or immunosuppression therapy concurrently with further treatment with the therapeutic polypeptide; or if the level of the immature nucleated red blood cells is elevated with respect to that of a control, continuing further treatment with the therapeutic polypeptide without administering additional immune tolerance induction therapy or immunosuppression therapy. In some embodiments, the sample is a blood sample or a sample of a blood fraction comprising peripheral blood mononuclear cells. In some embodiments, the sample is a plasma sample. In some embodiments, the control is a historical control or a placebo control. In some embodiments, the effective amount of methotrexate is administered in a single cycle or in three cycles. In some embodiments, the effective amount of methotrexate is administered in one, two, three, four. five or more cycles. In some embodiments. the methotrexate is administered between 48 hours prior to and 48 hours (such as about 24 and about 48 hours) after the administration of the therapeutic polypeptide treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy more frequent and/or higher dose of the therapeutic, optionally with concomitant In some embodiments, there is provided a method for treating a subject (such as a human subject) in need of treatment with a therapeutic polypeptide (such as a monoclonal antibody or enzyme), comprising: (a) administering to the subject an effective amount of methotrexate; (b) administering to the subject an effective amount of the therapeutic polypeptide; (c) detecting a gene (such as RNA transcript or protein) associated with erythropoiesis in a sample obtained from the subject between at least one day and about 30 days after administration of methotrexate; and (d) if the level of the gene associated with erythropoiesis is approximately equal to or less than that of a control, administering additional immune tolerance induction therapy or immunosuppression therapy concurrently with further treatment with the therapeutic polypeptide; or if the level of the a gene associated with erythropoiesis is elevated with respect to that of a control, continuing further treatment with the therapeutic polypeptide without administering additional immune tolerance induction therapy or immunosuppression therapy. In some embodiments, the gene associated with erythropoiesis is associated with one or more of hemopoiesis, iron ion homeostasis, regulation of erythrocyte differentiation, and home metabolism. In some embodiments, the gene associated with erythropoiesis is a gene encoding transferrin receptor such as CD71) transferrin, Ly76, CD44, CD235a, ALAS2, or GATA-1. in some embodiments, the sample is a blood sample or a sample of a blood fraction comprising, peripheral blood mononuclear cells. In some embodiments, the sample is a plasma sample. In some embodiments, the control is a historical control or a placebo control. In some embodiments, the effective amount of methotrexate is administered in a single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the therapeutic polypeptide treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy (e,g., more frequent and/or higher dose of the therapeutic, optionally with concomitant IVIG).

In some embodiments, there is provided a method for treating a subject (such as a human subject) in need of treatment with a therapeutic polypeptide (such as a monoclonal antibody or enzyme), comprising: (a) administering to the subject an effective amount of methotrexate, (b) administering to the subject an effective amount of the therapeutic polypeptide; (c) detecting a co-factor associated with erythropoiesis in a sample obtained from the subject between at least one day and about 30 days after administration of methotrexate, and (d) if the level of the co-factor associated with erythropoiesis is approximately equal to or less than that of a control, administering additional immune tolerance induction therapy or immunosuppression therapy concurrently with further treatment with the therapeutic polypeptide; or if the level of the co-factor associated with erythropoiesis is elevated with respect to that of a control, continuing further treatment with the therapeutic polypeptide without administering additional immune tolerance induction therapy or immunosuppression therapy. In some embodiments, the co-factor associated with erythropoiesis is porphyrin, a porphyrin-containing compound, or a tetrapyrrole. In some embodiments, the sample is a blood sample or a sample of a blood fraction comprising peripheral blood mononuclear cells. In some embodiments, the sample is a plasma sample. In some embodiments, the control is a historical control or a placebo control. In some embodiments, the effective amount of methotrexate is administered in a single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the therapeutic polypeptide treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy (e.g, more frequent and/or higher dose of the therapeutic, optionally with concomitant IVIG).

In some embodiments, there is provided a method for treating a subject with a lysosomal storage disease in need of treatment with a therapeutic agent (such as an enzyme), comprising: (a) administering to the subject an effective amount of methotrexate; (b) administering to the subject an effective amount of the therapeutic agent; (c) detecting an erythropoiesis biomarker in a sample obtained from the subject between at least one day and about 30 days (such as about 7 days to about 14 days) after administration of methotrexate; and (d) continuing further treatment with the therapeutic agent with or without administering additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, if the level of the erythropoiesis biomarker is approximately equal to or less than that of a control, step (d) comprises administering the additional immune tolerance induction therapy or the immunosuppression therapy concurrently with further treatment with the therapeutic agent, or if the level of the erythropoiesis biomarker is elevated with respect to that of a control, step (d) comprises continuing further treatment with the therapeutic agent without administering the additional immune tolerance induction therapy or the immunosuppression therapy. In some embodiments, the erythropoiesis biomarker is the level of immature nucleated red blood cells, immature reticulocyte fraction, or cellular nucleic acid contents. In some embodiments, if the level of the erythropoiesis biomarker is approximately elevated with respect to that of a control, step (d) comprises administering the additional immune tolerance induction therapy or the immunosuppression therapy concurrently with further treatment with the therapeutic agent; or if the level of the erythropoiesis biomarker is equal to or less than that of a control, step (d) comprises continuing further treatment with the therapeutic agent without administering the additional immune tolerance induction therapy or the immunosuppression therapy. In some embodiments, the erythropoiesis biomarker is hematocrit. In some embodiments, said detecting, an erythropoiesis biomarker comprises detecting expression of a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. in some embodiments, the erythropoiesis biomarker is a cofactor associated with erythropoiesis, such as porphyrin, a porphyrin-containing compound, or a tetrapyrrole. In some embodiments, the sample is a blood sample or a sample of a blood. fraction comprising peripheral blood mononuclear cells. In some embodiments, the sample is a plasma sample. In some embodiments, the control is a historical control or a placebo control. In some embodiments, the effective amount of methotrexate is administered in a. single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the therapeutic agent treatment. In some embodiments, the methotrexate is administered at 0.1 mg/kg to 5 mg/kg. In some embodiments, administering the additional immune tolerance induction -therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy (e.g., more frequent and/or higher dose of the therapeutic, optionally with concomitant (IVIG). In some embodiments, the therapeutic polypeptide is human alpha galactosidase A, or human acid α-glucosidase. In some embodiments, the subject has Gaucher disease, and is in need of human alpha galactosidase A.

In some embodiments, there is provided a method for treating, Pompe disease (such as infantile-onset and/or CSM-negative Pompe disease) in a subject (such as a human subject), comprising: (a) administering to the subject an effective amount of methotrexate; (b) administering to the subject an effective amount of a therapeutic agent (such as human acid α-glucosidase); (c) detecting an erythropoiesis biomarker in a sample obtained from the subject at least one day to about 30 days (such as about 7 days to about 14 days) after administration of methotrexate; and (d) continuing further treatment with the therapeutic agent with or without administering additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, if the level of the erythropoiesis biomarker is approximately equal to or less than that of a control, step (d) comprises administering the additional immune tolerance induction therapy or the immunosuppression therapy concurrently with further treatment with the therapeutic agent or if the level of the erythropoiesis biomarker is elevated with respect to that of a control, step (d) comprises continuing further treatment with the therapeutic agent without administering the additional immune tolerance induction therapy or the immunosuppression therapy. In some embodiments, the erythropoiesis biomarker is the level. of immature nucleated red blood. cells, immature reticulocyte fraction, or cellular nucleic acid contents. In some embodiments, if the level of the erythropoiesis biomarker is approximately elevated with respect to that of a control, step (d) comprises administering the additional immune tolerance induction therapy or the immunosuppression therapy concurrently with further treatment with the therapeutic agent; or if the level of the erythropoiesis biomarker is equal to or less than that of a control, step (d) comprises continuing further treatment with the therapeutic agent without administering the additional immune tolerance induction -therapy or the immunosuppression therapy. In some embodiments, the erythropoiesis biomarker is hematocrit. In some embodiments, said detecting an erythropoiesis biomarker comprises detecting expression of a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. In some embodiments, the erythropoiesis biomarker is a co-factor associated with erythropoiesis, such as porphyrin, a porphyrin-containing compound, or a tetrapyrrole. In some embodiments, the sample is a blood sample or a sample of a blood fraction comprising peripheral blood mononuclear cells. In some embodiments, the sample is a plasma sample. In some embodiments, the control is a historical control or a placebo control. In some embodiments, the effective amount of methotrexate is administered in a single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the therapeutic agent treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cycloptiosphamide, bortezomib, azathioprine, cyclosporine, mycophenolate, a corticosteroid; and administering an antigen-specific tolerance strategy (e.g., more frequent and/or higher dose of the therapeutic, optionally with concomitant IVIG). In some embodiments, step (d) further comprises administering an agent that depletes T-cells, B-cells, or plasma cells, such as bortezomib. In some embodiments, the method further comprises monitoring one or more of levels of antibodies against the therapeutic agent, level of CD19, and disease progression.

In some embodiments, there is provided a method for treating infantile-onset Pompe disease (such as classic infantile-onset Pompe disease) in a subject (such as a human subject), comprising (a) administering to the subject an effective amount of methotrexate; (b) administering to the subject an effective amount of human acid α-glucosidase concurrently with an initial immune tolerance induction therapy (such as rituximab and/or IVIG; (c) detecting an erythropoiesis biomarker in a sample obtained from the subject at least one day to about 30 days (such as about 7 days to about 14 days) after administration of methotrexate; and (d) continuing further treatment with the human acid α-glucosidase with or without administering additional immune tolerance induction therapy or immunosuppression therapy based on a level of the erythropoiesis biomarker compared to that of a control. In some embodiments, a change in the level of the erythropoiesis biomarker is associated with induction of erythropoiesis. In some embodiments, if the level of the erythropoiesis biomarker is approximately equal to or less than that of a control, step (d) comprises administering the additional immune tolerance induction therapy or the immunosuppression therapy concurrently with further treatment with the human acid α-glucosidase; or if the level of the erythropoiesis biomarker is elevated with respect to that of a control, step (d) comprises continuing further treatment with the human acid α-glucosidase without administering the additional immune tolerance induction therapy or the immunosuppression therapy. In some embodiments, the erythropoiesis biomarker is the level of immature nucleated red blood cells, immature reticulocyte fraction, or cellular nucleic acid contents. In some embodiments, if the level of the erythropoiesis biomarker is approximately elevated with respect to that of a control, step (d) comprises administering the additional immune tolerance induction therapy or the immunosuppression therapy concurrently with further treatment with the human acid α-glucosidase, or if the level of the erythropoiesis biomarker is equal to or less than that of a control, step (d) comprises continuing further treatment with the human acid α-glucosidase without administering the additional immune tolerance induction therapy or the immunosuppression therapy. In some embodiments, the erythropoiesis biomarker is hematocrit. In some embodiments, said detecting an erythropoiesis biomarker comprises detecting expression of a gene associated with erythropoiesis, wherein the gene is associated with one or more of hemopoiesis, iron. ion homeostasis, regulation of erythrocyte differentiation, and here metabolism. In some embodiments, the gene associated with erythropoiesis is a gene encoding transferrin. receptor (such as CD71), transferrin, Ly76, CD44, CD235a, ALAS2, or GATA-1. in some embodiments, the erythropoiesis biomarker is a co-factor associated with erythropoiesis, such as porphyrin, a porphyrin-containing compound, or a tetrapyrrole. In some embodiments, the sample is a blood sample or a sample of a. blood fraction comprising peripheral blood mononuclear cells. In some embodiments, the sample is a plasma sample. In some embodiments, the control is a historical control or a placebo control. In some embodiments, the effective amount of methotrexate is administered in a single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the human acid α-glucosidase treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy (e.g., more frequent and/or higher dose of the therapeutic, optionally with concomitant IVIG). In some embodiments, step (d) further comprises administering an agent that depletes T-cells, B-cells, or plasma cells, such as bortezomib. In some embodiments, the method further comprises monitoring one or more of anti-human acid α-glucosidase antibody (such as anti-rhGAA IgG antibody) and CD19 levels, and disease progression. In some embodiments, the infantile-onset Pompe disease is a CRIM-negative Pompe disease.

In some embodiments, there is provided a method for treating a subject with Pompe disease (such as infantile-onset and/or GRIM-negative Pompe disease), comprising: (a) obtaining a sample from the subject, wherein the subject has previously been administered at least one cycle of methotrexate treatment and at least one dose of a therapeutic agent (such as human acid α-glucosidase); (b) detecting an erythropoiesis biomarker in the sample at least one day to about 30 days (such as about 7 days to about 14 days) after administration of methotrexate; and (c) continuing further treatment with the therapeutic agent with or without administering additional immune tolerance induction therapy or immunosuppression therapy based on a level of the erythropoiesis biomarker compared to that of a control. In some embodiments, a change in the level. of the erythropoiesis biomarker is associated with induction of erythropoiesis. In some embodiments, if he level of the erythropoiesis biomarker is approximately equal to or less than that of a control, step (c) comprises administering the additional immune tolerance induction therapy or he immunosuppression therapy concurrently with further treatment with the therapeutic agent; or if the level of the erythropoiesis biomarker is elevated with respect to that of a control, step (c) comprises continuing further treatment with the therapeutic agent without administering the additional immune tolerance induction therapy or the immunosuppression therapy. In some embodiments, the erythropoiesis biomarker is the level of immature nucleated red blood cells, immature reticulocyte fraction, or cellular nucleic acid contents. In some embodiments, if the level of the erythropoiesis biomarker is approximately elevated with respect to that of a control, step (c) comprises administering the additional immune tolerance induction therapy or the immunosuppression therapy concurrently with further treatment with the therapeutic agent; or if the level of the erythropoiesis biomarker is equal to or less than that of a control, continuing further treatment with the therapeutic agent without administering the additional immune tolerance induction therapy or the immunosuppression therapy. In some embodiments, the erythropoiesis biomarker is hematocrit. In some embodiments, said detecting an erythropoiesis biomarker comprises detecting expression of a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. In some embodiments, the erythropoiesis biomarker is a co-factor associated with erythropoiesis, such as porphyrin, a porphyrin-containing compound, or a tetrapyrrole. In some embodiments, the sample is a blood sample or a sample of a blood fraction comprising peripheral blood mononuclear cells. In some embodiments, the sample is a plasma sample. In some embodiments, the control is a historical control or a placebo control. In some embodiments, the effective amount of methotrexate is administered in a single cycle or in three cycles. In some embodiments, the effective amount of methotrexate is administered in one, two, three, four, five or more cycles. In some embodiments, the methotrexate is administered between 48 hours prior to and 48 hours (such as about 24 and about 48 hours) after the administration of the therapeutic agent treatment. In some embodiments, the methotrexate is administered at 0.1 mg/kg to 5 mg/kg. In some embodiments, administering the additional immune tolerance induction therapy or immunosuppression therapy comprises administering one or more of rituximab, intravenous immunoglobulin (IVIG), cyclophosphamide, bortezomib, azathioprine, cyclosporine, mycophenolate, a corticosteroid; and administering an antigen-specific tolerance strategy (e.g., more frequent and/or higher dose of the therapeutic, optionally with concomitant IVIG). In some embodiments, step (d) further comprises administering an agent that depletes T-cells, B-cells, or plasma cells, such as bortezomib. In some embodiments, the method further comprises monitoring one or more of levels of antibodies against the therapeutic agent, level of CD-19, and disease progression.

One aspect of the present application provides a method for assessing the level of immune tolerance to a therapeutic agent in a subject in need of the therapeutic agent, comprising (a) administering to the subject an effective amount of methotrexate; (b) administering to the subject a therapeutically effective amount of the therapeutic agent; and (c) detecting an erythropoiesis biomarker in a sample obtained from the subject, wherein a level of the erythropoiesis biomarker in the sample with respect to the level of a control indicates induction of immune tolerance in the subject to the therapeutic agent. In some embodiments, a change in the level of the erythropoiesis biomarker is associated with induction of erythropoiesis. In some embodiments, if the level of the erythropoiesis biomarker is approximately equal to or less than that of a control, the subject is in need of additional immune tolerance induction therapy or immunosuppression therapy concurrently with further treatment with the therapeutic agent; or if the level of the erythropoiesis biomarker is elevated with respect to that of a control, the subject is not in need of additional immune tolerance induction therapy or immunosuppression therapy. In some embodiments, the erythropoiesis biomarker is the level of immature nucleated red blood cells, immature reticulocyte fraction, or cellular nucleic acid contents. In some embodiments, the erythropoiesis biomarker is a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. in some embodiments, the erythropoiesis biomarker is a co-factor associated with erythropoiesis, such as porphyrin, a porphyrin-containing compound, or a tetrapyrrole. In some embodiments, if the level of the erythropoiesis biomarker is approximately elevated with respect to that of a control, the subject is in need of additional immune tolerance induction therapy or immunosuppression therapy concurrently with further treatment with the therapeutic agent:, or wherein if the level of the erythropoiesis biomarker is equal to or less than that of a control, the subject is not in need of additional immune tolerance induction therapy or immunosuppression therapy. In some embodiments, the erythropoiesis biomarker is hemocrit. In some embodiments, the sample is a blood sample or a sample of a blood fraction comprising peripheral blood mononuclear cells. In some embodiments, the sample is a plasma sample. In some embodiments, the control is a historical control or a placebo control.

In some embodiments, there is provided a method for assessing the level of immune tolerance to a therapeutic agent in a subject in need of the therapeutic agent, comprising (a) administering to the subject an effective amount of methotrexate; (b) administering to the subject a therapeutically effective amount of the therapeutic agent; and (c) detecting an erythropoiesis biomarker at least one day to about 30 days (such as about 7 days to about 14 days) after administration of methotrexate, wherein detection of an elevated level of an erythropoiesis biomarker denotes induction of immune tolerance in the subject to the therapeutic agent. In some embodiments, a change in the level of the erythropoiesis biomarker is associated with induction of erythropoiesis. In some embodiments, if the level of the erythropoiesis biomarker is approximately equal to or less than that of a control, the subject is in need of additional immune tolerance induction therapy or immunosuppression therapy concurrently with further treatment with the therapeutic agent; or if the level of the erythropoiesis biomarker is elevated with respect to that of a control, the subject is not in need of additional immune tolerance induction therapy or immunosuppression therapy. In some embodiments, the erythropoiesis biomarker is the level of immature nucleated red blood cells, immature reticulocyte fraction, or cellular nucleic acid contents. In some embodiments, the erythropoiesis biomarker is a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. In some embodiments, the erythropoiesis biomarker is a co-factor associated with erythropoiesis, such as porphyrin, a porphyrin-containing compound, or a tetrapyrrole. In some embodiments, if the level of the erythropoiesis biomarker is approximately elevated with respect to that of a control, the subject is in need of additional immune tolerance induction therapy or immunosuppression therapy concurrently with further treatment with the therapeutic agent; or wherein if the level of the erythropoiesis biomarker is equal to or less than that of a control, the subject is not in need of additional immune tolerance induction therapy or immunosuppression therapy. In some embodiments, the erythropoiesis biomarker is hemocrit. In some embodiments, the sample is a blood sample or a sample of a blood fraction comprising peripheral blood mononuclear cells. In some embodiments, the sample is a plasma sample. In some embodiments, the control is a historical control or a placebo control.

In some embodiments, there is provided a method for assessing immune tolerance in a subject with Pompe disease, comprising: (a) obtaining a sample from the subject, wherein the subject has previously been administered at least one cycle of methotrexate treatment and at least one dose of the therapeutic agent; and (b) contacting the sample with an agent that binds to an erythropoiesis biomarker, wherein detection of an elevated level of the erythropoiesis biomarker over a control indicates an induction of immune tolerance. In some embodiments, a change in the level of the erythropoiesis biomarker is associated with induction of erythropoiesis. In some embodiments, if the level of the erythropoiesis biomarker is approximately equal to or less than that of a control, the subject is in need of additional immune tolerance induction therapy or immunosuppression therapy concurrently with further treatment with the therapeutic agent; or if the level of the erythropoiesis biomarker is elevated with respect to that of a control, the subject is not in need of additional immune tolerance induction therapy or immunosuppression therapy. In some embodiments, the erythropoiesis biomarkers is the level of immature nucleated red blood cells, immature reticulocyte fraction, or cellular nucleic acid contents. In some embodiments, the erythropoiesis biomarker is a gene associated with erythropoiesis, wherein the gene is associated with one or more of hemopoiesis, iron ion homeostasis, regulation of erythrocyte differentiation, and heme metabolism. In some embodiments, the gene associated with erythropoiesis is a gene encoding transferrin receptor (such as CD71), transferrin, Ly76, CD44, CD235a, ALAS2, or GATA-1. In some embodiments, the erythropoiesis biomarker is a co-factor associated with erythropoiesis, such as porphyrin, a porphyrin-containing compound, or a tetrapyrrole. In some embodiments, if the level of the erythropoiesis biomarker is approximately elevated with respect to that of a control, the subject is m need of additional immune tolerance induction therapy or immunosuppression therapy concurrently with further treatment with the therapeutic agent; or wherein if the level of the erythropoiesis biomarker is equal to or less than that of a control, the subject is not m need of additional immune tolerance induction therapy or immunosuppression therapy. In some embodiments, the erythropoiesis biomarker is hemocrit. In some embodiments, the sample is a blood sample or a sample of a blood fraction comprising peripheral blood mononuclear cells. In some embodiments, the sample is a plasma sample. In some embodiments, the control is a historical control or a placebo control.

A. Erythropoiesis Biomarkers

The present application provides methods of detecting one or more erythropoiesis biomarkers in a sample. The erythropoiesis biomarkers described herein can be used singly or in combination at any suitable time of the treatment to monitor immune tolerance induction. In some embodiments, detection of the erythropoiesis biomarker at a level above that of a control is indicative of immune tolerance to the therapeutic induced by methotrexate administration in the subject. In some embodiments, the subject is more likely to respond to further treatment with the therapeutic agent without concurrently administrating additional immune tolerance induction therapy or immunosuppression therapy if the erythropoiesis biomarker is detected at an elevated level. In some embodiments, the subject is likely to benefit from concurrent administration of additional immune tolerance induction therapy or immunosuppression therapy with further treatment with the therapeutic agent if the erythropoiesis biomarker is detected at or below the level of a control.

In some embodiments, the level of an erythropoiesis biomarker in a control is pre-determined. In some embodiments, the level of an erythropoiesis biomarker in a control is based on the average or medium level of the erythropoiesis biomarker in the individual prior to receiving the methotrexate and/or the therapeutic agent. In some embodiments, the level of an erythropoiesis biomarker in a control is based on the average or median level of the erythropoiesis biomarker in one or more healthy individuals. In some embodiments, the level of an erythropoiesis biomarker in a control is based on the average or median level of the erythropoiesis biomarker in one or more individuals having the same disease or condition (such as Pompe disease) as the individual receiving the therapeutic agent. In some embodiments, the level of an erythropoiesis biomarker in a control is based on the average or median level of the erythropoiesis biomarker in one or more individuals in need of the therapeutic agent prior to or without receiving the methotrexate and/or the therapeutic agent. In some embodiments, the level of an erythropoiesis biomarker in a control is based on the average or median level of the erythropoiesis biomarker in one or more individuals who have induced immune tolerance to the therapeutic agent by the methotrexate treatment. In some embodiments, the level of an erythropoiesis biomarker in a control is based on the average or median level of the erythropoiesis biomarker in one or more individuals who have received treatment with the therapeutic agent, but who do not have an immune response (such as ADA) against the therapeutic agent. In some embodiments, the level of an erythropoiesis biomarker in a control is determined based on a control sample.

The present application discloses, in part, further evaluation of the mechanism of methotrexate induced immune tolerance by transcriptional, proteomic, and cellular analysis of samples isolated at the 7-day time point when immune tolerance can be adoptively transferred. This evaluation identified various genes associated with erythropoiesis as biomarkers for induction of immune tolerance. The disclosure also relates to the discovery that methotrexate temporarily depletes red blood cells (RBCs), thereby inducing erythropoiesis, as demonstrated by a greater frequency and appearance of immature, nucleated RBCs in the splenic red pulp.

In some embodiments, an erythropoiesis biomarker is detected between at least one day and about 30 days after administration of methotrexate. In some embodiments, the erythropoiesis biomarker is detected a plurality of times after administration of methotrexate. In some embodiments, the erythropoiesis biomarker is detected at one or more of 1, 2, 3, 4, 5, 6, 7, 8, 9, 10, 11, 12, 13, 14 15, 16, 17, 18, 19, 20, 21, 22, 23, 24, 25, 26, 27, 28, 29, or 30 days after administration of methotrexate. In some embodiments, the methotrexate is administered in a cycle. For example, a single cycle of methotrexate may consist of a single dose of methotrexate, or about any one of 2, 3, 4, 5, 6, 7, 8, 9, 10, or 11 consecutive daily doses of methotrexate. In some embodiments, the erythropoiesis biomarker is detected between one day and about 30 days following the last methotrexate administration of a cycle. In some embodiments, the erythropoiesis biomarker is detected between one day and about 30 days following the first methotrexate administration of a cycle. In some embodiments, the methotrexate is administered in a single cycle, two cycles or three cycles. In some embodiments, the effective amount of methotrexate is administered in one, two, three, four, five or more cycles. In some embodiments, the erythropoiesis biomarker is detected between one day and about 30 days following the last methotrexate administration of a single cycle or first cycle of multiple cycles. In some embodiments, the erythropoiesis biomarker is detected between one day and about 30 days following the first methotrexate administration of a single cycle or first cycle of multiple cycles. In sonic embodiments, the erythropoiesis biomarker is detected between one day and about 30 days following the last methotrexate administration of a third cycle. In some embodiments, the erythropoiesis biomarker is detected between one day and about 30 days following the first methotrexate administration of a single or third cycle.

In some embodiments, the erythropoiesis biomarker is the level of immature nucleated red blood cells. In some embodiments, the level of immature nucleated red blood cells decreases following administration of methotrexate but then increases over time such that the level of immature nucleated red blood cells is elevated compared to a reference sample. In some embodiments, the level of immature red blood cells decreases after about any of one, two, three, four, five, six, or seven days or any time period between about one and seven days following, methotrexate administration. In some embodiments, the level of immature red blood cells decreases after about any of one, two, three, four, five, six, or seven days or any time period between about one and seven days following the last methotrexate administration in a cycle of methotrexate administration. In some embodiments, the level of immature red blood cells decreases after about any of one, two, three, four, five, six, or seven days or any time period between about one and seven days following the first methotrexate administration in a cycle of methotrexate administration. In some embodiments, the level of immature red blood cells is elevated after more than about any of one, two, three, four, five, six, seven, 14, 21, 28 or 30 days or any time period between about one and 30 days following methotrexate administration. In some embodiments, the level of immature red blood cells is elevated after more than about any of one, two, three, four, five, six, seven, 14, 21, 28 or 30 days or any time period between about one and 30 days following the last methotrexate administration in a cycle of methotrexate administration. In some embodiments, the level of immature red blood cells is elevated after more than about any of one, two, three, four, five, six, seven, 14. 21, 28 or 30 days or any time period between about one and 30 days following the first methotrexate administration in a cycle of methotrexate administration.

Erythropoiesis is the process in which immature, nucleated RBCs, otherwise known as erythroid progenitors, develop into non-nucleated, discoid-shaped mature red blood cells (Nandakumar et. al., 2016). Immature, nucleated RBCs can. be identified by the cell surface transferrin receptor CD71 (Pan and Johnstone 1983). The earliest immature, nucleated RBC or erythroblast in hematopoietic tissue is the proerythroblast. Through successive stages of mitosis, proerythroblasts which eventually differentiates in morphologically distinct through multiple stages of mitosis, successively becoming basophilic, polychromatic, then orthochromatic erythroblasts, then events into reticulocytes (with expelled nuclei), and finally becomes mature red blood cells (Nandakumar et. al., 2016). The erythroid-specific monoclonal antibody Ter-119 reacts with erythroid cells throughout the various differentiation stages from nucleated proerythroblast to enucleated mature red blood cells (King et. al., 2000). Early nucleated erythroblasts and reticulocytes, but not mature erythrocytes or red blood cells, express the transferrin receptor CD71 (Pan and Johnstone 1983). The proerythroblast and the distinct successive stages of erythropoiesis development can be unambiguously identified through the expression of CD71 or similarly through the differential expression of the adhesion molecule CD44 (Chen et. al., 2009, Koulnis et. al., 2011). in mice, mature red blood cells can circulate in the body for up to 40 days upon which they undergo senescence due to age and natural deterioration (Van Putten 1958). Aged RBCs undergo a specialized form of apoptosis called eryptosis and are cleared from circulation (Daugas et. al., 2001, Testa 2004). Importantly, mature RBCs and immature, nucleated RBCs have been suggested to have immune modulatory capacity through independent mechanisms (Schakel et. al., 2006; Cremel et al., 2013; Getts et. al., 2013; Cremel et. al., 2015; Grimm et. al., 2015; Lorentz et. al., 2015; Yi et al., 2015).

Clearance of mature RBCs is believed to provide sustained and ongoing, immune tolerance to self-antigens (Cremel et. al., 2013; Getts et. al., 2013). Theoretically, aged RBCs undergoing eryptosis are cleared tolerogenically, thereby inducing tolerance to the RBC and its entire antigen payload. By taking advantage of this natural phenomenon, a number of groups have achieved immune tolerance to biologic therapies in mice by encapsulating or associating target protein sequences to mature red blood cells (Kontos et. al., 2013; Cremel et. al., 2015; Grimm et. al., 2015; Lorentz et. al., 2015). Alternatively, immature, nucleated RBCs that express CD71 have been suggested to directly mediate the inherent immunosuppression in neonates (Elahi et. al., 2013). Additionally, emerging literature has shown, RBCs can inhibit the capacity of dendritic cells to promote T cell activation and antibody responses through the interaction of CD47 on RBCs with signal regulatory protein α (SIRPα) on dendritic cells (Schakel et. al., 2006; Yi et cal., 2015).

Through the above discussed and/or other mechanisms, without being bound by theory, erythropoiesis induced by methotrexate as described herein may further promote immune tolerance induction to biologic therapies. Thus, the erythropoiesis biomarkers described herein can provide accurate and convenient early assessment of the level of immune tolerance induced by transient low-dose methotrexate treatment, which can be used to guide choice of immune tolerance induction and/or immunosuppression therapies to supplement further cycles of treatment with the therapeutic agent.

In some embodiments, the erythropoiesis biomarker is a total erythroid cell population or a subset of erythroid cells. The level of a given erythroid cell population can be expressed in a number of ways, as will be appreciated by one of skill in the art. For example, the level of a population can be expressed as a comparative percentage, fraction or frequency (e.g., of total blood cells or total peripheral blood mononuclear cells), an absolute number, or a concentration (e.g., cells/ml). Erythroid cells are generally obtained from whole blood or cellular blood fractions, though erythroid cells can also be obtained from spleen, bone marrow or other tissues. In some embodiments, the erythropoiesis biomarker is hematocrit. As used herein, "hematocrit" refers to the ratio of the volume of red blood cells to the total volume of blood. In some embodiments, the erythropoiesis biomarker is the level of a subset of erythroid cells. As referred herein, "erythroid cells" and "red blood cells" "RFCs") are used interchangeably to refer to all cell types in the erythroid lineage, which are characterized by expression of Ly-76(i.e. antigen of antibody Ter-119) on the cell surface of murine RBCs or CD235a, on the cell surface of human PBMCs. Erythroid cells include proerythroblasts, basophilic erythroblasts, polychromatic erythroblasts, orthochromatic erythroblasts, reticulocytes, including immature reticulocytes, and erythrocytes (i.e. mature red blood cells). In some embodiments, the erythropoiesis biomarker is the level of erythroid progenitor cells. In some embodiments, the erythropoiesis biomarker is the level of immature nucleated red blood cells (RBCs). An "immature nucleated red blood cell" is a red blood cell progenitor having a nucleus, characterized by expression of Ly76 (antigen of Ter-119) and transferrin receptor CD71 the cell surface. Immature nucleated RBCS include the RBC progenitors that include a nucleus from proerthroblasts to immature reticulocytes. In some embodiments, the erythropoiesis biomarker is immature reticulocyte fraction (also known as "IRF"). In some embodiments, the erythropoiesis biomarker is the level of mature red blood cells. Mature reticulocytes are reticulocytes that have ejected the nuclei. and will transform into mature erythrocytes.

In some embodiment, the erythropoiesis biomarker is cellular nucleic acid contents. In some embodiments, the erythropoiesis biomarker is cellular RNA content, such as the RNA content of total blood cells in a blood sample. In some embodiments, the erythropoiesis biomarker is cellular DNA content, such as the DNA content of total blood cells in a blood sample. The reticulocyte level in a blood sample correlates with the RNA and/or DNA content of blood cells in the blood sample.

The various levels of erythroid cell subpopulations and the nucleic acid contents of total blood cells can be measured using known methods in the art. Commercial automatic cell counting systems, such as SYSMEX® Hematology Analyzers, are available to determine the blood parameters, including immature nucleated RBC level, immature reticulocyte fraction, hematocrit, and RNA/DNA contents of total blood cells.

The erythropoiesis biomarkers identified herein include genes associated with erythropoiesis, and/or one or more subsets of erythroid cells, which are referred to herein as "erythropoiesis biomarker genes". In some embodiments, the erythropoiesis biomarker is a gene associated with one or more biochemical pathways in erythropoiesis, including, for example, hemopoiesis, iron ion homeostasis, regulation of erythrocyte differentiation, and home metabolism. In some embodiments, the erythropoiesis biomarker is a gene selected from the group of upregulated genes in the rhGAA+ MTX group shown in FIGS. 1A and 1B. Exemplary genes include, but are not limited to, transferrin receptor, transferrin, Ly76, CD44, CD235a., ALAS2, and GATA-1. In some embodiments, the erythropoiesis biomarker is a gene encoding a cell surface marker expressed by erythroid cells or a subset of erythroid cells. In some embodiments, the erythropoiesis biomarker is Ly76 (antigen for Ter-119) or CD235a. CD235a, is also known as glycophorin A, GYPA, MN, MNS, GPSAT, PAS-2, GPErik, HgpMiv, HgpMiXI, or HgpSta(C). In some embodiments, the erythropoiesis biomarker is transferrin receptor. In some embodiments, the erythropoiesis is transferrin receptor 1. Transferrin receptor 1 is also known as TfR1, Cluster of Differentiation 71, CD71, T9, TR, TFR, p90, TRFR, or IMD46. In some embodiments, the erythropoiesis biomarker is transferrin. Transferrin is also known as TF, TFQTL1, PRO1557, PRO2086 or HEL-S-71p. In some embodiments, the erythropoiesis biomarker is CD44. CD44 is also known as IN, LHR, MC56, MDU2, MDU3, MIC4, Pgp1, CDW44, CSPG8, HCELL, HUTCH-1 or ECMR-III. In some embodiments, the erythropoiesis biomarkers is a gene expressed by erythroid cells or a subset of erythroid cells. In some embodiments, the erythropoiesis biomarker is hemoglobin. In some embodiments, the erythropoiesis biomarker is a gene expressed by mature red blood cells, such as erythroid ankyrin or glycophorin C.

Expression levels of one or more genes associated with erythropoiesis or encoding cell surface markers of erythroid cells can be determined qualitatively and/or quantitatively based on any suitable criterion known in the art, including but not limited to DNA, mRNA, cDNA, proteins, protein fragments and/or gene copy number. "Expression level" and "amount" of a biomarker gene are used interchangeably herein. In some embodiments, the expression level of a biomarker gene in a first sample is increased or elevated as compared to expression level in a second sample. In some embodiments, the expression level of a biomarkers gene in a first sample is decreased or reduced as compared to the expression level in a second sample. In certain embodiments, the second sample is a reference (such as reference sample, reference cell, or reference tissue) or a control (such as control sample, control cell, or control tissue). In some embodiments, the control is a historical control or a placebo control. "Historical control" refers to a control obtained in one or more previous experiments. In some embodiments, the historical control is a control based on one or more clinical trials. Placebo control refers to a control obtained from a subject who does not receive the methotrexate treatment or the therapeutic agent treatment, or who receives the therapeutic agent treatment without the methotrexate treatment. Detection of an "elevated" or "increased" expression level of a biomarker gene in a first sample compared to the expression level in a control sample may indicate "presence" of the biomarker gene in the first sample. Detection of a "reduced" or "decreased" expression level of a biomarker gene in a first sample compared to the expression level in a control sample may indicate "absence" of the biomarker gene in the first sample. Additional disclosures for determining the expression level of a biomarker gene are described herein. In some embodiments, the erythropoiesis biomarker is transferrin receptor (such as CD71), transferrin, Ly76, CD44, CD235a ALAS2, and/or GATA-1. In some embodiments, the erythropoiesis biomarker is hemoglobin, erythroid, ankyrin, and/or glycophorin C.

In some embodiments, the erythropoiesis biomarker is a co-factor associated with erythropoiesis. Exemplary co-factors associated with erythropoiesis include, but are not limited to, porphyrin, porphyrin-containing compounds, or tetrapyrroles. Co-factor levels can be measured using any known methods in the an, including, for example, mass spectroscopy and HPLC.

In some embodiments, the erythropoiesis biomarker is the presence of immature nucleated red blood cells. In some embodiments, the level of immature nucleated red blood cells decreases following administration of methotrexate but then increases over time such that the level of immature nucleated red blood cells is elevated compared to a reference sample. In some embodiments, the level of immature red blood cells decreases after about any of one, two, three, four, five, six, or seven days or any time period between about one and seven days following methotrexate administration. In some embodiments, the level of immature red blood cells decreases after about any of one, two, three, four, five, six, or seven days or any time period between about one and seven days following the last methotrexate administration in a cycle of methotrexate administration. In some embodiments, the level of immature red blood cells decreases after about any of one, two, three, four, five, six, or seven days or any time period between about one and seven days following the first methotrexate administration in a cycle of methotrexate administration. in some embodiments, wherein the methotrexate is administered in a single cycle, the level of immature nucleated red blood cells decreases by about one, about two, about three, about four, about five, about six, or about seven days before the level of immature nucleated red blood cells becomes elevated. In some embodiments, wherein the methotrexate is administered in two or more cycles, the level of immature nucleated red blood cells decreases by about one to about 14 days before the level of immature nucleated red blood cells becomes elevated. In some embodiments, the level of immature red blood cells is elevated after more than about any of one, two, three, four, five, six, seven, 14, 21, 28 or 30 days or any time period. between about one and 30 days following methotrexate administration. In some embodiments, the level of immature red blood cells is elevated after more than about any of one, two, three, four, five, six, seven, 14, 21, 28 or 30 days or any time period between about one and 30 days following the last methotrexate administration in a cycle of methotrexate administration. In some embodiments. the level of immature red blood cells is elevated after more than about any of one, two, three, four, five, six, seven, 14, 21, 28 or 30 days or any time period between. about one and 30 days following the first methotrexate administration in a cycle of methotrexate administration.

Levels of one or more subsets of erythroid cells can be determined qualitatively and/or quantitatively based on any suitable criterion known in the art, including, for example, expression of suitable cell surface markers, histology markers, and morphology (e.g., cell volume, and presence or absence of nuclei). As used herein, "level" of a subset of erythroid cells refers to the number of cells, the fraction of the subset of erythroid cells among all erythroid cells, or frequency of erythroid cells in the total blood cells or PBMCs. In some embodiments, the level of a subset of erythroid cells in a first sample is increased or elevated as compared to the level in a second sample. In some embodiments, the level of a subset of erythroid cells in a first sample is decreased or reduced as compared to the level in a second sample. In certain embodiments, the second sample is a reference (such as reference sample or reference tissue) or a control (such as control sample or control tissue). In some embodiments, the control sample/tissue is a historical control or a placebo control. Detection of an "elevated" or "increased" level of a subset of erythroid cells in a first sample compared to the level of a control sample may indicate "presence" of the subset of erythroid cells in the first sample. Detection of a "reduced" or "decreased" level of a subset of erythroid cells in a first sample compared to the level of a control sample may indicate "absence" of the subset of erythroid cells in the first sample. Additional disclosures for determining the level of a subset of erythroid cells are described herein. In some embodiments, the erythropoiesis biomarker is the level (e.g., number, fraction, or frequency) of immature nucleated RBCs. In some embodiments, the erythropoiesis biomarker is immature reticulocyte fraction. In some embodiments, the erythropoiesis biomarker is hematocrit.

In some embodiments of any one of the methods, an elevated level of an erythropoiesis biomarker refers to an overall increase of at least about any one of 10%, 20%, 30%, 40%, 50%, 60%, 70%, 80%, 90%, 95%, 96%, 97%, 98%, 99% or greater, in the level of the erythropoiesis biomarker, such as expression level (e.g., protein or mRNA) of a gene associated with erythropoiesis or a gene encoding a cell surface marker of erythroid cells, or level (e.g., number, fraction, or frequency) of a subset of erythroid cells, as detected by standard methods known in the art such as those described herein, as compared to a reference or a control. In some embodiments, an elevated level of an erythropoiesis biomarker refers to an increase in the level of the erythropoiesis biomarker in the sample wherein the increase is at least about any one of 1.5×, 1.75×, 2×, 3×, 4×, 5×, 6×, 7×, 8×, 9×, 10×, 25×, 50×, 75×, or 100× the level of the respective erythropoiesis biomarker in a reference or a control. In some embodiments, an elevated level of an erythropoiesis biomarker refers to an overall increase of greater than about 1.5 fold, about 1.75 fold, about 2 fold, about 2.25 fold, about 2.5 fold, about 2.75 fold, about 3.0 fold, or about 3.25 fold as compared to a reference or a control. In some embodiments, the level of an erythropoiesis biomarker is relative to a control that is a median value of the level of the biomarker in a particular sample or grout of samples. For example, in some embodiments, the control is a median level of the erythropoiesis biomarker from a sample of a subject in which immune tolerance to a therapeutic agent has been induced by methotrexate treatment, such as by a transient low-dose methotrexate ITI regimen. In some embodiments, the median level of an erythropoiesis biomarker is derived from a database of patients having a particular disease in which immune tolerance to a therapeutic agent has been induced by methotrexate treatment. In some embodiments, the median level of an erythropoiesis biomarker is derived from a database of patients in need of treatment with a particular therapeutic agent in which immune tolerance to the therapeutic agent has been induced by methotrexate. For example, the expression level of an erythropoiesis biomarker gene for a patient with Pompe disease in need of rhGAA treatment may be compared to the median expression level of the erythropoiesis biomarker gene based on data in a database of Pompe disease patients who developed immune tolerance to rhGAA due to methotrexate treatment or do not develop an immune response to rhGAA. In some embodiments, the erythropoiesis biomarker is transferrin receptor (such as CD71), transferrin, Ly76, CD44, CD235a, ALAS2, or GATA-1. In some embodiments, the erythropoiesis biomarker is the level (e.g., number, fraction, or frequency) of immature nucleated RBCs.

In some embodiments of any of the methods, a reduced level of an erythropoiesis biomarker refers to an overall reduction of about any of 10%, 20%, 30%, 40%, 50%, 60%, 70%, 80%, 90%, 95%, 96%, 97%, 98%, 99% or greater, in the level of the erythropoiesis biomarker, such as expression level (e.g., protein. or mRNA) of a gene associated with erythropoiesis or a gene encoding a cell surface marker of erythroid cells, or level (e.g., number, fraction, or frequency) of a subset of erythroid cells, as detected by standard art known methods such as those described herein, as compared to a reference or a control. In some embodiments, a reduced level of an erythropoiesis biomarker refers to the decrease in the level of the erythropoiesis biomarker in the sample wherein the decrease is at least about any of 0.9×, 0.8×, 0.7×, 0.6×, 0.5×, 0.4×, 0.3×, 0.2×, 0.1×, 0.05×, or 0.01× the level of the respective erythropoiesis biomarker in a reference or a control. In some embodiments, the erythropoiesis biomarker is hemoglobin, erythroid ankyrin, or glycophorin C. In some embodiments, the erythropoiesis biomarker is the level of total erythroid cells or mature RBCs. In some embodiments, the erythropoiesis biomarker is immature reticulocyte fraction. in some embodiments, the erythropoiesis biomarker is hematocrit.

In some embodiments, the erythropoiesis biomarker has an elevated level on about any one of 1, 2, 3, 4, 5, 6, 7, 8, 9. 10. 12, 14, 16, 18, 20, 24 or 28 days after initial administration of methotrexate and/or the therapeutic agent. In some embodiments, the erythropoiesis biomarker has a reduced level on about any one of 1, 2, 3, 4, 5, 6, 7, 8, 9. 10. 12, 14, 16, 18, 20, 24 or 28 days after initial administration of methotrexate and/or the therapeutic agent. In some embodiments, the erythropoiesis biomarker has an elevated level on about any one of 1, 2, 3, 4, 5, 6, 7, 8, 9, 10, 12, 14. 16, 18, 20, 24 or 28 days after the final administration of methotrexate. In some embodiments, the erythropoiesis biomarker has a reduced level on about any one of 1, 2, 3, 4, 5, 6, 7, 8, 9, 10, 12, 14, 16, 18, 20, 24 or 28 days after the final administration of methotrexate. In some embodiments, the methotrexate is administered in a single cycle. In some embodiments, the methotrexate is administered in three cycles. In some embodiments, the effective amount of methotrexate is administered in one, two, three, four, five or more cycles. In some embodiments, the erythropoiesis biomarker has an elevated level on about any one of 1, 2, 3, 4, 5, 6, 7, 8, 9, 10, 12, 14, 15, 18, 20, 24 or 28 days after the final administration of methotrexate in a first cycle or a third cycle. In some embodiments, the erythropoiesis biomarker has an elevated level on about any one of 1, 2, 3, 4, 5, 6, 7, 8, 9, 10, 12, 14, 15, 18, 20, 24 or 28 days after the final administration of methotrexate in a first, second, third, fourth, or fifth cycle. In some embodiments, the erythropoiesis biomarker has a reduced level on about any one of 1, 2, 3, 4, 5, 6, 7, 8, 9, 10, 12, 14, 16, 18, 20, 24 or 28 days after the final administration of methotrexate in a first cycle or a third cycle. In some embodiments, the erythropoiesis biomarker has a reduced level on about any one of 1, 2, 3, 4, 5, 6, 7, 8, 9, 10, 12, 14, 15, 18, 20, 24 or 28 days after the final administration of methotrexate in a first, second, third, fourth or fifth cycle. In some embodiments, the level of the erythropoiesis biomarker first decreases and then increases after initial administration of methotrexate and/or the therapeutic agent. In some embodiments, the erythropoiesis biomarker, such as immature nucleated RBCs, immature reticulocyte fraction, cellular nucleic acid contents, a gene selected from transferrin receptor, transferrin, Ly76 (antigen for Ter-119), CD44, CD235a, ALAS2, and GATA-1, or a co-factor associated with erythropoiesis has an elevated level in a blood sample (such as PBMC or plasma. sample), of the subject between day 6 and day 16 (such as anyone of day 7, day 8, day 9, day 10, day 11, day 12, day 13 and day 14) after initiation of treatment with the therapeutic agent.

The expression levels of various erythropoiesis biomarker genes in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MASSARRAY®, proteomics, mass spectrometry, tissue mass spectrometry imaging (tMS1), quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can he performed by protein, gene, and/or tissue array analysis. Typical protocols for evaluating the status of genes and gene products are found, for example in Ausubel et. al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments, the expression levels of one or more erythropoiesis biomarker genes is determined using a method comprising: (a) performing gene expression profiling, PCR (such as rtPCR or qRT-PCR), RNA-sect, microarray analysis, SAGE, MASSARRAY® technique, or FISH on a sample (such as a PBMC or plasma sample from the subject) and b) determining the expression levels of the products of the one or more erythropoiesis biomarker gene in the sample. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. in some embodiments, gene expression is measured by microarray. In some embodiments, gene expression is measured by qRT-PCR. In some embodiments, gene expression is measured by multiplex -PCR. In some embodiments, the erythropoiesis biomarker is transferrin receptor (such as CD71), transferrin, Ly76, CD44, CD235a, ALAS2, or GATA-1.

Methods for the evaluation of niRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like). A quantitative assessment of the gene product prior to translation (e.g. spliced, unspliced or partially spliced mRNA) can be performed in order to evaluate the expression of the corresponding gene(s). Such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled. to generate cDNA probes. The probes are then hybridized to an array of nucleic acids immobilized on a solid support. The array is configured such that the sequence and position of each member of the array is known. For example, a selection of genes associated with erythropoiesis may be arrayed on a solid support. Hybridization of a labeled probe with a particular array member indicates that the sample from which the probe was derived expresses that gene.

The expression level of one or more erythropoiesis biomarker genes can also be determined on the protein level. by taking advantage of immunoagglutination, immunoprecipitation (e.g , immunodiffusion, immunelectrophoresis, immune fixation), immunostaining and/or immunobinding detection techniques (including, e.g., western blotting, in situ immunohistochemistry, in situ immunocytochemistry, immunofluorescence, immunoaffinity chromatography, enzyme immunoassays), and the like. These and further methods of quantifying a particular polypeptide in a mixture may rely on specific binding, e.g., of antibodies, and may be performed in a quantitative manner (e.g., by quantitative histomorphometry of tissue and/or cell samples). Amounts of purified polypeptide may also be determined by physical methods, e.g., photometry or mass spectrometry methods (e.g., tissue mass spectrometry imaging).

In some embodiments, the expression level. of an erythropoiesis biomarker protein in a sample is examined using IHC and staining protocols. IHC staining of tissue sections has been shown to be a reliable method for determining or detecting presence of proteins in a sample. In some embodiments, the erythropoiesis biomarker is detected by immunohistochemistry. In some embodiments, an elevated expression level of an erythropoiesis biomarker in a sample from an individual is elevated protein expression level and, in further embodiments, is determined using IHC. In some embodiments, the expression level of an erythropoiesis biomarker is determined using a method comprising: (a) performing IHC analysis of a sample (such as a PBMC or plasma sample from the subject) with an antibody; and b) determining expression level of the erythropoiesis biomarker gene in the sample. In some embodiments, MC staining intensity is determined relative to a reference. In some embodiments, the reference is a reference value (e.g., from a database of complete responders and partial responders to an immunotherapy). In some embodiments, the erythropoiesis biomarker is transferrin receptor such as CD71) transferrin, Ly76, CD44, CD235a, ALAS2, or GATA-1. In some embodiments, the erythropoiesis biomarker is hemoglobin, erythroid ankyrin, or glycophorin C.

IHC may be performed in combination with additional techniques such as morphological staining and/or fluorescence in-situ hybridization. Two general methods of IHC are available; direct and indirect assays. According, to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification. occurs because several secondary antibodies may react with different epitopes on the primary For use in the detection methods described herein, the skilled person has the ability to label the polypeptides or oligonucleotides encompassed by the present invention. As routinely practiced in the art, hybridization probes for use in detecting mRNA levels and/or antibodies or antibody fragments for use in IHC methods can be labeled and visualized according to standard methods known in the art. Non-limiting examples of commonly used systems include the use of radiolabels, enzyme labels, fluorescent tags, biotin-avidin complexes, chemiluminescence, and the like.

The primary and/or secondary antibodies used for IHC typically will be labeled with a detectable moiety. Numerous labels are available which can be generally grouped into the following categories: (a) Radioisotopes, such as $^{35}S$, $^{14}$, $^{125}I$, $^{3}H$, and $^{131}I$; (b) colloidal gold particles; (c) fluorescent labels including, but not limited to, rare earth chelates (europium thelates), TEXAS RED®, rhodamine, fluorescein, dansyl, Lissamine, umbelliferone, phycocrytherin, phycocyanin, or commercially available fluorophores such SPECTRUM ORANGE™ and SPECTRUM GREEN™ and/or derivatives of any one or more of the above; (d) enzyme-substrate labels including, but not limited to, labels described in U.S. Pat. No. 4,275,149; and (e), enzymatic labels including, for example, luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g , p-nitrophenyl-D-galactosidase) or fluorogenic substrate (e.g., 4-methylumbelliferyl- -D-galactosidase). For a general review of these, see U.S. Pat. Nos. 4,275.149 and 4,318,980.

In some embodiments of any of the methods, expression of one or more erythropoiesis biomarker genes is detected by immunohistochemistry using a diagnostic antibody (i.e., primary antibody) against an erythropoiesis biomarker gene expression product. In some embodiments, the diagnostic antibody specifically binds a product of a human erythropoiesis biomarker gene. In some embodiments, the diagnostic antibody is a nonhuman antibody. In some embodiments, the diagnostic antibody is a rat, mouse, or rabbit antibody. In some embodiments, the diagnostic antibody is a monoclonal antibody. In some embodiments, the diagnostic antibody is directly labeled. In some embodiments, the erythropoiesis biomarker is transferrin receptor (such as CD71), transferrin, Ly76, CD44, CD235a, ALAS2, or GATA-1. In some embodiments, the diagnostic antibody is Ter-119.

IHC samples can be prepared by contacting a sample with any one of the diagnostic antibodies described above, which may be mounted and cover-slipped. Slide evaluation is then determined, e.g., using a microscope, and staining intensity criteria, routinely used in the art, may be employed. In some embodiments, the presence of an erythropoiesis biomarker is detected by IHC in >0% of the sample, in at least 1% of the sample, in at least 5% of the sample, in at least 10% of the sample.

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using, such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding, of a labeled antibody to a target biomarker.

The expression level of an erythropoiesis biomarker gene in a tissue or cell sample may also be examined by way of functional or activity based. assays. For instance, if the biomarker is an enzyme, one may conduct assays known in the art to determine or detect the presence of the given enzymatic activity in the tissue or cell sample.

In some embodiments, the level of a subset of erythroid cells or total erythroid cells is determined using flow cytometry (e.g., FACS), using known methods in the art or methods described herein. Each subset of erythroid cells is characterized by their unique morphology (e.g., cell volume and morphological complexity) and by expression of specific cell surface markers such as CD44, and CD71. Cell volume can be measured using forward scattered light (i.e., "FSC") using flow cytometry. Erythroid cells and subsets thereof can be identified and isolated by flow cytometry using the following gating strategy: total RBCS (Ter-119$^+$ for mice or CD235a$^+$ for human), immature, nucleated RBCs (Ter-119$^+$, CD71$^+$), mature RBCs (Ter-119$^+$/CD235a$^+$, CD71$^+$ or Ter-119$^+$/CD235a$^+$, CD44$^{low}$FSC$^{low}$), proerythroblasts (Ter-119$^+$ for mice or CD235a$^+$ for human), basophilic erythroblasts (Ter-119$^+$/CD235a$^+$, CD44$^{high}$FSC$^{high}$), polychromatic erythroblasts (Ter-119$^+$/CD235a$^+$, CD44$^{intermediate}$FSC$^{intermediate}$), orthochromatic erythroblasts and reticulocytes (Ter-119$^+$/CD235a$^+$, CD44$^{intermediate}$FSC$^{low}$). See, Chen, Liu et. al. 2009, and Koulnis, Pop et. al. 2011.

In certain embodiments, the samples are normalized for both differences in the level of the erythropoiesis biomarker assayed and variability in the quality of the samples used, and variability between assay runs. Such normalization may be accomplished by detecting and incorporating certain normalizing biomarkers, including well known housekeeping genes. Alternatively, normalization can be based on the mean or median signal of all of the assayed genes or a large subset thereof (global normalization approach). On a gene-by-gene basis, measured normalized amount of an mRNA or protein in a subject is compared to the amount found in a reference set or a historical control. Normalized expression levels for each mRNA or protein per tested sample per subject can be expressed as a percentage of the expression level measured in the reference set or historical control. The level measured in a particular subject sample to be analyzed will fall at some percentile within this range, which can be determined by methods well known in the art.

The level of the erythropoiesis biomarker is detected in a sample. A sample typically contains a cell or population of cells, or a quantity of tissue or fluid from a subject. Samples contemplated herein include sections of tissues such as biopsy and autopsy samples, and frozen sections taken for histologic purposes. Biological samples also include blood and blood fractions or products (e.g., serum, plasma, platelets, red blood cells, and the like). A "biopsy" refers to the process of removing a tissue sample for diagnostic or prognostic evaluation and to the tissue specimen itself. Any biopsy technique known in the art can be applied to the diagnostic and prognostic methods of the present invention. The biopsy technique applied will depend on the tissue type to be evaluated (e.g., spleen, bone marrow, blood cell, etc.), among other factors. Representative biopsy techniques include, but are not limited to, excisional biopsy, incisional biopsy, needle biopsy, surgical biopsy, and bone marrow biopsy. Biopsy techniques are discussed, for example, in Harrison's Principles of internal Medicine, Kasper, et. al., eds., 16th ed., 2005, Chapter 70, and throughout Part V.

In some embodiments, the sample is a clinical sample. In some embodiments, the sample is obtained from the spleen of the subject. In some embodiments, the sample is obtained from the bone marrow of the subject. In some embodiments, the tissue sample is formalin fixed and paraffin embedded, archival, fresh or frozen. In some embodiments, the sample is whole blood. In some embodiments, the sample is a blood fraction comprising peripheral blood mononuclear cells (PBMCs). In some embodiments, the sample is a plasma sample or a serum sample.

In some embodiments, a reference sample, reference cell, reference tissue, control sample, control cell, or control tissue is a single sample or combined sample from the same subject or individual that is obtained at one or more different time points than when the test sample is obtained. For example, a reference sample, reference cell, reference tissue, control sample, control cell, or control tissue is a historical control obtained at an earlier time point from the same subject or individual than when the test sample is obtained. Such reference sample, reference cell, reference tissue, control sample, control cell, or control tissue may he useful if the reference sample is obtained before administration of methotrexate and the therapeutic agent to the subject to provide a baseline level of the biomarker in the subject.

In certain embodiments, a reference sample, reference cell, reference tissue, control sample, control cell, or control tissue is a combined sample from one or more healthy individuals who are not the subject or individual to be treated. In some embodiments, a reference sample, reference cell reference tissue, control sample, control cell, or control tissue is a combined sample from one or more individuals with a disease or condition (e.g., Pompe disease) who are not the subject or individual to be treated. In certain embodiments, a reference sample, reference cell, reference tissue, control sample, control cell, or control tissue is pooled samples (e.g. RNA or protein samples) from pooled PBMC or plasma samples from one or more individuals who are not the subject or individual to be treated. In some embodiments, a reference sample, reference cell, reference tissue, control sample, control cell, or control tissue is a combined sample from one or more individuals who are not the subject or individual to be treated but who have induced immune tolerance to the therapeutic agent by methotrexate treatment. In certain embodiments, a reference sample, reference cell, reference tissue, control sample, control cell, or control tissue is pooled samples (e.g. RNA or protein samples) from pooled plasma or PBMC samples from one or more individuals who are not the subject or individual to be treated but who have induced immune tolerance to the therapeutic agent by methotrexate treatment (e.g., a positive control). In certain embodiments, a reference sample, reference cell, reference tissue, control sample, control cell, or control tissue is pooled samples (e.g. RNA or protein samples) from pooled plasma or PBMC samples from one or more individuals who are not the subject or individual and do not display immune tolerance to the therapeutic agent (e.g., a negative control). In some embodiments, a reference sample, reference cell, reference tissue, control sample, control cell, or control tissue is a combined sample from one or more individuals who do not receive the therapeutic agent treatment with methotrexate ("placebo control"). In certain embodiments, a reference sample, reference cell, reference tissue, control sample, control cell, or control tissue is pooled samples (e.g. RNA or protein samples) from pooled PBMC or plasma samples from one or more individuals who do not receive the therapeutic agent treatment with methotrexate ("placebo control"). In some embodiments, the placebo control samples from the one or more individuals have the same disease or disorder (such as Pompe disease) as the subject to be treated.

In some embodiments, the sample is obtained from the subject at least about one day to about 30 days, including about any one off, 1, 2, 4, 7, 9, 14, or 28 days following the last administration of the methotrexate. In some embodiments, the sample is obtained from the subject about 7 days to about 14 days after the last administration of the methotrexate. In some embodiments, the sample is obtained from the subject at least about one day to about 30 days, including about any one of 1, 2, 4, 7, 9, 14, or 28 days following the initial administration of the therapeutic agent. In some embodiments, the sample is obtained from the subject about 7 days to about 14 days after initiation of the therapeutic agent in some embodiments, the sample is obtained from the subject at least about one day to about 30 days, such as about 7, 9 and/or 14 days, after initial administration of methotrexate and the therapeutic agent. In some embodiments, the sample is obtained from the subject about 7 days to about 14 days after initiation of the methotrexate and the therapeutic agent. In some embodiments, the sample is obtained from the subject more than 1 time (such as about any one of 2, 3, 4, or more times). In some embodiments, the sample is obtained on one or more of days 1, 2, 3, 4, 5, 6, 7, 8. 9, 10, 11, 12, 13, 1.4 15, 16, 17, 18, 19, 20, 21, 27, 73, 24, 25, 26, 27, 28, 29, or 30 following methotrexate treatment (e.g., the last methotrexate administration of a cycle of methotrexate treatment). In some embodiments, the sample is obtained from the subject before additional immune tolerance induction therapy and/or immunosuppression therapy is administered to the subject.

B. Therapeutic Agents

The methods described herein are useful for monitoring, assessing, and/or controlling undesirable immune response against the therapeutic agent in the subject. In many cases, undesired immune responses against a. therapeutic agent may cause variable effects on patient outcome. Such responses occur because biologic therapeutics, for example, often contain sequences and conformations that constitute epitopes that are foreign to a human patient. For example, anti-drug antibodies (ADAs) may interfere with therapeutic efficacy and/or increase safety risks. An ADA response may cause hypersensitivity reactions, anaphylaxis, serum sickness, immune complex disease, acute renal failure. ADAs can be monitored in patients receiving protein therapy by a clinician using well established methods, including ELISA and immunohistochemistry.

A variety of therapeutic agents are known to induce undesirable immune responses, which can involve anti-drug antibodies (ADA) and other undesired T- and/or B-cell mediated immune responses. In some embodiments, the therapeutic agent is a biologic, such as a protein, a nucleic acid, a virus, a gene therapy, a lipid, a liposome, a carbohydrate, a metabolite, or a combination thereof.

In some embodiments, the therapeutic agent is a protein therapy. Protein therapy refers to therapy in which the therapeutic agent is a proteinaceous substance, including, peptides or proteins. Protein therapeutics can, for example, be enzymes, cytokines, growth factors, immunomodulators, thrombolytics, antibodies (including polyclonal and monoclonal antibodies), antibody fragments or modified antibodies (e.g., Fab, F(ab')$_2$, Fv, Fd, scFv, and dAb).

In some embodiments, the therapeutic agent is a therapeutic polypeptide. In some embodiments, the therapeutic agent is an enzyme. For example, many enzyme replacement therapies have been developed for patients with certain genetic diseases, including FABRAZYME® (recombinant human alpha-galactosidase) for Fabry disease, CEREZYME® giucerase) for Gaucher disease, ALDURAZYME® (laronidase) for Mucopolysaccharidosis I (MPS I), and MYOZYME® and LUMIZYME® (alglucosidase alfa) for Pompe disease. In some embodiments, the therapeutic agent is human alpha galactosidase A. In some embodiments, the enzyme is human acid α-glucosidase (varyingly termed acid maltase, alpha-glucosidase, alpha-1,4-glucosidase, or acid alpha-1,4-glucosidase). In some embodiments, the enzyme is an enzyme-oligosaccharide conjugate, including an acid alpha-glucosidase-oligosaccharide conjugate or other enzyme-oligosaccharide conjugate as described in U.S. Pat. Nos. 7,001,994; 7,723,296; 7,786,277; 8,399,657; 8,841,427; 9,687,531; 8,759,501; and 9,469,850.

In some embodiments, the therapeutic agent is an enzyme, a neurotrophic factor, a polypeptide that is deficient or mutated in an individual with a CNS-related disorder, an antioxidant, an anti-apoptotic factor, an anti-angiogenic factor, and an anti-inflammatory factor, alpha-synuclein, acid beta-glucosidase (GBA), beta-galactosidase-1 (GLB1), iduronate 2-sulfatase (IDS), galactosylceramidase (GALC), a mannosidase, alpha-D-mannosidase (MAN2B1), beta-mannosidase (MANBA), pseudoarylsulfatase A (ARSA), N-acetylg1icosamine-1-phosphotransferase (GNPTAB), acid sphingomyelinase (ASM), Niemann-Pick C protein (NPC1), acid alpha-1,4-glucosidase (GAA), hexosaminidase beta subunit, HEXB, N-sulfoglucosamine sulfohydrolase (MPS3A), N-alpha-acetylglucosaminidase (NAGLU), heparin acetyl-CoA, alpha-glucosaminidase N-acetyltransferase (MPS3C), N-acetylglucosamine-6-sulfatase (GNS), alpha-N-acetylgalactosaminidase (NAGA), beta-glucuronidase (GUSB), hexosaminidase alpha subunit (HEXA), huntingtin (HTT), lysosomal acid lipase (LIPA), Aspartylglucosaminidase, Alpha-galactosidase A, Palmitoyl protein thioesterase. Tripeptidyl peptidase, Lysosomal transmembrane protein, Cysteine transporter, Acid ceramidase, Acid alpha-L-fucosidase, cathepsin A, alpha-L-iduronidase, Arylsulfatase B, Arylsulfatase A, N-acetylgalaetosamme-6-sulfate, Acid beta-galactosidase, or alpha-neuramidase. In some embodiments, the therapeutic agent is a polypeptide selected from the group consisting of neuronal apoptosis inhibitory protein (NAIP). nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), amino acid decarboxylase (AADC), an anti-oxidant, an anti-angiogenic polypeptide. an anti-inflammatory polypeptide, and aspartoacylase (ASPA).

In some embodiments, the therapeutic agent is Factor VIII (FVIII), Factor IX (FIX), dystrophin, dysferlin and cystic fibrosis transmembrane conductance regulator (CFTR).

In some embodiments, the therapeutic agent is an antibody or antigen binding fragment thereof. Examples of antibody therapeutics include CAMPATH® (alemtuzumab), THYMOGLOBULIN®, AVASTIN® (bevacizumab), LUCENTIS® (ranibizumab), REMICADE® (infliximab), HUMIRA® (adalimumab), RITUXAN® (rituximab), TYSABRI® (natalizumab), SIMULECT® (basiliximab), ZENAPAX® (daclizumab), OKT3® (muromonab-CD3), ERBITUX® (Cetuximab), MYLOTARG® (gemtuzumab), HERCEPTIN® (trastuzumab), and BENLYSTA® (belimumab). Examples of other protein therapeutics include ENBREL® (etanercep), and other fusion proteins In some embodiments, the therapeutic agent is a lymphocyte depleting agent. Lymphocyte depletion is a type of immunosuppression by reduction of circulating lymphocytes, e.g., T cells and or B cells, resulting m lymphopenia. Lymphocyte depletion agents include, for example, THYMOGLOBULIN®, humanized anti-CD52 monoclonal antibody CAMPATH-1H® (alemtuzumab), and rituximab Lymphocyte depletion is desired in treatment of a number of autoimmune conditions, including multiple sclerosis (Coles et. al, Ann Neurol. 46, 296-304 (1999), Coles et al, 2008), rheumatoid arthritis, vasculitis, and lupus. Lymphocyte depletion therapy may cause secondary autoimmunity. Autoimmunity is referred to herein as "secondary autoimmunity" when it arises subsequent to the onset of a first ("primary") disease, for example, a "primary" autoimmune disease. Secondary autoimmunity sometimes arises in MS patients having, or having had, lymphopenia following, e.g., lymphocyte depleting therapy. In some individuals, secondary autoimmunity arises soon after lymphocyte depleting therapy (e.g., treatment with alemtuzumab). In other individuals, secondary autoimmunity may not arise until months or years after lymphocyte depleting, therapy; in some of those individuals, by the time they develop secondary immunity, substantial lymphocyte recovery (total lymphocyte count) may have occurred so that they may no longer be lymphopenic. Lymphocyte depletion may occur in the context of treatment with antibody therapeutics or small molecule therapeutics.

In some instances, the therapeutic agent is a viral therapy where a viral vector is used to deliver a nucleic acid therapeutic. Exemplary viruses used in such therapies include, but are not limited to, adenoviruses, adeno-associated viruses, and retroviruses. Antibodies may develop against the capsid proteins of the virus, reducing the efficacy and increasing the safety risks of such therapies. The methods of the present application are useful to control undesired immunological responses (e.g., ADA responses, and other undesired T- and/or B-cell mediated immune responses) in viral therapies as well. In some embodiments, the viral vector encodes any of the therapeutic agents described herein. In some embodiments, the viral vector encodes an enzyme, a neurotrophic factor, a polypeptide that is deficient or mutated in an individual with a CNS-related disorder, an antioxidant, an anti-apoptotic factor, an anti-angiogenic factor, an anti-inflammatory factor, alpha-synuclein, acid beta-glucosidase (GBA), beta-galactosidase-1 (GLB1), iduronate 2-sulfatase (IDS), galactosylceramidase (GALC), a mannosidase, alpha-D-mannosidase (MAN2B1), beta-mannosidase (MANBA), pseudoarylsulfatase A (ARSA), N-acetylglucosamine-1 phosphotransferase (GNPTAB), acid sphingomyelinase (ASM), Niemann-Pick C protein (NPC1), acid alpha-1,4-glucosidase (GAA, such as alglucosidase alfa), hexosaminidase beta subunit, HEXB. N-sulfoglucosamine sulfohydrolase (MPS3A), N-alpha-acetylglucosaminidase (NAGLU), heparin acetyl-CoA, alpha-glucosaminidase N-acetyltransferase (MPS3C), N-acetylglucosamine-6-sulfatase (GNS), alpha-N-acetylgalactosarninidase (NAGA), beta-glucuronidase (GUSB), hexosaminidase alpha subunit (HEXA), huntingtin (HTT), lysosomal acid lipase (LIPA), Aspartylglucosaminidase, Alpha-galactosidase A, Palmitoyl protein thioesterase, Triptidyl peptidase, Lysosomal transmembrane protein, Cysteine transporter, Acid ceramidase, Acid alpha-L-fucosidase, cathepsin A, alpha-L-iduronidase, Arylsulfatase B, Arylsulfatase A, N-acetylgalactosamine-6-sulfate, Acid beta-galactosidase, or alpha-neuramidase. In some embodiments, the viral vector encodes a polypeptide selected from the group consisting of neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP cyclohydrolase (GTPCH), amino acid decarboxylase (AADC) , an anti-oxidant, an antiangiogenic polypeptide, are anti-inflammatory polypeptide, and aspartoacylase (ASPA). In some embodiments, the viral vector encodes Factor VIII (FVIII), Factor IX (FIX), dystrophin, dysferlin or cystic fibrosis transmembrane conductance regulator (CFTR). In some embodiments, the viral vector encodes an antibody or antigen binding fragment thereof. Examples of antibody therapeutics include CAMPATH® (alemtuzumab), THYMOGLOBULIN®, AVASTIN® (bevacizumab), LUCENTIS® (ranibizumab), REMICADE® (infliximab), HUMIRA® (adalimumab), RITUXAN® (rituximab), TYSABRI® (natalizumab), SIMULECT® (basiliximab), ZENAPAX® (daclizumab), OKT3® (muromonab-CD3), ERBITUX® (Cetuximab), MYLOTARG® (gemtuzumab), HERCEPTIN® (trastuzumab), and BENLYSTA® (belimumab). In some embodiments, the viral vector encodes a fusion protein, for example, ENBREL® (etanercep).

The methods of the present application may also be used to control undesired immunological responses in non-protein biological therapies. Exemplary non-protein bio-therapies include, but are not limited to, nucleic acid therapies, (e.g., antisense therapies, siRNA therapies, and miRNA therapies).

C. Methotrexate, Other Immune Tolerance Induction Therapies, and Immunosuppression Therapies The methods described herein comprise administering to a subject an effective amount of methotrexate. In. some embodiments, the methotrexate is used to induce immune tolerance to the therapeutic agent in the subject. Any of the available dosing regimens can be used to induce immune tolerance, including continuous weekly repeat doses regimen (Garman et. al. Clin Exp Immunol, 137(3).496-502 (2004); Joseph et al, Clin Exp Immunol, 152(1): 138-46 (2008); Mendelsohn et al, N Engl J Med, 360(2): 194-5 (2009)), and transient low-dose regimens (See U.S. Patent Publication No. 20140135337). In some embodiments, the effective amount of methotrexate is administered in three cycles. In some embodiments, the methotrexate is administered in a single cycle. In some embodiments, the methotrexate is administered in one, two, three, four, five or more cycles.

The use of transient low-dose methotrexate for induction of immune tolerance is unique from its well-acknowledged role as a chemotherapeutic agent or as a continuous immunosuppressive agent in rheumatologic diseases (Kremer 2004). Methotrexate was first described for the treatment of cancer during the 1940's, and high-dose courses of methotrexate continue to be prescribed to treat a number of cancers and neoplasms. For autoimmune disorders, continuous weekly low-dose methotrexate is used to treat rheumatoid arthritis and psoriasis, among others (Cronstein 2005; Taylor et. al., 2008). In transient low-dose methotrexate regimens, a single cycle or three cycles of low-dose methotrexate is administered concurrently with initiation of a biologic therapy. In some embodiments, one cycle is equivalent to 3 consecutive daily doses of low-dose methotrexate dosed at 0, 24 and 48 hours. Although originally designed as a three cycle regimen, a single cycle of low-dose methotrexate has been demonstrated in mice to be just as effective in providing long-lived immune tolerance (Joseph, Neff et. al. 2012, Joly, Martin et. al. 2014).

Methotrexate functions as a folate antagonist that competitively inhibits the dihydrofolate reductase that is essential for the de novo synthesis of the nucleoside thymidine and biosynthesis of purines and pyrimidines. As DNA synthesis is critically important for cell cycling, high-dose methotrexate is thought to treat cancer by killing highly-proliferating cells. In contrast, the mechanism by which continuous, weekly low-dose methotrexate is thought to control autoimmune disorders is believed to be due to effects on purine metabolism that lead to depletion of T cells or inhibition of antigen-dependent T cell proliferation (Cronstein 2005). Also, methotrexate has been shown to induce the accumulation of the anti-inflammatory mediator adenosine which can mediate T regulatory cells in inflammatory disorders (Cronstein 2005, Ernst, Garrison et. al. 2010, Han, Thomas et. al. 2013).

The mechanism by which immune tolerance is achieved by transient low-dose methotrexate treatment in mice appears to be different from that of immune suppression through continuous weekly repeat doses of methotrexate. Weekly repeat doses of methotrexate may have different immunological consequences when compared to the transient dosing regimen.

As used herein, a single cycle refers to a treatment regimen, or a treatment unit, of consecutive or non-consecutive days and is started at preferably no more than five (e,g., no more than three) days following the dosing, of the therapeutic agent. A single cycle of methotrexate may consist of a single dose of methotrexate, or about any one of 2, 3, 4, 5, 6, 7, 8, 9, 10, or 11 consecutive daily doses of methotrexate. If the therapeutic agent is dosed in multiple periods, a single cycle of treatment with methotrexate preferably does not extend past the first period of the therapeutic agent dosing. By way of example, in a weekly, monthly, or annual therapeutic agent, a single cycle of methotrexate consists of three consecutive days of methotrexate intake (e.g., orally), starting on day 0, the day when the therapeutic agent is given to the patient for the first time. Then the patient receives a single dose of methotrexate on day 1 (about 24 hours later) and on day 2 (about 48 hours later). In some embodiments, a single cycle of methotrexate does not last longer than about 8 days.

Methotrexate and the therapeutic agent can be administered in any order deemed appropriate. For example, the methotrexate can be administered to the subject before, during, and/or after administration of the therapeutic agent. In some embodiments, the methotrexate is administered between about 48 hours prior to and about 48 hours after the administration of the therapeutic agent treatment. For example, the methotrexate may be administered about any one of 48 hours prior to, 36 hours prior to, 24 hours prior to, 12 hours prior to, concurrently with, 12 hours after, 24 hours after. 36 hours after, or 48 hours after the administration of the therapeutic agent treatment. In some embodiments, the methotrexate is administered concurrently with the therapeutic agent. In some embodiments, the methotrexate is administered concurrently with administration of the therapeutic agent, and about 24 and about 48 hours after administration of the therapeutic agent. In some embodiments, the therapeutic agent is alglucosidase alfa, and the methotrexate is administered concurrently with administration of the therapeutic agent and about 24 and about 48 hours after administration of the therapeutic agent.

Methotrexate can be administered at any dose effective in reducing undesired immunological responses, such as antibody or cellular responses. An effective amount of methotrexate in human patients may be in the range of about 0.05 mg/kg to about 10 mg/kg, such as no more than about any one of 0.1 mg/kg, 0.2 mg/kg, 0.3 mg/kg, 0.4 mg/kg, 0.5 mg/kg, 1 mg/kg, 1.5 mg/kg, 2 mg/kg, 2.5 mg/kg, 3 mg,/kg, 3.5 mg/kg, 4 mg/kg, 4.5 mg/kg, 5 mg/kg, 6 mg/kg, 7.5 mg/kg, or 10 mg/kg. In some embodiments, the effective amount is any one of about 0.1 mg/kg to about 1.5 mg/kg, about 0.12 mg/kg to about 1.28 mg/kg, about 1 mg/kg to about 2.5 mg/kg, or about 2.5 mg/kg to about 5 mg/kg, or about 0.1 mg/kg to about 5 mg/kg,. In some embodiments, the dosage of methotrexate may pose minimal safety risks because the dosing regimen involves only a brief course of methotrexate at dose levels that are more similar to doses for rheumatoid arthritis than low neoplastic doses. Rheumatoid arthritis patients can receive up to 25 mg, of methotrexate per week without suffering from significant toxicities. The low neoplastic dose of methotrexate is considered to be 30 mg/m$^2$.

In some embodiments, methotrexate is administered in more than one cycle, but at a low total dosage. For instance, the methotrexate can be administered in two or more (e.g., 3, 4, 5, 6, etc.) cycles, but with a total combined dosage of no more than 5 mg/kg in a patient.

The low-dose regimens of methotrexate are likely to be well-tolerated in adults. The exact dosage and regimen of methotrexate should be established by a clinician, taking into account the patient's physical condition, age, weight, gender, other medications he/she is taking and their known side-effects, and any other relevant factors.

In some embodiments, in addition to methotrexate, the subject is administered an initial immune tolerance induction therapy concurrently with the administration of the therapeutic agent. As referred herein, "initial immune tolerance induction therapy" refers to immune tolerance induction regimen administered to the subject upon initiation of the therapeutic agent as opposed to immune tolerance induction therapy administered in further cycles of treatment with the therapeutic agent. In some embodiments, the initial immune tolerance induction therapy is administered concurrently with methotrexate. In some embodiments, the initial immune tolerance induction therapy is administered after administration of methotrexate, such as after any one of 1, 2, 3, 4, 5, 6, 7 days or more after administration of methotrexate. In some embodiments, the initial immune tolerance induction therapy is administered before administration of methotrexate, such as any one of 1, 2, 3, 4, 5, 6, 7 days or more before administration of methotrexate. In some embodiments, the subject has Pompe disease, such as CRIM-negative Pompe disease, and/or infantile-onset Pompe disease (e.g., classic infantile-onset Pompe disease). In some embodiments, methotrexate is administered enterally. In some embodiments, methotrexate is administered at a dose of about 0.5 mg/kg. In some embodiments, methotrexate is administered weekly. In some embodiments, methotrexate is administered subcutaneously. In some embodiments, methotrexate is administered at a dose of about 0.4 mg/kg. In some embodiments, methotrexate is administered at three doses per week for three weeks.

In some embodiments, the initial immune tolerance induction therapy comprises rituximab, IVIG, or combination thereof. In some embodiments, the initial immune tolerance induction therapy comprises administration of rituximab. In some embodiments, rituximab is administered at a dose of about 375 mg/m$^2$. In some embodiments, such as when the body surface area (BSA) of the subject is less than 0.5 in rituximab is administered at a dose of about 12.5 mg/kg. In some embodiments, rituximab is administered intravenously. In some embodiments, rituximab is administered weekly. In some embodiments, the initial immune tolerance induction therapy comprises administration of IVIG. In some embodiments, IVIG is administered at a dose of about 0.5 g/kg. In some embodiments, IVIG is administered at a dose of about 400-500 mg/kg. In some embodiments, IVIG is administered about every four weeks. In some embodiments, IVIG is administered monthly. In some embodiments. the initial immune tolerance induction therapy comprises administration of both rituximab and IVIG.

In some embodiments, the subject is administered further treatment with the therapeutic agent based on the level of one or more erythropoiesis biomarkers. In some embodiments, wherein the levels of the one or more erythropoiesis biomarkers are elevated with respect to those in a control, the subject is administered further treatment with the therapeutic agent without administering additional immune tolerance induction therapy or immunosuppression therapy. In some embodiments, wherein the levels of the one or more erythropoiesis biomarkers are reduced with respect to those in a control, the subject is administered further treatment with the therapeutic agent concurrently with administration of additional immune tolerance induction therapy and/or immunosuppression therapy. In some embodiments, the one or more erythropoiesis biomarkers comprise immature nucleated red blood cells. In some embodiments, the one or more erythropoiesis biomarkers comprise a gene associated with erythropoiesis, wherein the gene is associated with one or more of hemopoiesis, iron ion homeostasis, regulation of erythrocyte differentiation, and heine metabolism. In some embodiments, the one or More erythropoiesis biomarkers comprise a gene encoding transferrin receptor (such as CD71), transferrin, CD44, CD235a, ALAS2, or GATA-1. In some embodiments, the one or More erythropoiesis biomarkers are detected in a sample obtained from the subject about 7 days to about 14 days following the last administration of the methotrexate. in some embodiments, the sample is a blood sample, a PBMC sample, or plasma sample.

In some embodiments, wherein the levels of the one or more erythropoiesis biomarkers are approximately equal to (such as at least about any one of 90%, 95%, 98%, 99%, or more) or less than (i.e., reduced with respect to) those in a control, the subject is administered further treatment with the therapeutic agent without administering additional immune tolerance induction therapy or immunosuppression therapy. In some embodiments, wherein the levels of the one or more erythropoiesis biomarkers are elevated with respect to those in a control, the subject is administered further treatment with the therapeutic agent concurrently with administration of additional immune tolerance induction therapy and/or immunosuppression therapy. In some embodiments, the one or more erythropoiesis biomarkers comprise mature red blood cells. In some embodiments, the one or more erythropoiesis biomarkers comprise total erythroid cells. In some embodiments, the one or more erythropoiesis biomarkers comprise hemoglobin, erythroid ankyrin, or glycophorin C. In some embodiments, the one or more erythropoiesis biomarkers are detected in a sample obtained from the subject about one day to about 30 days (such as about 7 days to about 14 days) following the last administration of the methotrexate. In some embodiments, the sample is a blood sample, a PBMC sample, or plasma sample.

Any of the known immune tolerance induction therapies and/or immunosuppression therapies in the art may be administered to the subject in conjunction with further treatment with the therapeutic agent. In some embodiments, the additional immune tolerance induction therapy or immunosuppression therapy comprises a small molecule therapeutic agent, a protein therapeutic agent, or combinations thereof. Exemplary immunosuppression agents include, but are not limited to, an anti-CD20 antibody (e.g., rituximab), an anti-BAFF antibody (e.g., belimumab), an anti-CD3 antibody (e.g., muromonab or otelixizumab), an anti-CD19 antibody, an antiCD22 antibody, an anti-IgE antibody (e.g., omalizumab), a corticosteroid (e.g. Prednisolone), rapamycin, methotrexate, IVIG, cyclophosphamide, cyclosporine A, azathioprine, mycophenolate mofetil, and a proteasome inhibitor (e.g., bortezomib). These additional it odulating agents or their derivatives include agents targeting/altering antigen presentation and/or humoral or cell mediated immune response. In some embodiments, the additional immune tolerance induction therapy or immunosuppression therapy comprises administration of intravenous gamma globulin (IVIG). In some embodiments, the immunosuppression therapy comprises a lymphocyte-depleting agent that depletes T-cells, B-cells and/or plasma cells. In some embodiments, the agent that depletes plasma cells is bortezomib.

In some embodiments, the additional immune tolerance induction therapy or immunosuppression therapy comprises an antigen-specific tolerance strategy. Various antigen-specific tolerance therapies have been developed by using, for example, antigen peptides, antigen- or peptide-coupled cells, altered-peptide ligands (APLs), and derivatives thereof. Antigen-specific tolerance therapies have been described, for example, in Miller et. al. *Nature Reviews Immunology* 7.9 (2007): 665-677. In some embodiments, the antigenspecific tolerance therapy comprises administering more frequent doses of the therapeutic agent or a higher dose of the therapeutic agent, or both. For example, the therapeutic agent can be administered at a dose that is at least about any one of 1.5×, 2×, 3×, 5×, 10× or more than the initial dose. In some embodiments, the therapeutic agent is administered at a frequency that is at least about any one of 1.5×, 2×, 3×, 5×, or higher than the initial frequency. In some embodiments, the higher dose of the therapeutic agent is administered concomitantly with IVIG.

In some embodiments, the additional immune tolerance induction therapy or immunosuppression therapy comprises administration of methotrexate. In some embodiments, the additional immune tolerance induction therapy or immunosuppression therapy does not comprise administration of methotrexate. In some embodiments, the additional immune tolerance induction therapy or immunosuppression therapy comprises one or more of: administering an effective amount of one or more of rituximab, intravenous immunoglobulin (IVIG), cyclophosphamide, bortezomib, azathioprine, cyclosporine, mycophenolate, and a corticosteroid; and administration of an antigen-specific tolerance strategy.

The additional immune tolerance induction therapy or immunosuppression therapy may be administered to the subject prior to further administration of the therapeutic agent, or concurrently with further administration of the therapeutic agent. In some embodiments, the further treatment with the therapeutic agent lasts at least about any one of 1 month, 2 months, 3 months, 6 months, 1 year, 2 years, 3 years or more. The additional immune tolerance induction therapy or immunosuppression therapy may be administered for the entire duration of further treatment of the therapeutic agent, or for a part (such as only the beginning) of the further treatment. Different types and/or regimens of additional immune tolerance induction therapy and/or immunosuppression therapy may be administered for each cycle of treatment with the therapeutic agent. The dosing regimen and duration of the treatment of the additional immune tolerance induction therapy or immunosuppression therapy may be selected by a physician based on disease progression, levels of anti-drug antibodies, and/or the levels of one or more erythropoiesis biomarkers.

The effect of methotrexate and optionally other immune tolerance induction therapy and immunosuppression therapy on managing undesired antibody responses in the patient can be monitored by well-known methods, including clinical examination of the patient, symptoms, blood tests assaying anti-drug, antibody titers, and immunohistochemical assays (e.g., C4 deposition assays and other solid-phase antibody detection methods such as the enzyme-linked immunosorbent assay (ELISA) and bead-based flurometric assays). The effect also can be monitored by measuring levels of biomarkers such as MCP-1, IL-13, IL-6, and IL-12, whose levels have been shown to be reduced. by methotrexate treatment, and transitional 2 B cells, transitional 3 B cells, follicular B cells, marginal zone B cells, B10 B cells, and B1 B cells, whose numbers have been shown to be increased by methotrexate treatment. Additionally, TGF-beta, FoxP3, IL-5, IL-10, IL-15, and GM-CSF may be used as biomarkers to monitor the effects of methotrexate on undesired immune responses as needed. The levels of biomarkers also may be used to monitor the effects of methotrexate on T cell responsiveness to a therapeutic agent (e.g., a therapeutic polypeptide). Biomarkers for T cell activation such as IL-2, interferon-γ, and TNF-α, may also be monitored as readouts for m.elhotrexate's effect on T cell responses. In some embodiments, the level of CD19 is further detected to monitor undesirable immune response. In some embodiments, the subject is monitored throughout the treatment for one or more of anti-drug antibody level. (such as anti-rhGAA IgG antibody CD19 level, and disease progression.

D. Diseases and Conditions

The methods described herein are useful for treating subjects having a disease or condition that can be treated by a therapeutic agent, such as a protein therapeutic agent. For example, enzyme replacement therapy has been developed to treat many diseases and conditions, but undesirable immune response, such as antidrug antibodies, can develop in subjects receiving the enzyme replacement therapy.

In some embodiment, the subject has a lysosomal storage disease. Lysosomal storage disease describes a class of over 40 genetic disorders (see, e.g., Holton, J. B., THE INHERITED METABOLIC DISEASES 205-242 (2nd ed. 1994); Scriver et. al., 2 THE METABOLIC BASIS OF INHERITED DISEASE (7th ed. 1995)), each resulting, from a deficiency of a particular lysosomal enzyme, usually as a result of genetic mutation. Lysosomal enzymes are required to break down protein, glycolipid and carbohydrate metabolites within the lysosomes of cells. When one or more of these enzymes are defective in affected individuals due to inherited mutations, lysosomes in cells of affected individuals accumulate a subset of undigested substrates, largely liposaccharides and. carbohydrates, as storage materials that are unable to be digested by the defective enzymes. For example, in Gaucher disease, deficiency of beta-glucocerebrosidase causes the accumulation of glucosylceramide; in Fabry disease, the defective alpha-galactosidase A results in accumulation of globotriaosylceremide; in Pompe disease, lack of acid alpha-glucosidase causes accumulation of glycogen alpha-1-4 linked oligosaccharides; and in Tay-Sachs disease, deficiency of beta-N-acetyl-hexosaminidase leads to accumulation of GM2 ganglioside. Clinically, patients with these syndromes show a variety of symptoms associated with the accumulation of these storage material in the lysosomes, which eventually affect the normal function of the cells or tissues that result in dysfunction of organs within the human body. The severity of the disease varies with the residual enzyme activity in severe cases in which there is little or no enzyme activity, death can occur early in life.

In some embodiments, the subject has Gaucher disease and is in need of treatment with beta-glucocerebrosidase. In some embodiments, the subject has Fabry disease a.n.d is in need of treatment with alpha-galactosidase A. In some embodiments, the subject has Tay-Sachs disease, and is in need of beta-N-acetyl-hexosaminidase. In some embodiments, the subject has Pompe disease and is in need of acid α-glucosidase.

In some embodiments, the subject has Pompe disease (varyingly known as acid maltase deficiency and glycogen storage disease type II). The methods described herein are effective for subjects with both early onset (infantile) and late onset (juvenile and adult) Pompe disease. In some embodiments, the subject has genetically inherited Pompe disease. In some embodiments, the subject has infantile-onset Pompe disease. In some embodiments, the subject has non-classic infantile-onset Pompe disease. In some embodiments, the subject has late-onset Pompe disease, such as childhood-, juvenile-, or adult-onset Pompe disease. In some embodiments, the subject has an adult-onset form of Pompe disease.

Classic infantile-onset Pompe disease begins within a few months of birth. Infants with this disorder typically experience muscle weakness (myopathy), poor muscle tone (hypotonia), an enlarged liver (hepatomegaly), and heart defects including cardiac hypertrophy, in association with glycogen storage in all organs. Affected infants may also fail to gain weight and grow at the expected rate (failure to thrive) and have breathing problems. On clinical examination, there is generalized hypotonia with muscle wasting, increased respiration rate with sternal retractions, moderate enlargement of the liver, and protrusion of the tongue. Ultrasound examination of the heart shows a progressive hypertrophic cardiomyopathy, eventually leading to insufficient cardiac output. The ECG is characterized by marked left axis deviation, a short PR interval, large QRS complexes, inverted T waves and ST depression. The disease shows a rapidly progressive course leading to cardiorespiratory failure within the first year of life. On histological examination at autopsy, lysosomal glycogen storage is observed in various tissues and is most pronounced in heart and skeletal muscle. if untreated, this form of Pompe disease generally leads to death from heart failure within the first year of life.

Non-classic infantile-onset Pompe disease usually appears by age 1. It is characterized by delayed motor skills (such as rolling over and sitting) and progressive muscle weakness. The heart may be abnormally large (cardiomegaly), but affected individuals usually do not experience heart failure. The muscle weakness in this disorder leads to serious breathing problems, and if untreated, most children with non-classic infantile-onset Pompe disease live only into early childhood.

Late-onset Pompe disease may not become apparent until later m childhood, adolescence, or adulthood. Late-onset Pompe disease is usually milder than the infantile-onset forms of this disorder and is less likely to involve the heart. Most individuals with late-onset Pompe disease experience progressive muscle weakness, especially in the legs and the trunk, including the muscles that control breathing. As the disorder progresses, breathing problems can lead to respiratory failure.

Treatment with human acid alpha glucosidase can prolong the life of such patients (e.g, to greater than 1, 2, or 5 years up to a normal lifespan). Treatment can also eliminate or reduce clinical and biochemical characteristics of Pompe disease, as discussed above. Treatment is administered soon after birth, or antenatally if the parents are known to bear variant alpha glucosidase alleles placing their progeny at risk.

Patients with the late-onset adult form of Pompe disease may not experience symptoms within the first two decades of life. In this clinical subtype, effects on skeletal muscle are predominant, particularly in muscles of the limb girdle, the trunk and the diaphragm. Difficulty in climbing stairs is often the initial complaint. The respiratory impairment varies considerably. It can dominate the clinical picture, or the patient may not experience it until late in life. Most late-onset patients ultimately die because of respiratory insufficiency. In patients with the juvenile subtype, symptoms usually become apparent in the first decade of life. As in adult Pompe disease, skeletal muscle weakness is the major problem; cardiomegaly, hepatomegaly, and macroglossia can be seen, but are rare. In many cases, nightly ventilatory support is ultimately needed. Pulmonary infections, in combination with wasting of the respiratory muscles, are life threatening and generally become fatal before the third decade of life. Treatment with the present methods prolongs the life of patients with juvenile or adult late-onset Pompe disease up to a normal life span. Treatment also eliminates or significantly reduces clinical and biochemical symptoms of disease.

In some embodiments, the subject having Pompe disease is CRIM-negative. As used herein in the context of Pompe disease, "CRIM" refers to immunoreactivity of a patient's endogenous GAA protein. For example, patients with two deleterious mutations and complete absence of GAA, as assessed by western blot using an antibody against wildtype human GAA protein, are classified as cross-reactive immunologic material (CRIM)-negative. Patients with GAA protein detectable by western blot are classified as CRIM-positive. Whereas the majority of CRIM-positive patients have sustained therapeutic responses to ERT, CRIM-negative patients almost uniformly fare poorly, experiencing rapid clinical decline because of the development of sustained, high-titer antibodies to rhGAA. See, Kishnani. P S, et. al. Mol Genet Metab. 2010; 99:26-33. This ADA has also been observed in some CRIM-positive patients (Banugaria et. al. 2011). In some embodiments, the CRIM status is identified through GAA mutation analysis with or without confirmation by western blot analysis of skin fibroblast cells.

In some embodiments, the subject has an autoimmune disease, such as multiple sclerosis (MS). In some embodiments, the subject is in need of treatment with an anti-CD52 antibody. in some embodiments, this antibody is aletrituzumab.

In some embodiments, the subject has a genetic disease. In some embodiments, the subject has a disease or disorder that is treated by administration of a biologic (e.g., a polypeptide, nucleic acid, etc.). In some cases, the subject has a disease or disorder that is treated with a compound (e.g., a biologic) which may induce an anti-drug antibody (ADA) response or immune response. In some embodiments, the subject has hemophilia A, hemophilia B, muscular dystrophy, cystic fibrosis, Huntington's disease, Parkinson's disease, or Alzheimer's disease. In some embodiments, the subject has a disease or disorder that is treated with a viral therapy wherein a viral vector is used to deliver a nucleic acid. In some embodiments, the viral vector is derived from a retrovirus, an adenovirus, a lentivirus, a herpes simplex, a vaccinia or an adeno-associated virus.

III. Kits, Assays and Articles of Manufacture

Further provided herein are kits comprising one or more reagents for detecting an erythropoiesis biomarker in a sample obtained from a subject after administration of methotrexate and a therapeutic agent. In some embodiments, the kit further comprises a therapeutic agent and/or methotrexate. In some embodiments, the kit further comprises additional immune tolerance induction therapy or immunosuppression therapy. In some embodiments, the kit further comprises instructions to use the kit to select a medicament (e. g. additional immune tolerance induction therapy or immunosuppression therapy) for treating the disease or disorder if the individual has reduced level of the erythropoiesis biomarker. In some embodiments, the kit comprises reagents for detecting two or more erythropoiesis biomarkers.

In some embodiments, there is provided an assay for assessing the level of immune tolerance to a therapeutic agent (such as human acid α-glucosidase) in a subject with Pompe disease, the method comprising: obtaining a sample from the subject, wherein the subject has previously been administered at least one cycle of methotrexate treatment and at least one dose of the therapeutic; and contacting the sample with an agent that binds to an erythropoiesis biomarker, wherein detection of an elevated level of the erythropoiesis biomarker with respect to the level of a. control indicates an induction of immune tolerance.

In some embodiments, there is provided an assay for assessing the level of immune tolerance to a therapeutic agent in a subject in need of the therapeutic, comprising: (a) administering to the subject an effective amount of methotrexate; (b) administering to the subject a therapeutically effective amount of the therapeutic agent; and (c) detecting an erythropoiesis biomarker in a sample obtained from the subject, wherein a level of the erythropoiesis biomarker in the sample with respect to the level of a control indicates induction of immune tolerance in the subject to the therapeutic agent. In some embodiments, the erythropoiesis biomarker is detected in a sample obtained from the subject at least one day to about 30 days after administration of methotrexate. In some embodiments, a change in the level of the erythropoiesis biomarker is associated with induction of erythropoiesis. wherein a change in the level of the erythropoiesis biomarker is associated with induction of erythropoiesis. In some embodiments, if the level of the erythropoiesis biomarker is approximately equal to or less than that of a control, the subject is in need of additional immune tolerance induction therapy or immunosuppression therapy concurrently with further treatment with the therapeutic agent; or if the level of the erythropoiesis biomarker is elevated with respect to that of a control, the subject is not in need of additional immune tolerance induction therapy or immunosuppression therapy. In some embodiments, if the level of the erythropoiesis biomarker is approximately elevated with respect to that of a control, the subject is in need of additional immune tolerance induction therapy or immunosuppression therapy concurrently with further treatment with the therapeutic agent; or wherein if the level of the erythropoiesis biomarker is equal to or less than that of a control, the subject is not in need of additional immune tolerance induction therapy or immunosuppression therapy.

Provided herein are also articles of manufacture comprising, packaged together, a pharmaceutical composition comprising a therapeutic agent (such as human acid α-glucosidase). a pharmaceutical composition comprising methotrexate and a package insert indicating that the therapeutic agent is for treating a patient with a disease or Condition based on the level of an erythropoiesis biomarker after administration of the therapeutic agent and methotrexate. In some embodiments, the article of manufacture further comprises additional immune tolerance induction therapy and/or immunosuppression therapy. Treatment methods include any of the treatment methods disclosed herein.

The article of manufacture comprises a container and a label or package insert on or associated with the container. Suitable containers include, for example, bodies, vials, syringes, etc. The containers may be formed from a variety of materials such as glass or plastic. The container holds or contains a composition comprising the therapeutic agent as the active agent and may have a sterile access port (for example the container may be an intravenous solution bag or a vial having a stopper pierceable by a hypodermic injection needle).

The article of manufacture may further comprise a second container comprising a pharmaceutically-acceptable diluent buffer, such as bacteriostatic water for injection (BWFI), phosphate buffered saline, Ringer's solution and dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating a disease or condition based on the level of one or more erythropoiesis biomarkers described herein. The insert or label may take any form, such as paper or on electronic media such as a data storage device that includes flash memory (such as a USB flash drive or the like), a magnetically recorded medium (e,g., floppy disk), or a CD-ROM. The label or insert may also include other information concerning the pharmaceutical compositions and dosage forms in the kit or article of manufacture.

The invention also concerns a method for manufacturing an article of manufacture comprising combining in a package a pharmaceutical composition comprising a therapeutic agent (such as human acid α-glucosidase), a pharmaceutical composition comprising methotrexate, and a package insert indicating that the therapeutic agent is for treating a patient with a disease or condition (such as Pompe disease) based on the level of an erythropoiesis biomarker after administration of the therapeutic agent and methotrexate. In some embodiments, the article of manufacture further comprises additional immune tolerance induction therapy and/or immunosuppression therapy.

IV. Exemplary Embodiments

The invention provides the following embodiments:

Embodiment 1. A method for treating a subject in need of treatment with a therapeutic agent, comprising: (a) administering to the subject an effective amount of methotrexate; (b) administering to the subject an effective amount of the therapeutic agent, (c) detecting an erythropoiesis biomarker in a sample obtained from the subject between at least one day and about 30 days after administration of methotrexate; and (d) continuing further treatment with the therapeutic agent with or without administering additional immune tolerance induction therapy or immunosuppression therapy based on a level of the erythropoiesis biomarker compared to that of a control.

Embodiment 2. The method of embodiment 1, wherein a change in the level of the erythropoiesis biomarker is associated with induction of erythropoiesis.

Embodiment 3. The method of embodiment 2, wherein if the level of the erythropoiesis biomarker is approximately equal to or less than that of a control, step (d) comprises administering the additional immune tolerance induction therapy or the immunosuppression therapy concurrently with further treatment with the therapeutic agent; or wherein if the level of the erythropoiesis biomarker is elevated with respect to that of a control, step (d) comprises continuing further treatment with the therapeutic agent without administering the additional immune tolerance induction therapy or the immunosuppression therapy.

Embodiment 4. The method of embodiment 2, wherein if the level of the erythropoiesis biomarker is approximately elevated with respect to that of a control, step (d) comprises administering the additional immune tolerance induction therapy or the immunosuppression therapy concurrently with further treatment with the therapeutic agent; or wherein if the level of the erythropoiesis biomarker is equal to or less than that of a control, step (d) comprises continuing further treatment with the therapeutic agent without administering the additional immune tolerance induction therapy or the immunosuppression therapy, Embodiment 5. The method of embodiment 3, wherein the erythropoiesis biomarker is the level of immature nucleated red blood cells, immature reticulocyte fraction, or cellular nucleic acid contents.

Embodiment 6. The method of embodiment 4, wherein the erythropoiesis biomarker is hematocrit.

Embodiment 7. The method of embodiment 5, wherein if the level of immature nucleated red blood cells initially decreases before the level of immature nucleated red blood cells is elevated, further treatment with the therapeutic agent is continued without administering the additional immune tolerance induction therapy or the immunosuppression therapy.

Embodiment 8. The method of embodiment 7, wherein the methotrexate is administered in a single cycle, wherein the level of immature nucleated red blood cells decreases by about one, about two, about three, about four, about five, about six, or about seven days before the level of immature nucleated red blood cells becomes elevated.

Embodiment 9. The method of embodiment 7, wherein the methotrexate is administered in two or more cycles, wherein the level of immature nucleated red blood cells decreases by about one to about 14 days before the level of immature nucleated red blood cells becomes elevated.

Embodiment 10. The method of embodiment 3 or 4, wherein the detecting the erythropoiesis biomarker is detecting the expression of a gene associated with erythropoiesis, wherein the gene associated with erythropoiesis is a gene associated with one or more of hemopoiesis, iron ion homeostasis, regulation of erythrocyte differentiation, and heme metabolism.

Embodiment 11. The method of embodiment 10, wherein the gene associated with erythropoiesis is a gene encoding transferrin receptor, transferrin, Ly76 (antigen for Ter-119), CD44, CD235a, ALAS2, or GATA-1.

Embodiment 12. The method for embodiment 11, wherein the transferrin receptor is transferrin receptor 1 (CD71).

Embodiment 13. The method of any one of embodiments 10-12, wherein detecting the gene associated with erythropoiesis comprises detecting an RNA transcript of the gene associated with erythropoiesis or detecting a protein product of the gene associated with erythropoiesis.

Embodiment 14. The method of embodiment 13, wherein the protein product is hemoglobin.

Embodiment 15. The method of embodiment 3, wherein the erythropoiesis biomarker is a co-factor associated with erythropoiesis.

Embodiment 16. The method of embodiment 15, wherein the co-factor associated with erythropoiesis is porphyrin, a porphyrin-containing compound, or a tetrapyrrole.

Embodiment 17. The method of any one of embodiments 1-16, wherein the sample is a blood sample.

Embodiment 18. The method of embodiment 17, wherein the blood sample is a blood fraction comprising peripheral blood mononuclear cells (PBMC).

Embodiment 19. The method of embodiment 18, wherein the blood sample is a serum sample or a plasma sample and detecting the biomarker is detecting the expression of a gene associated with erythropoiesis.

Embodiment 20. The method of any one of embodiments 1-19, wherein the control is a historical control or a placebo control.

Embodiment 21. The method of any one of embodiments 1-20, wherein the subject is human.

Embodiment 22. The method of any one of embodiments 1-21, wherein the effective amount of methotrexate is administered in a single cycle or in three cycles.

Embodiment 23. The method of embodiment 22, wherein the methotrexate is administered in a single cycle.

Embodiment 24. The method of embodiment 22 or embodiment 23, wherein a cycle of methotrexate consists of 1 day of methotrexate administration or 2, 3, 4, 5, 6, 7, 8, 9, 10, or 11 consecutive days of methotrexate administration.

Embodiment 25. The method of any one of embodiments 1-24, wherein the methotrexate is administered to the subject at a time selected from one or more of before, during, and after administration of the therapeutic agent.

Embodiment 26. The method of embodiment 25, wherein the methotrexate is administered between 48 hours prior to and 48 hours after administration of the therapeutic agent.

Embodiment 27. The method of embodiment 26, wherein the methotrexate is administered concurrently with administration of the therapeutic agent and about 24 and about 48 hours after administration of the therapeutic agent.

Embodiment 28. The method of any one of claims 1-27, wherein the methotrexate is administered at about 0.1 mg/kg to about 5 mg/kg.

Embodiment 29. The method of any one of embodiments 1-28, wherein the sample is obtained from the subject at least about one day to about 30 days following the last administration of the methotrexate.

Embodiment 30. The method of any one of embodiments 1-29, wherein the sample is obtained from the subject at about 7 days to about 14 days following the last administration of the methotrexate.

Embodiment 31. The method of any one of embodiments 1-30, wherein samples are obtained on a plurality of days following the last administration of the methotrexate.

Embodiment 32. The method of embodiment 30, wherein a sample is obtained on one or more of day 1, day 2, day 3, day 4, day 5, day 6, day 7, day 14, day 21, or day 28 following the last administration of the methotrexate.

Embodiment 33. The method of any one of embodiments 1-32, wherein step (4) comprises administering an agent that depletes T-cells, B-cells, or plasma cells.

Embodiment 34. The method of any one of embodiments 1-33, wherein step (4) comprises one or more of: (a) administering an effective amount of one or more of rituximab, intravenous immunoglobulin (IVIG), cyclophosphamide, bortezomib, azathioprine, cyclosporine, mycophenolate, and a corticosteroid; and (b) administering, an antigen-specific tolerance strategy.

Embodiment 35. The method of embodiment 34, wherein the antigenspecific tolerance strategy comprises administering more frequent doses of the therapeutic agent or a higher dose of the therapeutic agent or both.

Embodiment 36. The method of embodiment 35, wherein a higher dose of the therapeutic agent is administered concomitantly with IVIG.

Embodiment 37. The method of any one of embodiments 1-36, wherein the therapeutic agent is a polypeptide, a nucleic acid, a virus, a gene therapy, a lipid, a liposome, or a carbohydrate.

Embodiment 38. The method of any one of embodiments 1-37, wherein the therapeutic agent is a therapeutic polypeptide.

Embodiment 39. The method of embodiment 38, wherein the therapeutic polypeptide is an antibody or antigen-binding fragment thereof.

Embodiment 40. The method of embodiment 39, wherein the antibody is a monoclonal antibody.

Embodiment 41. The method of embodiment 39 or embodiment 40, wherein the antibody is a lymphocyte-depleting agent.

Embodiment 42. The method of embodiment 40 or embodiment 41, wherein the antibody is alemtuzutnab.

Embodiment 43 The method of embodiment 38, wherein the therapeutic polypeptide is an enzyme.

Embodiment 44. The method of embodiment 42, wherein the enzyme is human alpha nalactosidase Embodiment 45. The method of embodiment 42, wherein the enzyme is human acid α-glucosidase.

Embodiment 46. The method of any one of embodiments 1-38 and 43-45, wherein the subject has a lysosomal storage disease.

Embodiment 47. The method of embodiment 46, wherein the subject has Pompe disease.

Embodiment 48. The method of embodiment 47, wherein the Pompe disease is infantile-onset Pompe disease.

Embodiment 49. The method of embodiment 46, wherein the Pompe disease is classic infantile-onset Pompe disease.

Embodiment 50. The method of any one of embodiments 46-49, wherein the subject is cross reactive immunological material (CRIM)-negative.

Embodiment 51. The method of embodiment 50, wherein the method further comprises administering an initial immune tolerance induction therapy concurrently with administration of the therapeutic agent, wherein the therapeutic agent is human acid α-glucosidase.

Embodiment 52. The method of embodiment 51, wherein the initial immune tolerance induction therapy comprises administering one or more of rituximab and IVIG.

Embodiment 53. A method of treating Pompe disease in a subject in need thereof, comprising: (a) administering to the subject an effective amount of methotrexate; (b) administering to the subject an effective amount of human acid α-glucosidase; (c) detecting an erythropoiesis biomarker in a sample obtained from the subject at least one day to about 30 days after administration of methotrexate; and (d) continuing further treatment with the human acid α-glucosidase with or without administering additional immune tolerance induction therapy or immunosuppression therapy based on a level of the erythropoiesis biomarker compared to that of a control.

Embodiment 54. The method of embodiment 53, wherein a change in the level of the erythropoiesis biomarker is associated with induction of erythropoiesis.

Embodiment 55. The method of embodiment 54, wherein if the level of the erythropoiesis biomarker is approximately equal to or less than that of a control, step (d) comprises administering the additional immune tolerance induction therapy or the immunosuppression therapy concurrently with further treatment with the human acid α-glucosidase; or if the level of the erythropoiesis biomarker is elevated with respect to that of a control, step (d) comprises continuing further treatment with the human acid α-glucosidase without administering the additional immune tolerance induction therapy or the immunosuppression therapy.

Embodiment 56. The method of embodiment 54, wherein if the level of the erythropoiesis biomarker is approximately elevated with respect to that of a control, step (d) comprises administering the additional immune tolerance induction therapy or the immunosuppression therapy concurrently with further treatment with the human acid α-glucosidase; or if the level of the erythropoiesis biomarker is equal to or less than that of a control, step (d) comprises continuing further treatment with the human acid α-glucosidase without administering the additional immune tolerance induction therapy or the immunosuppression therapy.

Embodiment 57. The method of embodiment 55, wherein the erythropoiesis biomarker is the level of immature nucleated red blood cells, immature reticulocyte fraction, or cellular nucleic acid contents.

Embodiment 58. The method of embodiment 56, wherein the erythropoiesis biomarker is hematocrit.

Embodiment 59. The method of embodiment 57, wherein if the level of immature nucleated red blood cells initially decreases before the level of immature nucleated red blood cells is elevated, further treatment with the therapeutic agent is continued without administering additional immune tolerance induction therapy or immunosuppression therapy.

Embodiment 60. The method of embodiment 59, wherein the methotrexate is administered in a single cycle, wherein the level of immature nucleated red blood cells decreases by about one, about two, about three, about four, about five, about six, or about seven days before the level of immature nucleated red blood cells becomes elevated.

Embodiment 61. The method of embodiment 59, wherein the methotrexate is administered in two or more cycles, wherein the level of immature nucleated red blood cells decreases by about one to about 14 days before the level of immature nucleated red blood cells becomes elevated.

Embodiment 62. The method of embodiment 55 or 56, wherein detecting the erythropoiesis biomarker is detecting the expression of a gene associated with erythropoiesis, wherein the gene associated with erythropoiesis is a gene associated with one or more of hemopoiesis, iron ion homeostasis, regulation of erythrocyte differentiation, and heme metabolism.

Embodiment 63. The method of embodiment 62, wherein the gene associated with erythropoiesis is a gene encoding transferrin receptor, transferrin Ly76 (antigen for Ter-119), CD44, CD235a, ALAS2, or GATA-1.

Embodiment 64. The method for embodiment 63, wherein the transferrin receptor is transferrin receptor 1 (CD71).

Embodiment 65. The method of any one of embodiments 62-64, wherein detecting the gene associated with erythropoiesis comprises detecting an RNA transcript of the gene associated with erythropoiesis or detecting a protein product of the gene associated with erythropoiesis.

Embodiment 66. The method of embodiment 65, wherein the protein product is hemoglobin.

Embodiment 67. The method of embodiment 55, wherein the erythropoiesis biomarker is a co-factor associated with erythropoiesis.

Embodiment 68. The method of embodiment 67, wherein the co-factor associated with erythropoiesis is porphyrin, a porphyrin-containing compound, or a tetrapyrrole.

Embodiment 69. The method of any one of embodiments 53-68, wherein the sample is a blood sample.

Embodiment 70. The method of embodiment 69, wherein the blood sample is a blood fraction comprising peripheral blood mononuclear cells (PBMC).

Embodiment 71. The method of any one of embodiments 53-70, wherein the subject is human.

Embodiment 72. The method of any one of embodiments 53-71, wherein the Pompe disease is infantile-onset Pompe disease.

Embodiment 73. The method of embodiment 72, wherein the Pompe disease is classic infantile-onset Pompe disease.

Embodiment 74. The method of embodiment 72 or 73, wherein the subject is CRIM-negative.

Embodiment 75. The method of any one of embodiments 53-74, wherein the control is a historical control or a placebo control.

Embodiment 76. The method of any one of embodiments 53-75, wherein the effective amount of methotrexate is administered in a single cycle or in three cycles.

Embodiment 77. The method of embodiment 76, wherein an effective amount of methotrexate is administered in a single cycle.

Embodiment 78. The method of embodiment 76 or embodiment 77, wherein a cycle of methotrexate consists of 1 day of methotrexate administration or 2, 3, 4, 5, 6, 7, 8, 9, 10, or 11 consecutive days of methotrexate administration.

Embodiment 79. The method of any one of embodiments 53-78, wherein the effective amount of methotrexate is administered to the subject at a time selected from one or more of before, during, and after administration of the therapeutic agent.

Embodiment 80. The method of embodiment 79, wherein an effective amount of methotrexate is administered between 48 hours prior to and 48 hours after the administration of the therapeutic agent treatment.

Embodiment 81. The method of embodiment 80, wherein the methotrexate is administered concurrently with administration of the therapeutic agent and about 24 and about 48 hours after administration of the therapeutic agent.

Embodiment 82. The method of any one of clams 53-81, wherein the effective amount of methotrexate is about 0.1 mg/kg to about 5 mg/kg.

Embodiment 83. The method of any one of embodiments 53-82, wherein detecting the erythropoiesis biomarker in the sample is at least about one day to about 30 days following the last administration of the methotrexate.

Embodiment 84. The method of any one of embodiments 53-83, wherein detecting the erythropoiesis biomarker in the sample is at about 7 days to about 14 days following the last administration of the methotrexate.

Embodiment 85. The method of any one of embodiments 53-84, wherein samples are obtained on a plurality of days following the last administration of the methotrexate.

Embodiment 86. The method of embodiment 85, wherein a sample is obtained on one or more of day 1, day 2, day 3, day 4, day 5, day 6, day 7, day 14, day 21, or day 28 following the last administration of the methotrexate.

Embodiment 87. The method of any one of embodiments 53-86, wherein step (d) further comprises administering an agent that depletes T-cells, B-cells, or plasma cells.

Embodiment 88. The method of embodiment 87, wherein the agent that depletes plasma cells is bortezomib.

Embodiment 89. The method of any one of embodiments 53-88, wherein step (d) comprises one or more of: (a) administering an effective amount of one or more of rituximab, intravenous immunoglobulin (IVIG), cyclophosphamide, bortezomib, azathioprine, cyclosporine, mycophenolate, and a corticosteroid, and (h) administering an antigen-specific tolerance strategy.

Embodiment 90. The method of embodiment 89, wherein the antigenspecific tolerance strategy comprises administering more frequent doses of the therapeutic agent or a higher dose of the therapeutic agent or both.

Embodiment 91. The method of embodiment 90, wherein a higher dose of the therapeutic agent is administered concomitantly with IVIG.

Embodiment 92. The method of any one of embodiments 53-91, further comprising monitoring one or more of anti-human acid α-glucosidase antibody, CD19 levels. or disease progression.

Embodiment 93. A method of assessing the level of immune tolerance in a subject with Pompe disease. comprising: (a) obtaining a sample from the subject, wherein the subject has previously been administered at least one cycle of methotrexate treatment and at least one dose of a therapeutic agent and (b) detecting an erythropoiesis biomarker in the sample, wherein the level of the erythropoiesis biomarker in the sample with respect to the level of a control indicates an induction of immune tolerance.

Embodiment 94. The method of embodiment 93, wherein step (b) comprises contacting the sample with an agent that binds to an erythropoiesis biomarker.

Embodiment 95. A method of assessing the level of immune tolerance to a therapeutic agent in a subject in need of the therapeutic agent, comprising: (a) administering to the subject an effective amount of methotrexate; (b) administering to the subject an effective amount of the therapeutic agent; and (c) detecting an erythropoiesis biomarker in a sample obtained from the subject, wherein a level of the erythropoiesis biomarker in the sample with respect to the level of a control indicates induction of immune tolerance in the subject to the therapeutic agent.

Embodiment 96. A method of assessing the level of immune tolerance to a therapeutic agent in a subject in need of the therapeutic agent, comprising: (a) administering to the subject an effective amount of methotrexate; (b) administering to the subject an effective amount of the therapeutic agent; (c) detecting erythropoiesis biomarker in a sample obtained from the subject at least one day to about 30 days after administration of methotrexate; and (d) identifying the level of immune tolerance to the therapeutic agent in the subject based on the level of the biomarker detected in step (c).

Embodiment 97. The method of any one of embodiments 93-96, wherein the change in the level of the erythropoiesis biomarker is associated with induction of erythropoiesis Embodiment 98. The method of embodiment 97, wherein if the level of the erythropoiesis biomarker is approximately equal to or less than that of a control, the subject is in need of additional immune tolerance induction therapy or immunosuppression therapy concurrently with further treatment with the therapeutic agent; or if the level of the erythropoiesis biomarker is elevated with respect to that of a control, the subject is not in need of additional immune tolerance induction therapy or immunosuppression therapy.

Embodiment 99. The method of embodiment 97, wherein if the level of the erythropoiesis biomarker is approximately elevated with respect to that of a control, the subject is in need of additional immune tolerance induction therapy or immunosuppression therapy concurrently with further treatment with the therapeutic agent; or wherein if the level of the erythropoiesis biomarker is equal to or less than that of a control, the subject is not in need of additional immune tolerance induction therapy or immunosuppression therapy.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Example 1

Figure 1B:
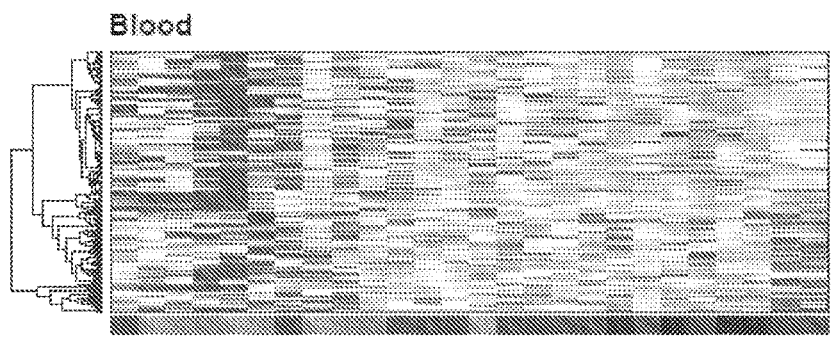
FIG. 1B shows a heat map of a subset of gene expression levels associated with erythropoiesis in blood samples of mice in various experimental groups. Four to nine C57BL/6 mice/group were treated with rhGAA with and without low-dose methotrexate as described in Example 1. Experimental control groups of mice treated with FB (formulation buffer) with and without methotrexate were included. On day 7 after rhGAA initiation, spleen (A) and blood (B) samples were examined by RNA-sequencing on an Illumina HISEQ2000® after RNA amplification. The genes shown are a subset of the total genes which are associated with erythropoiesis. RNA-sequencing data sets were screened for differential expression with a fold change (FC) $\geq 2$ and p value $\leq 0.05$. Red signifies highly upregulated genes, whereas blue indicates downregulated genes. The results demonstrate that the exemplary transient low-dose methotrexate regimen upregulates transcriptional signatures in erythropoiesis in spleen and blood.
Figure 1C:
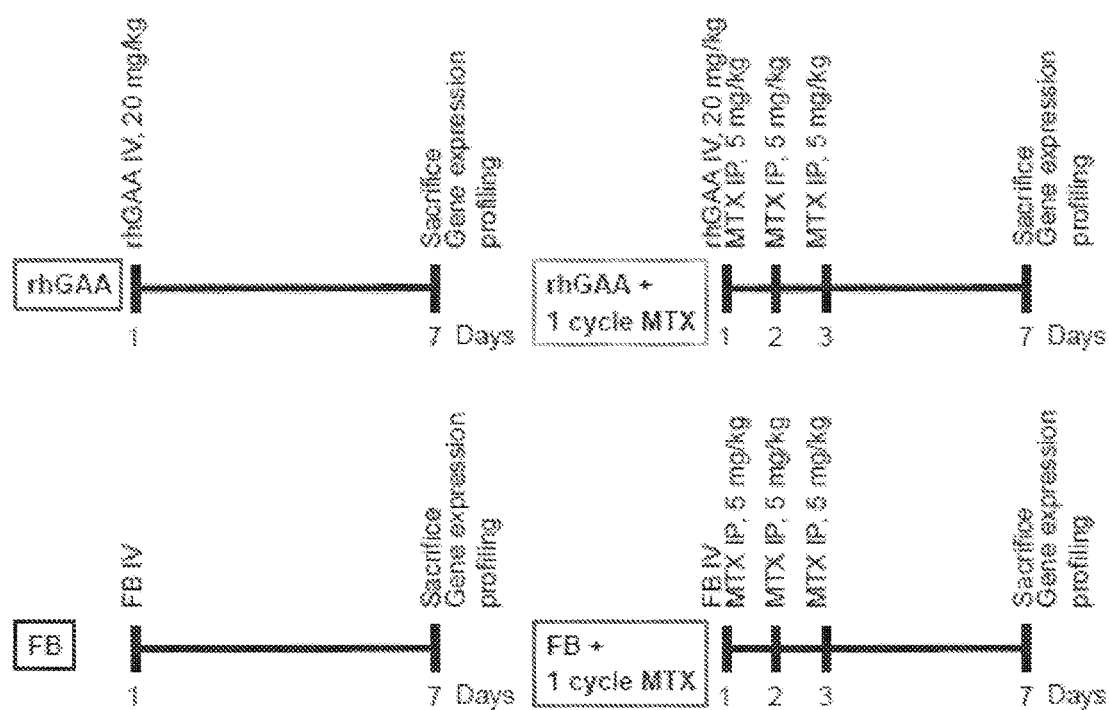
FIG. 1C shows a schematic of the study design described in Examples 1-4.

Transcriptional and Protein-Level Response in the Spleen and Blood of Mice Treated with a Transient Low-Dose Methotrexate Immune Tolerance Induction Regimen Introduction To understand the mechanism of action of immune tolerance induction by a transient low-dose methotrexate ITI regimen, next-generation sequencing and protein mass spectrometry studies were performed to examine spleen and peripheral blood mononuclear cells (PBMC's) of mice treated with rhGAA with or without low-dose methotrexate and mice in control groups. A schematic of the study design is shown in FIG. 1C.

Materials and Methods

Mice, rhGAA, and Low-Dose Induction Regimen of Methotrexate

C57BL/6 (Jackson Laboratory) or C57BL/6NTac (Taconic Biosciences, Inc.) female mice between S and 12 weeks of age were housed and maintained in accordance with the *Guide for the Care and Use of Laboratory Animals*, under the American Association for Accreditation of Laboratory Animal Care. The Institutional Animal Care and Use Committee approved all animal procedures. Mice were treated with a single cycle of low-dose induction. regimen of methotrexate concurrent with rhGAA (Genzyme, a Sanofi company) injection a.s previously described (Joly et. al., 2014). Briefly, age-matched, gender-matched mice were given a single cycle (3 consecutive daily doses at 0, 24 and 48 hours) of low-dose induction regimen of methotrexate, 5 mg/kg, by intraperitoneal injection within 15 minutes of tail vein intravenous injection of rhGAA, 20 mg/kg. Subsequent weekly doses of rhGAA (up to 16 weeks) were given 15 minutes after prophylactic intraperitoneal administration of 30 mg/kg diphenhydramine (West-ward Pharmaceutical). The vehicle control or formulation buffer (FB) for rhGAA. was administered similarly to reconstituted rhGAA. Blood was collected by retro-orbital Heeds from anesthetized mice or by terminal bleeds into EDTA anticoagulant Capiject micro collection tubes (Terumo) on wet ice. Spleens were prepared into single-cell suspension between glass slides with or without RBC lysis. Bone marrow was collected from a single femur on wet ice.

Transcriptional Analysis

Age-matched, gender matched mice were treated with rhGAA or formulation buffer (FB) 15 minutes prior to injection with or without a single cycle of low-dose induction regimen of methotrexate as described above. Animals were sacrificed on day 7 after rhGAA initiation. Blood was collected by terminal retro-orbital bleeds as described above. Whole blood diluted 1 part in 2 with PBS was layered over Ficoll for the separation of peripheral blood mononuclear cells (PBMC's). Spleens were prepared into single-cell suspension between glass slides. Samples were treated for RBC lysis (BD Pharm Lyse). Samples were flash frozen in TRIZOL™ (phenol, guanidine isothiocyanate solution, Thermofisher Scientific) and stored at −80° C. prior to submission to BG1 (worldwide web.bgi.com/us/) for next-generation sequencing, analysis. The RNA integrity number (RIN) was evaluated. on an Agilent 2100 bioanalyzer with the RNA 6000 nano kit (Agilent) or RNA 6000 pica kit (Agilent). RNA amplification was performed with the SMARTER™ PCR cDNA Synthesis Kit (Clonetech). Detection of sequencing fragments was performed on the Illumina HiSeq2000 with Illumina sequencing kits. RNA-seq data sets were filtered to remove adaptors and low-quality, reads and assessed for differential expression with a fold change of 2 and p value≤0.05. Differentially expressed genes were annotated and examined through NextBio biological data mining software (Illumina).

Protein Mass Spectrometry

Age-matched, gender matched mice were treated with or without a single cycle of low-dose induction regimen of methotrexate concurrently with rhGAA or FB injection and animals were sacrificed 7 days after rhGAA initiation as described above. Blood was collected by terminal retro-orbital bleeds as described above followed by separation of plasma and PBC by centrifugation. Spleens were prepared into single-cell suspension as described above. Spleen and blood samples were flash frozen and submitted to MS Bioworks (worldwide web msbioworks.com) to be processed by LC/MS protein mass spectrometry. At MS Bioworks, plasma was depleted of albumin, and transferrin using multiple affinity removal spin cartridge mouse 3 (MARS3). Cells were lysed in a modified RIPA buffer containing protease and phosphatase inhibitors. A single LC/MS/MS analysis was performed on an Orbitrap (Velos Pro) tandem mass spectrometer (ThermoFisher) interfaced to a NanoAcquity HPLC (Waters) per sample peptide digest. Data was analyzed by Progenesis QI for Proteomics (Nonlinear Dynamics) for peak detection. Protein identification and characterization was performed through the Mascot database (Matrix Science version 2.4) with cutoff at 10 ppm precursor and 0.05 Da products (Q-Exactive). False negative and positives were filtered through Scaffold (Proteome Software version 4.0). Protein quantitation was performed through Progenesis QI for Proteomics. Fold change and p-values were calculated from the average normalized protein abundance data for each experimental group. Differentially expressed proteins were defined by a fold change of 2 and p value ≤0.05. Data were analyzed for enrichment scores in GO processes and other biological categories in MetaCore (Thomson Reuters).

Results

Low-Dose Methotrexate Induction Regimen Upregulates Transcriptional Signatures in Erythropoiesis Mice were treated with rhGAA with or without low-dose methotrexate as described above. Experimental control groups where mice were dosed with the vehicle control (formulation buffer, FB) in the presence or absence of methotrexate were included. Seven days after rhGAA initiation spleen and blood were collected and processed into splenocytes and PBMC's, respectively. Differences between the treatment groups were examined in these tissue preparations by next generation sequencing (NGS). The RNA-sequencing data showed upregulation of transcriptional signatures of erythropoiesis in spleen (FIG. 1A) and PBMC's (FIG. 1B) of mice treated with rhGAA in conjunction with low-dose methotrexate. FIGS. 1A and 1B show a representative subset of differentially expressed genes that are associated with erythropoiesis out of the total dataset. Upregulation of erythropoiesis-related gene expression signatures in the spleen and PBMC's of mice treated with rhGAA and low-dose methotrexate is remarkably distinct from the other groups, even from mice that were treated with methotrexate alone.

Transcriptional module analysis showed cell cycle pathways impacted in the spleen of mice treated with rhGAA and low-dose methotrexate when compared to mice treated with rhGAA alone. Beyond changes in cell cycle, the transcriptional module analysis indicated an enrichment in erythrocyte proliferation related pathways, including hemopoiesis, iron ion homeostasis, regulation of erythrocyte differentiation and heme metabolism (Table 1, below). In contrast, the blood samples showed signs of a cellular stress response (data not shown), but also showed enrichment in heme metabolism (Table 1). Overall, transcriptional analysis of spleen and blood showed upregulation in erythropoiesis related pathways in the group treated with rhGAA and methotrexate seven days after rhGAA.

Figure 2:
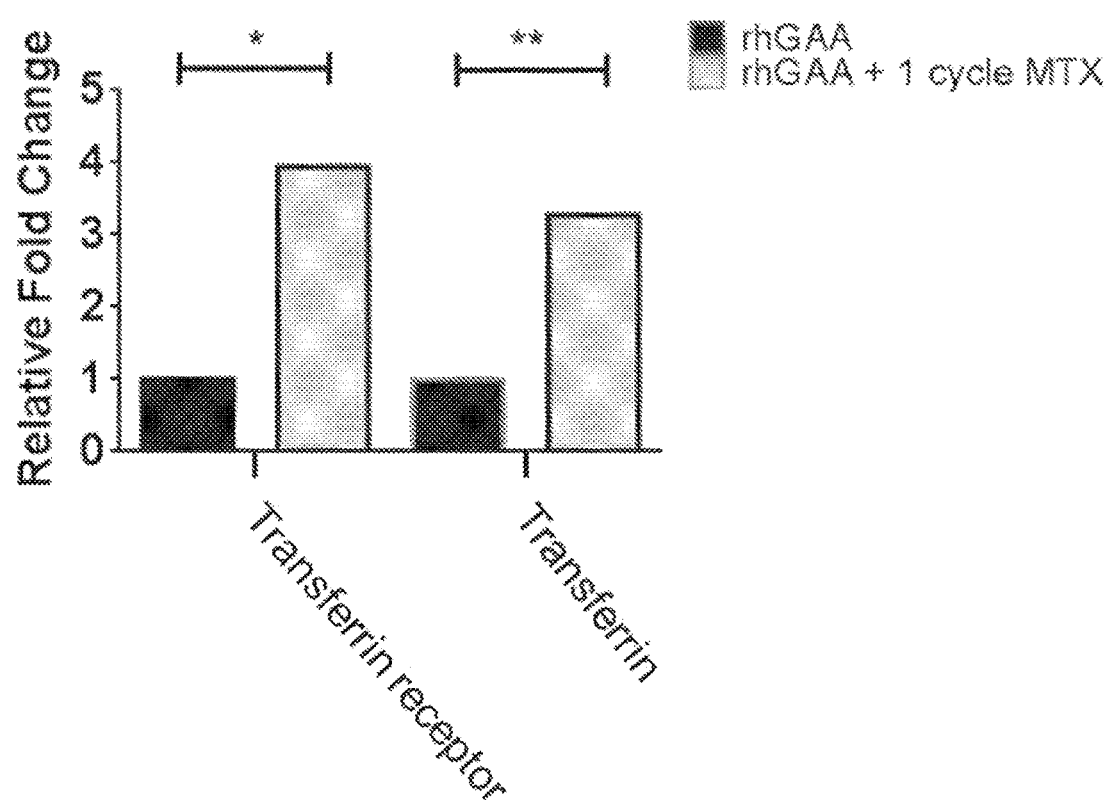
FIG. 2 shows upregulation of transferrin and transferrin receptor I in spleen in response to the exemplary transient low-dose methotrexate regimen. Eight C57BL/6 mice/group were treated with rhGAA in the absence or presence of the exemplary transient low-dose methotrexate regimen as described in Example 1. On day 7 after rhGAA initiation, spleen and blood samples were examined by LC/MS protein mass spectrometry. Differentially expressed genes were screened with FC$\geq$2 and p value 0.05.
Figure 3A:
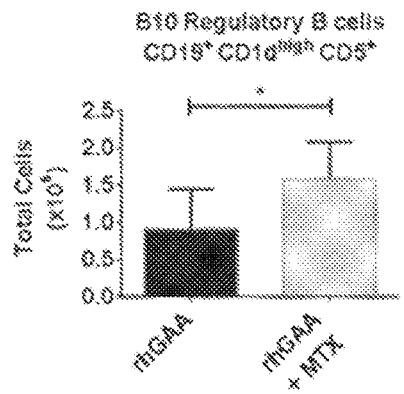
FIG. 3A shows significantly enriched B10 regulatory B cells in the rhGAA+MIX group.
Figure 3B:
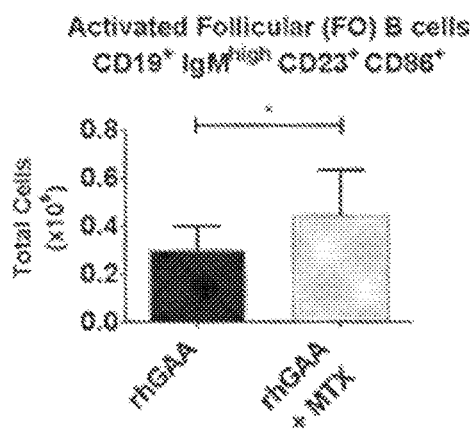
FIG. 3B shows significantly enriched activated follicular (FO) B cells in the rhGAA+L group.
Figure 3C:
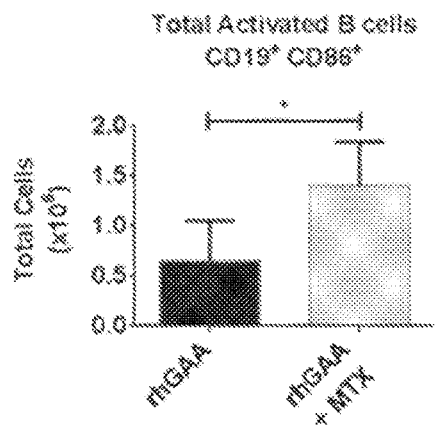
FIG. 3C shows significantly enriched total activated B cells in the rhGAA+MIX group.
Figure 3D:
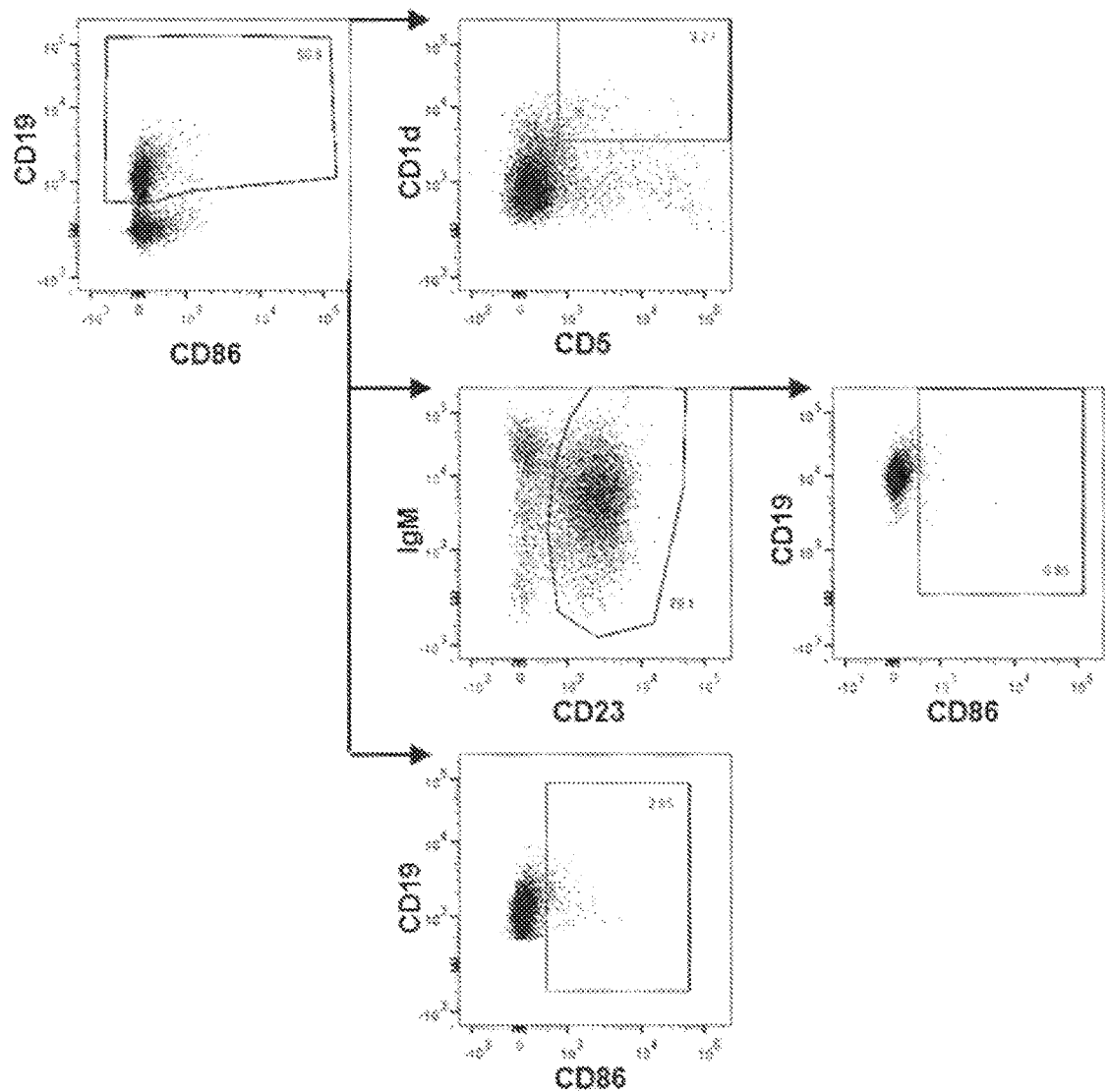
FIG. 3D shows gating strategy in flow cytometry to select for live CD19$^+$ events. Subsequent gating selected for B10 regulatory B cells (top: CD19$^+$, CD1d$^{high}$CD5$^+$), activated follicular B cells (second row: CD19$^+$, IgM$^{low/high}$CD23$^+$, CD86$^+$), and total activated B cells (bottom: CD19$^+$CD86$^+$). Four to ten C57BL/6 or C57BL/6NTac mice/group were treated with rhGAA alone or together with a single cycle of low-dose methotrexate as described in .Example 1. Seven days after rhGAA initiation, spleens were extracted post-mortem, homogenized into single cell suspensions, subjected to RBC lysis and examined by flow cytometry as described in Example 2. These data are from three or more separate experiments. Student t tests were performed and significance is noted as *f≤0.05. The enriched B cell subsets demonstrated patterns of immune tolerance following transient low-dose methotrexate treatment.

Low-Dose Methotrexate Induction Regimen Upregulates Protein Signatures in Erythropoiesis Proteomic analysis was also carried out to identify pathways at the protein level that may be modulated by low dose methotrexate treatment. The study design was similar to the transcriptional study as described above, but examined by protein mass spectrometry. The proteomic dataset showed enrichment in hemopoiesis and iron ion homeostasis-related pathways (Table 1). The associated proteins include transferrin receptor 1 (TfR1, also called CD71, highly expressed in) a marker of immature, nucleated RBCs [Dong et. al., 2011]) and its ligand transferrin (FIG. 2) (TfR1 also showed upregulation in the transcriptional data set). Transferrin receptor 1 is required for iron import from transferrin into cells. These proteins mediate iron uptake, an essential role in heme biosynthesis in developing erythroid cells. Upregulation of these proteins suggest active hemoglobin biosynthesis could be taking place in developing RBCS. Enrichment in genes and proteins involved in erythrocyte production and function was commonly observed across each of the experimental datasets measuring differential expression in the spleen between the groups treated with rhGAA and low-dose methotrexate compared to the groups given rhGAA alone. Therefore, proteomic analysis of the spleen indicated upregulation in erythropoiesis related pathways in groups treated with rhGAA and methotrexate seven days after rhGAA.

TABLE 1

Enrichment of differentially-regulated objects across functional categories relating to hematological effects.

| Functional Category | mRNA | | Protein | |
|---|---|---|---|---|
| | p | ratio | p | ratio |
| GO Biological Processes | | | | |
| Hemopoeisis | 2.02E−11 | 52/889 | 0.060 | 7/153 |
| Iron ion homeostasis | 3.35E−16 | 13/130 | 0.001 | 5/36 |
| Regulation of Erythrocyte differentiation | 7.74E−6 | 9/65 | NS | 1/9 |
| MetaCore Pathway Maps | | | | |
| Heme metabolism | 4.25E−5 | 10/103 | NS | 1/16 | mRNA: Differentially-expressed mRNA species from the RNA-Seq dataset (FC ≥ 2, p ≤ 0.01). Protein: Differentially-expressed proteins from the MS Bioworks dataset (FC ≥ 2, p ≤ 0.05). p: hypergeometric distribution p-value for the differentially-expressed objects from each experiment Ratio: number of differentially-expressed objects within the functional category over the number of category objects assayable in the experiment. NS: not significant.

Example 2

Effects on Erythroid Cells in the Spleen, Blood, and Bone Marrow of Mice Treated with a Transient Low-Dose Methotrexate Immune Tolerance Induction Regimen Introduction To evaluate and understand the effect of immune tolerance induction by transient low-dose methotrexate ITI regimen in the spleen, blood and bone marrow, flow cytometry studies were performed to examine spleen, blood, and bone marrow samples of mice treated with rhGAA with or without transient low-dose methotrexate ITI regimen and mice in control groups. Additionally, immunohistochemistry and tissue mass spectrometry imaging studies were performed to further assess erythropoiesis in the spleen samples of mice treated with rhGAA with or without transient low-dose methotrexate ITI regimen and mice in control groups.
Materials and Methods
Flow Cytometry Anti-mouse antibodies used for flow cytometry include BioLegend antibodies PE-Ter-119 (catalog 116208), PerCP-Cy5.5-CD71 (catalog 113816), PE-Cy7-IgM (catalog 406516), Pacific Blue (PB)-CD86 (catalog 105022) and allophycocyanin-CD45 (catalog 103116). Antibodies from BD Biosciences include FITC-CD44 (catalog 553133), allophycocyanin-CD3 (catalog 550035), allophycocyanin-CD19 or allophycocyanin-Cy7-CD19 (catalog 557655 and 550992), FITC-CD1d (catalog 553843), FITC-CD23 (catalog 553138) and allophycocyanin-Cy7-CD3, (catalog 557596). Live/dead discrimination was determined by staining with BioLegend Zombie Aqua Fixable Visability Kit. Samples were run on a BD FACS Canto II (BD Biosciences) and acquired with BD FACSDiva software. Cytometry data was analyzed on Floyd( )software version 10 (FlowJo, LLC). Absolute numbers of cell population were calculated from CountBright Absolute Counting Beads (ThermoFisher Scientific). Cell types assessed include total RBCs (Ter-119$^+$), immature, nucleated RBCs (Ter-119$^+$, CD71$^+$), mature RBCs (Ter-119$^+$, CD71$^+$), proerythrohlasts (Ter-119$^{intermediate}$, CD44$^{high}$), basophilic erythroblasts (Ter-119$^+$, CD44$^{high}$FSC$^{high}$), polychromatic erythroblasts (Ter-119$^+$, CD44$^{intermediate}$FSC$^{intermediate}$), orthochromatic erythroblasts and reticulocytes (Ter-119$^+$, CD44$^{intermediate}$FSC$^{low}$), mature red blood cells (Ter-119$^+$, CD44$^{low}$FSC$^{low}$), total activated B cells (CD19$^+$CD86$^+$), activated follicular B cells (CD19$^+$, IgM$^{low/high}$ CD23$^+$, CD86$^+$), activated marginal zone B cells (CD19$^+$, IgM$^{high}$ CD23$^-$, CD86$^+$), and B10 regulatory B cells (CD19$^+$, CD1d$^{high}$CD5$^+$) (Allman et. al., 2004: Chen et. al., 2009; Koulnis et. al., 2011; Joly et. al., 2014).
Hematology Samples were collected by retro-orbital bleed into EDTA anticoagulant Capiject micro collection tubes as described above and stored at 2-8° C. for no longer than 72 hours. CBC, WBC differential analysis and reticulocyte count were performed on Sysmex XT2000iV (Sysmex). Histology, immunohistochemistry (IHC)

Spleen samples were fixed in 4% paraformaldehyde in PBS, infiltrated with 30% sucrose, embedded in optimal cutting temperature (OCT) medium and snap frozen for immunofluorescence or histology. Alternatively samples were processed in paraffin for histology. Hematoxylin and eosin staining were carried out as described previously and examined by light microscopy (Burrow. Sun et al. 2015). For immunofluorescence, samples were incubated with a rat anti-mouse Ter-119 (catalog 116202) or CD71 (catalog 113802) monoclonal antibody from BioLegend and detected with biotinylated rabbit anti-rat IgG antibody. Immunofluorescence analysis of sections stained with the Ter-119 or CD71 antibody was performed on the Discovery XT Staining Module on BenchMark. XT Automated IHC/ISH slide staining system (Ventana Medical System). Ventana IHC DAB Map Kit was used for detection. Immunofluorescence slides were scanned using a 20×objective lens in a Mirax scanner (Carl Zeiss). Tissue sections were counterstained with hematoxylin and analyzed by light microscopy. Representative 100× digital images were subjected to Ter-119 or CD71-positive area quantification or quantitative histomorphometry using HALO image analysis software (Indica Labs).
Tissue Mass Spectrometry Imaging (tMSI)

Fresh spleen samples for tMSI were collected in 10% gelatin (Alfa Aesar catalog J62699), frozen en bloc, cut into 10 μM sections, and deposited on indium tin oxide (1170) glass slides. ITO glass slides were coated with matrix-assisted laser desorption/ionization (MALDI) matrix (α-cyano-4-hydroxycinnamic acid) for tMSI. Mass spectrometry imaging was performed with AB Sciex 4800

MALDI-TOF/TOF, Autoflex MALDI-TOF/TOF and 7T SolariX MALDI-FTICR mass spectrometers. The imaging data sets were analyzed with TissueView, flexImaging, or Multimaging 1.1 (ImaBiotech).

Results

Figure 4A:
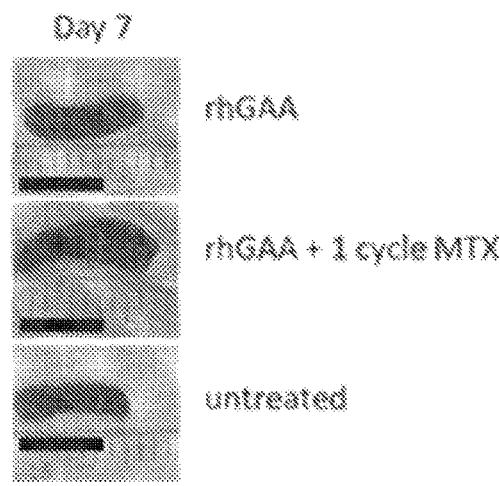
FIG. 4A shows representative images of spleens (black bar=1 cm) from mice in different experimental groups.
Figure 4B:
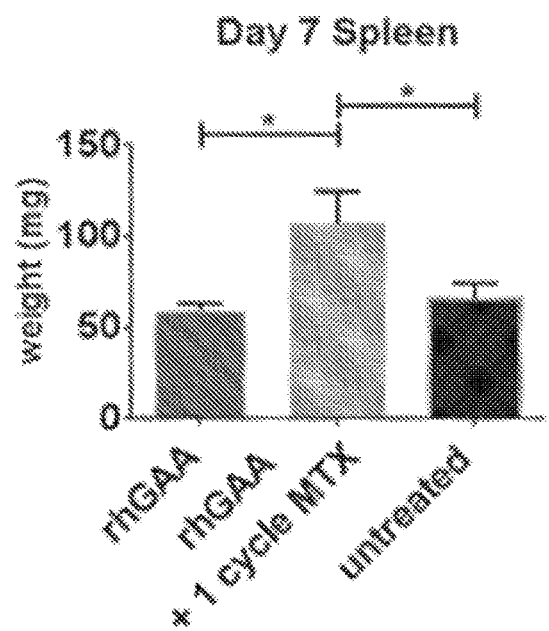
FIG. 4B shows a graphical representation of spleen weight of mice at day 7 after rhGAA initiation.
Figure 4C:
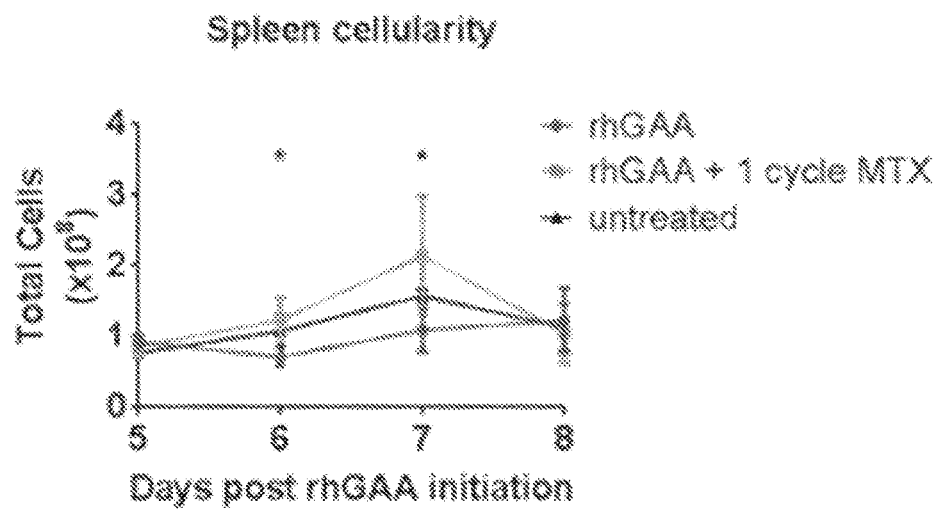
FIG. 4C shows total numbers of cells in spleen samples measured on days 5, 6, 7 and 8 by flow cytometry. Four to six C57BL/6NTac mice/group were treated with 20 mg/kg i.v. rhGAA alone or in combination with a single cycle of low-dose methotrexate (three consecutive, daily i.p. treatments of 5 mg/kg within 15 minutes of rhGAA treatment). Spleens were homogenized into single cell suspensions and examined by flow cytometry as described in Example 2.

Expansion of Activated B Cell Subsets in Response to Transient Low-Dose Methotrexate Treatment Regulatory B cells have previously been demonstrated to be important for the induction of immune tolerance by transient low-dose methotrexate (Joly et. al., 2014). In all experiments described herein, including the transcriptional studies described in Example 1, patterns of immune tolerance induction, specifically the expansion of activated. B cell subsets previously associated with immune tolerance induction, were demonstrated by flow cytometry (FIGS. 3A-3D), Transient Low-Dose Methotrexate Treatment Leads to Short-Term Depletion of Erythroid Cells Followed by Enrichment of Ter-119$^+$ CD71$^+$ Immature, Nucleated RBCs in the Spleen Mice treated with rhGAA concurrent with a single cycle of low-dose methotrexate exhibited significantly enlarged spleens by weight (FIGS. 4A-4B) and had significantly greater spleen cellularity as measured by flow cytometry at day 7 after rhGAA initiation (FIG. 4C). The observed splenomegaly together with the upregulation in signatures of erythropoiesis shown in the omics data prompted the cellular examination of RBCs during transient low-dose methotrexate induction treatment.

Figure 4D:
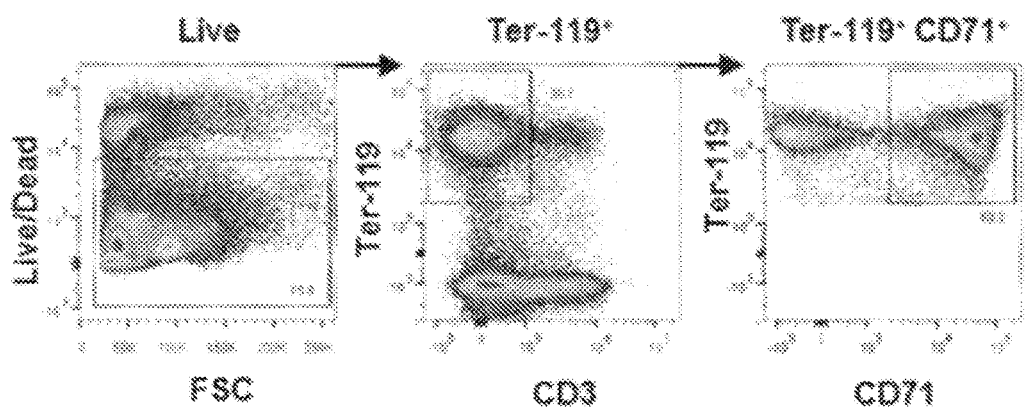
FIG. 4D shows gating, strategy in flow cytometry of the spleen samples of mice. Live total RBCs (Ter-119$^+$) and the immature, nucleated RBC subset (Ter-119$^+$CD71$^+$) were selected.
Figure 4E:
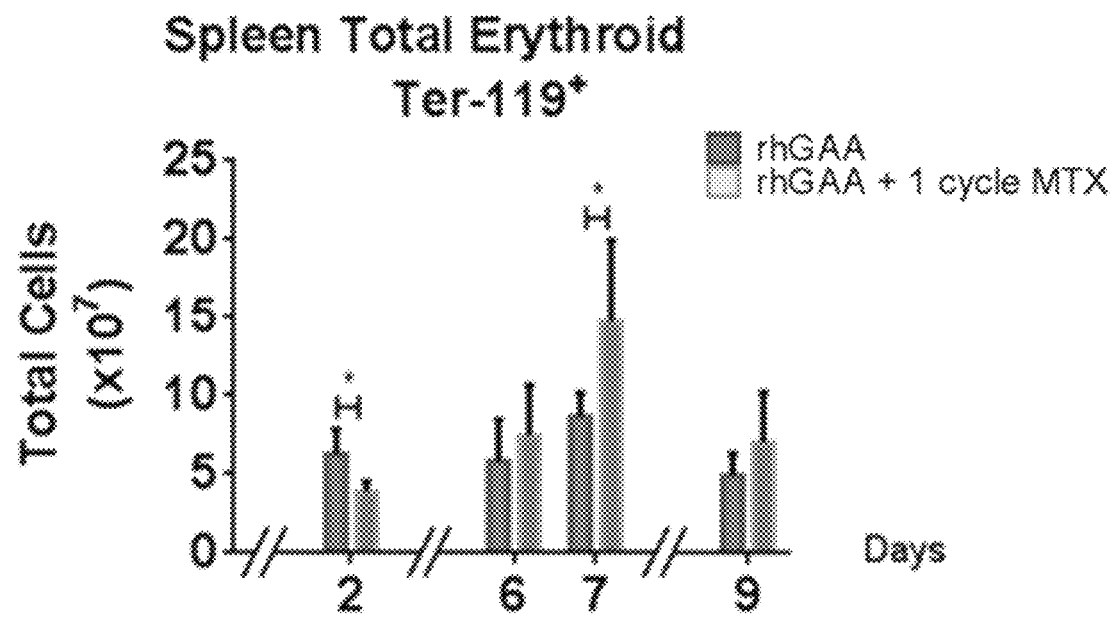
FIG. 4E shows numbers of total RBCs in the spleens of mice on days 2, 6, 7 and 9 after rhGAA initiation.
Figure 4F:
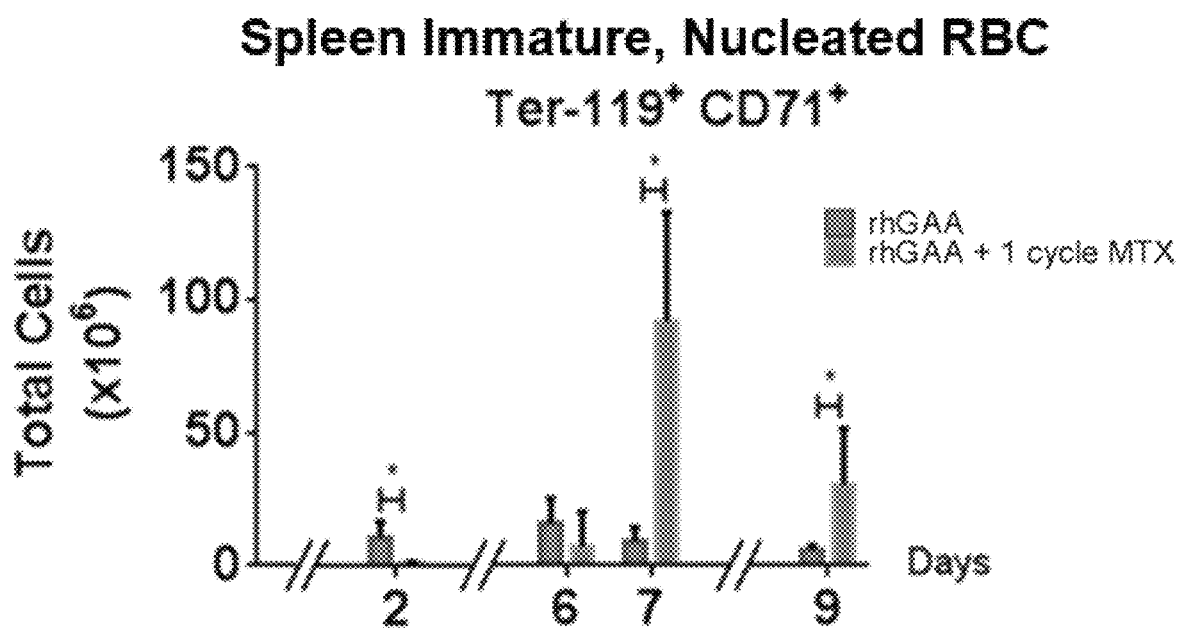
FIG. 4F shows numbers of immature, nucleated RBCs in the spleens of mice on days 2, 6, 7 and 9 after rhGAA initiation. Mice were dosed with either rhGAA alone (rhGAA) or rhGAA in combination with a single cycle of low-dose methotrexate (rhGAA+1 cycle MTX).
Figure 4G:
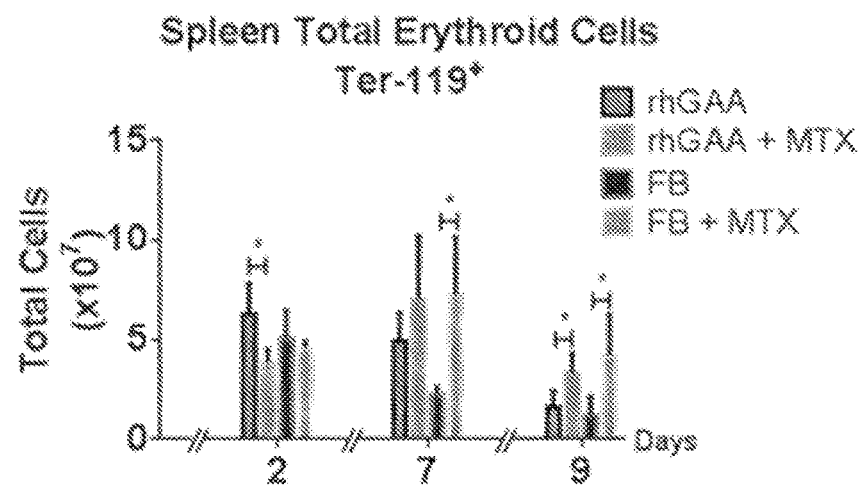
FIG. 4G shows numbers of total RBCs in the spleens of mice on days 2, 7 and 9 after rhGAA initiation.
Figure 4H:
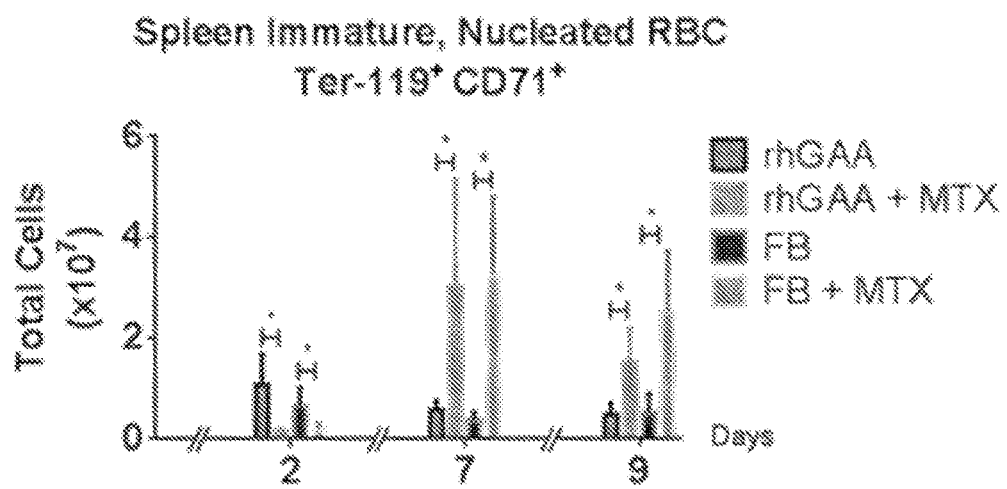
FIG. 4H shows numbers of immature, nucleated RBCs in the spleens of mice on days 2, 7 and 9 after rhGAA initiation. Experimental control groups of mice treated with vehicle control FB (formulation buffer) with and without methotrexate were included. These data are from three or more separate experiments. Student tests were performed and significance is noted as *≤0.05. Vertical bars represent standard deviation. The results demonstrate that the exemplary transient low-dose methotrexate regimen caused an early, short-term reduction followed by an enrichment of total and immature, nucleated RBCs and enlarged spleens.

Age matched, gender-matched mice were treated with rhGAA with and without a single cycle of a low-dose regimen of methotrexate and animals were sacrificed over time for analysis by flow cytometry. The erythroid specific monoclonal antibody Ter-119 was used to examine total live RBCs (FIG. 4D). Immature, nucleated RBCs were distinguished from mature RBCs by the transferrin receptor CD71 (Pan and Johnstone 1983). On day 2 after rhGAA initiation but prior to the second methotrexate administration, a significant reduction of total erythroid cells (Ter-119$^+$) and nearly complete reduction of immature, nucleated RBCs (Ter-119$^+$CD71$^+$) were observed in the low-dose methotrexate treated group in the spleen (FIG. 4E). No differences were observed between groups on day 6. A large and significant enrichment of total erythroid cells was seen on day 7 was also signified by a concurrent and significant expansion of immature, nucleated RBC is (FIG. 4F). A smaller but significant enrichment of total erythroid cells and immature, nucleated RBCs was observed on day 9. In groups treated with transient low-dose methotrexate alone, the erythroid response mimicked that of the group treated with transient low-dose methotrexate together with rhGAA (FIGS. 4G, 4H).

Thus, in the spleen, a temporary but significant reduction in immature, nucleated RBCs and mature RBCs could be observed within 24 hours of the first administration of low-dose methotrexate. This is followed by an overshoot response where immature, nucleated RBCs are significantly enriched in the spleen of tolerized mice. The enrichment of immature, nucleated RBCs peaks at day 7 which may account for the significantly enlarged spleens observed on this day. When comparing, groups given rhGAA together with transient low-dose methotrexate ITI regimen and groups treated with transient low-dose methotrexate ITI regimen alone, the erythroid response were similar. This suggests the transient low-dose methotrexate regimen dominantly contributed to the observed erythroid response.

Figure 5A:
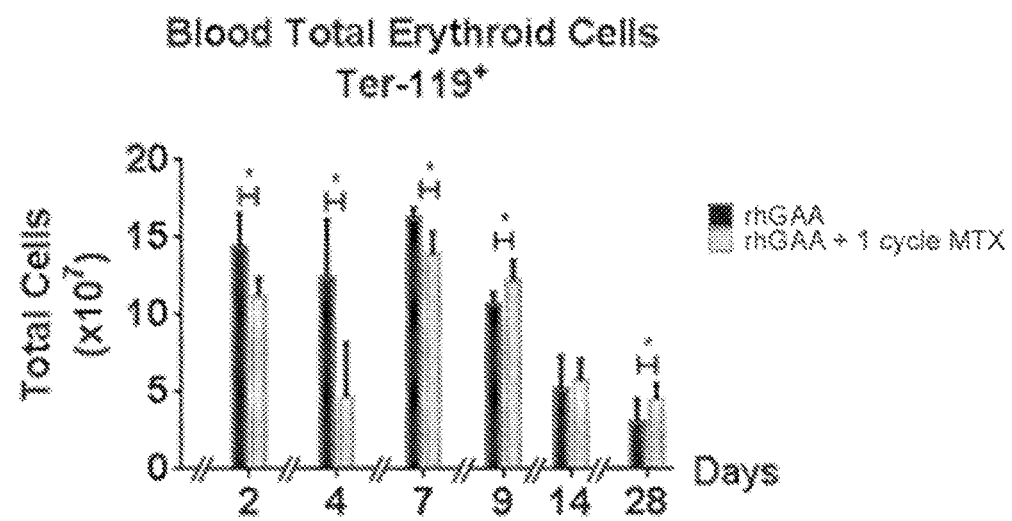
FIG. 5A shows numbers of total RBCs in the blood of mice on days 2, 4, 7, 9, 14 and 28 after rhGAA initiation as determined by flow cytometry.
Figure 5B:
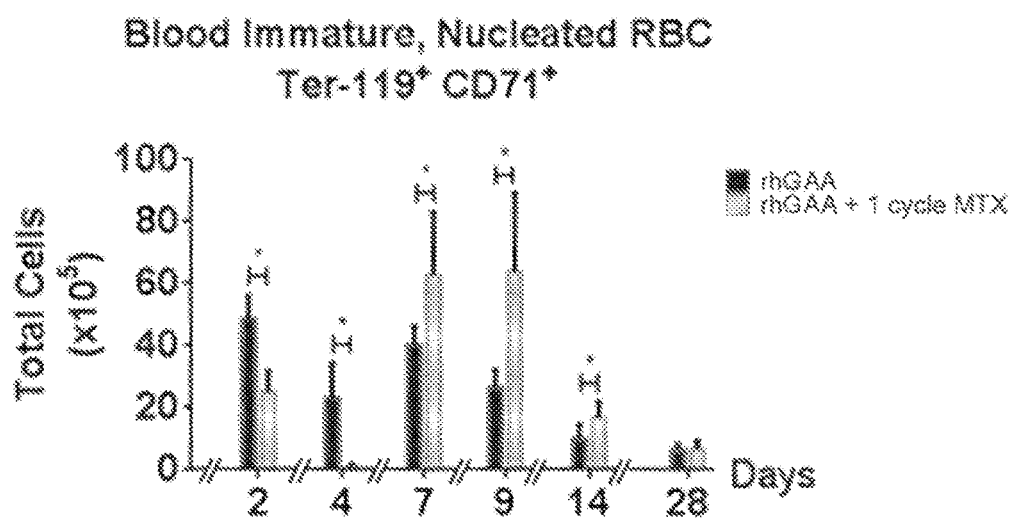
FIG. 5B shows numbers of immature, nucleated RBCs in the blood of mice on days 2, 4, 7, 9, 14 and 28 after rhGAA initiation Five to ten C57BL/6NTac mice/group were treated with rhGAA with and without a single cycle of low-dose methotrexate. The total numbers of erythroid cells were derived from a 25 μL aliquot of blood collected and examined by flow cytometry as described in Example 2. Mice were dosed with either rhGAA alone (rhGAA) of rhGAA concurrently with a single cycle of low-dose methotrexate (rhGAA+1 cycle MTX).

Erythroid Response Delayed in Blood Following Low-Dose Methotrexate Induction Regimen Examination of the blood compartment also showed significant depletion of total (FIG. 5A) and immature, nucleated RBCs (FIG. 5B) on day 2 in the single cycle low-dose methotrexate treated group. By day 4, immature, nucleated RBCs were nearly absent from the blood of the single cycle low-dose methotrexate treated group. By day 7, total RBCs were significantly reduced in the blood whereas immature, nucleated RBCs are significantly enriched. ft was on day 9 that total and immature, nucleated RBCs were significantly enriched in the blood. By day 14, a small but significant enrichment of immature, nucleated RBCs was seen in the blood of the single cycle low-dose methotrexate treated group which are absent by day 28.

Figure 5C:
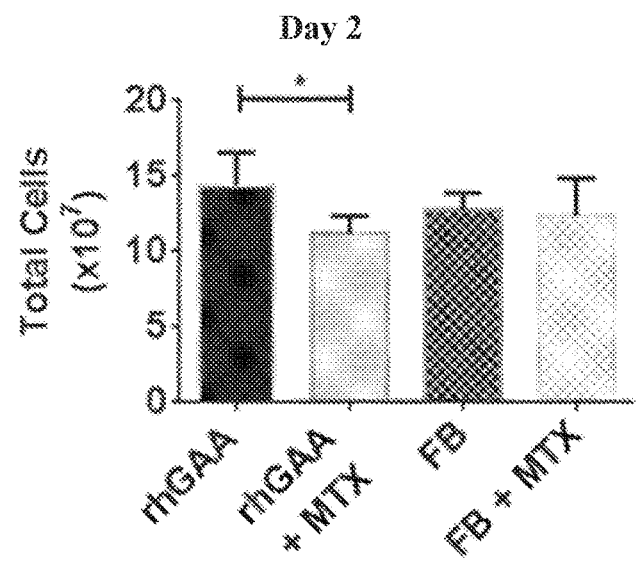
FIG. 5C shows numbers of total RBCs in the blood of mice on day 2.
Figure 5D:
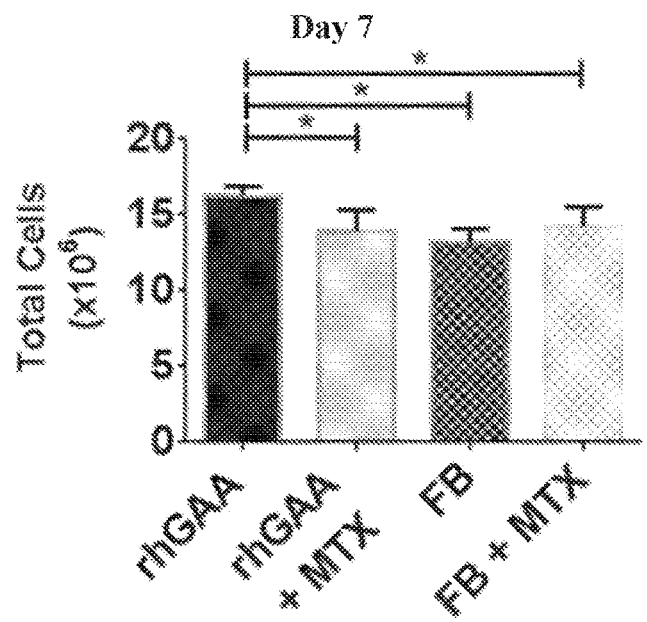
FIG. 5D shows numbers of total RBCs in the blood of mice on day 7.
Figure 5E:
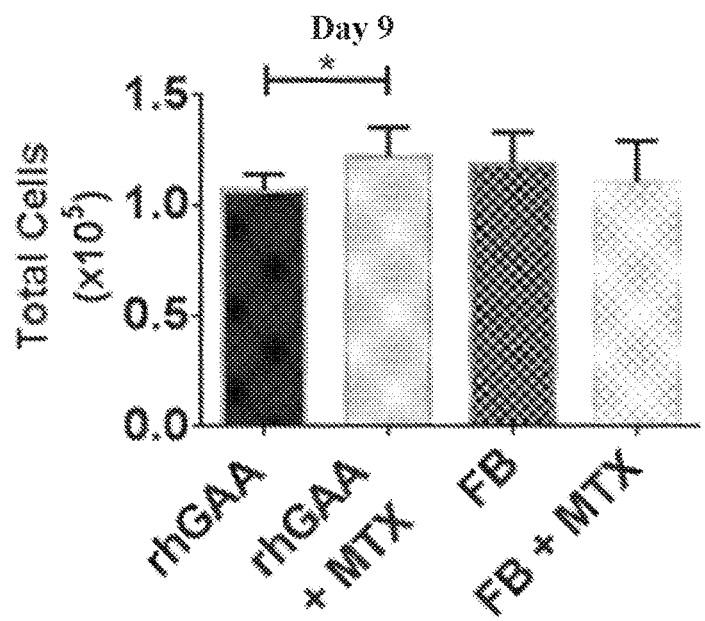
FIG. 5E shows numbers of total RBCs in the blood of mice on day 9.
Figure 5F:
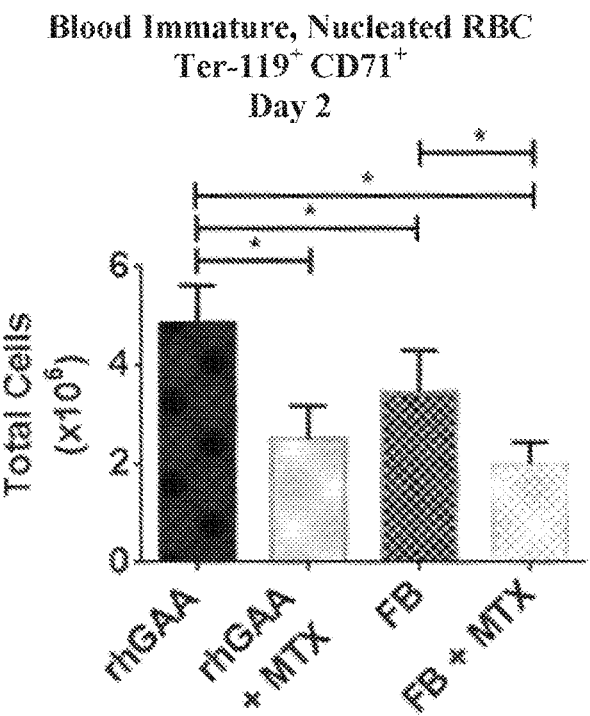
FIG. 5F shows numbers of immature, nucleated RBCs in the blood of Mice on day 2.
Figure 5G:
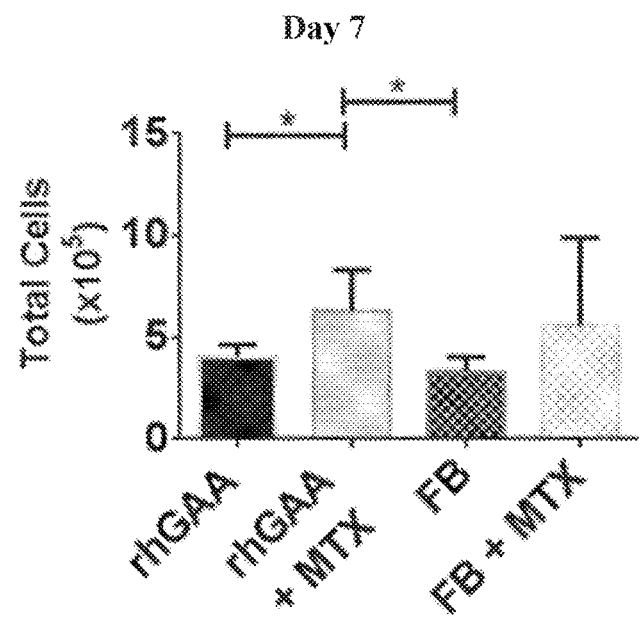
FIG. 5G shows numbers of immature, nucleated RBCs in the blood of mice on day 7.
Figure 5H:
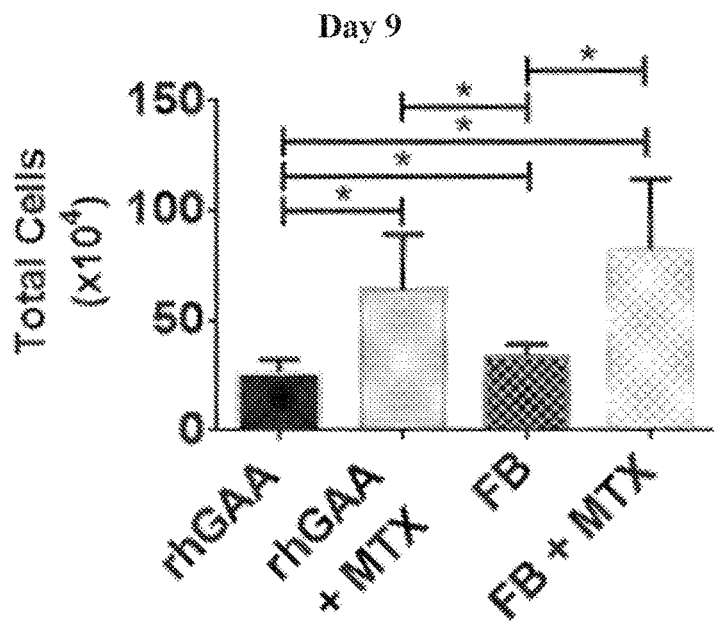
FIG. 5H shows numbers of immature, nucleated RBCs in the blood of mice on day 9. Experimental control groups of mice treated with FB with and without the exemplary transient lose dose methotrexate regimen were included. These data are from three or more separate experiments. Student t tests were performed and significance is noted as *≤0.05. Vertical bars represent standard deviation. The results demonstrated that the exemplary transient low-dose methotrexate regimen produces a similar but delayed RBC response in the systemic blood compartment as compared to that in the spleen.

The effect of transient low-dose methotrexate alone was also examined in the blood. When examining total RBCs, there were no observed differences between the methotrexate alone treated group and the group treated with vehicle control (FIGS. 5C-5E). However, the response of immature, nucleated RBCs in mice treated with a single cycle of low-dose methotrexate alone were similar to the response in mice treated with a single cycle of low-dose methotrexate with the rhGAA (FIGS. 5F-5H).

Figure 6A:
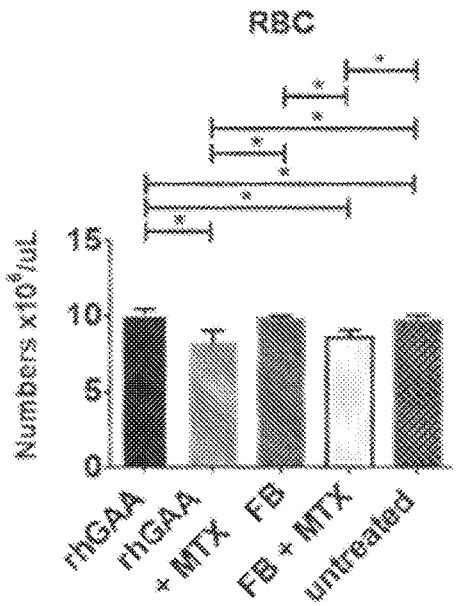
FIG. 6A shows total RBC counts in the systemic blood compartment of mice on day 7 after rhGAA initiation. FIG. GB shows hemoglobin level in the systemic blood compartment of mice on day 7 after rhGAA initiation.
Figure 6B:
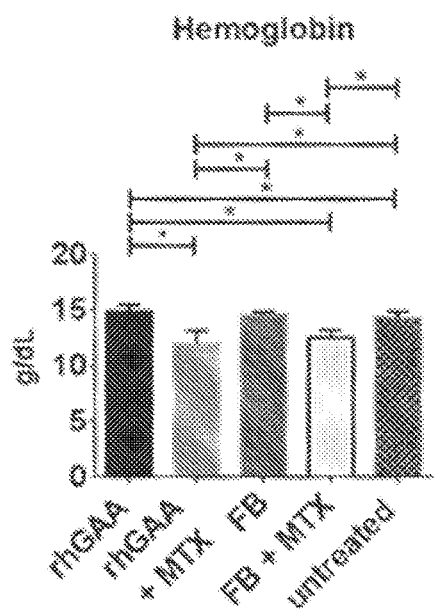
FIG. 6C shows percentage of hematocrit in the systemic blood compartment of mice on day 7 after rhGAA initiation.
FIG. 6D shows number of mature reticulocytes in the systemic blood. compartment of mice on day 7 after rhGAA initiation.
FIG. 6E shows frequency of mature reticulocytes in the systemic blood. compartment of mice on day 7 after rhGAA initiation.
FIG. 6F shows fraction of immature reticulocytes in the systemic blood. compartment of mice on day 7 after rhGAA. initiation. Six C57BL/6NTac mice/group were treated with rhGAA with and without a single cycle of low-dose methotrexate. Experimental control groups of mice treated with FB with and without the exemplary transient low-dose methotrexate regimen were included. Samples were collected by retro-orbital bleed into EDTA anticoagulant collection tubes and stored at 2-8° C. for no longer than 72 hours. CBC, WBC differential analysis and reticulocyte count were performed on Sysmex XT2000iV. Student t tests were performed and significance is noted as *≤0.05. Vertical bars represent standard deviation. The results demonstrate that the exemplary transient low-dose is methotrexate regimen generates a regenerative erythroid response on day 7 in the systemic blood compartment.
Figure 6C:
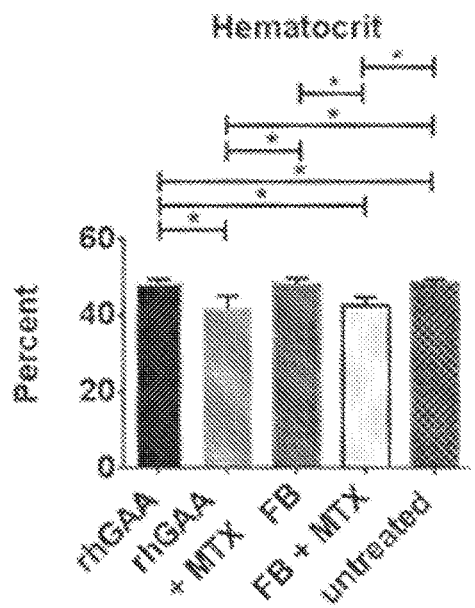
Figure 6D:
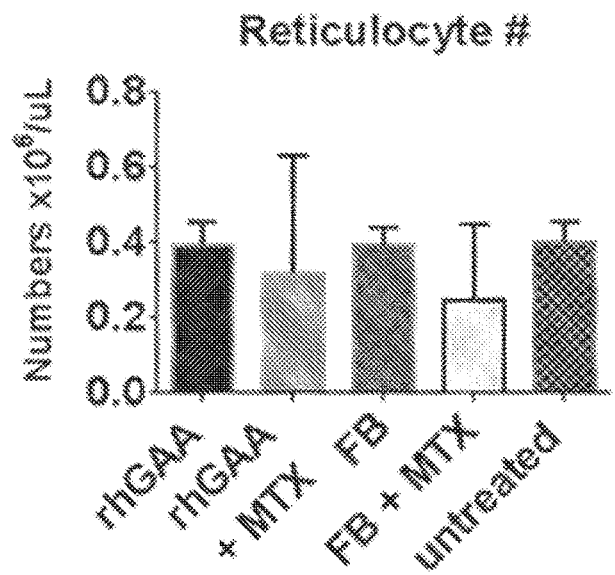
Figure 6E:
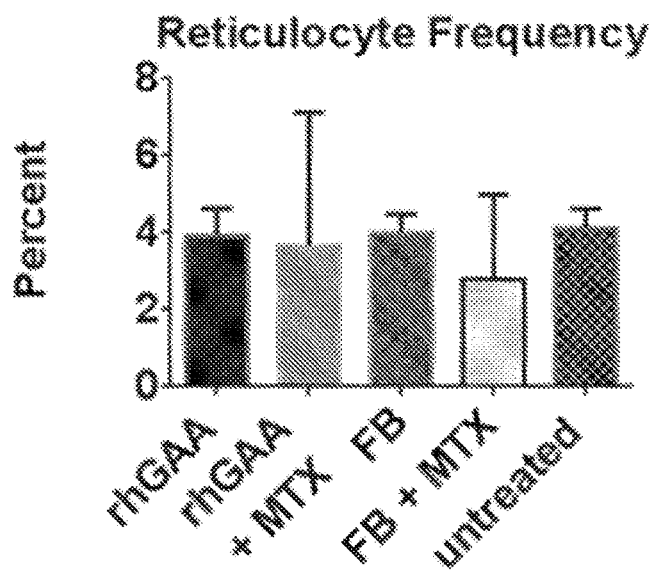
Figure 6F:
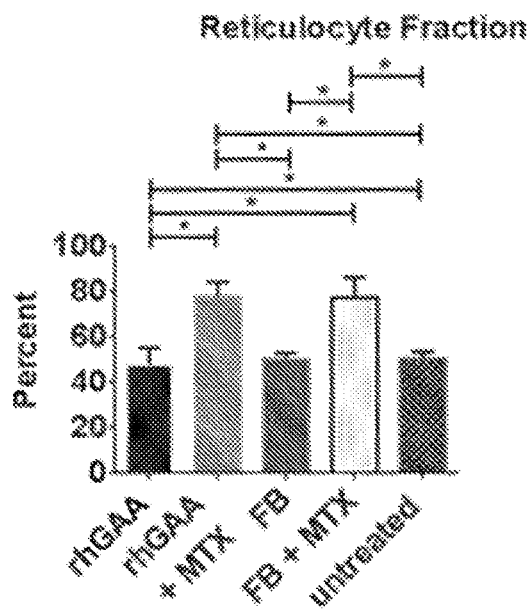

To confirm our findings, blood from mice 7 days after rhGAA initiation were examined on a Sysmex XT2000iV for a complete blood count (CBC) and reticulocyte count. Total RBC numbers were significantly reduced in the groups treated with transient low-dose methotrexate (FIG. 6A). Hemoglobin content (FIG. 6B) and hematocrit (FIG. 6C) were also significantly reduced in the groups treated with transient low-dose methotrexate. There were no observed differences in the frequency and numbers of mature reticulocytes (FIGS. 6D-6E). However, the frequency of the immature reticulocyte fraction (IRF) was significantly enriched in the groups treated with transient low-dose methotrexate (FIG. 6F).

Thus, the erythroid response is similar in the blood albeit delayed. Hematology analysis of the blood on day 7 after rhGAA initiation showed reduced total RBC count, hematocrit and hemoglobin in conjunction with an increased frequency in the immature reticulocyte fraction. This pattern is consistent with a regenerative erythroid response following erythrocyte loss.

Figure 7A:
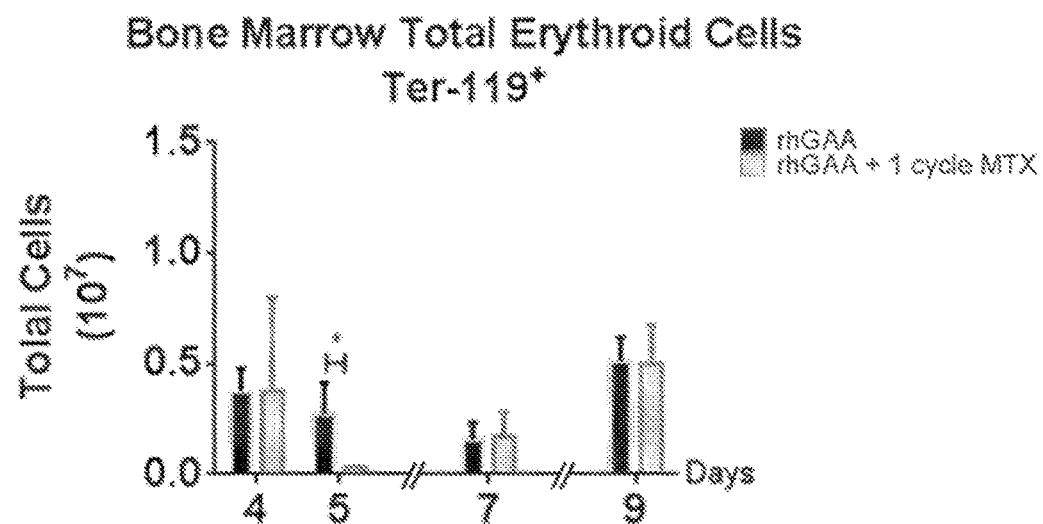
FIG. 7A shows numbers of total RBCs on days 4, 5, 7, and 9 in bone marrow samples of mice after rhGAA initiation as determined by flow cytometry.
Figure 7B:
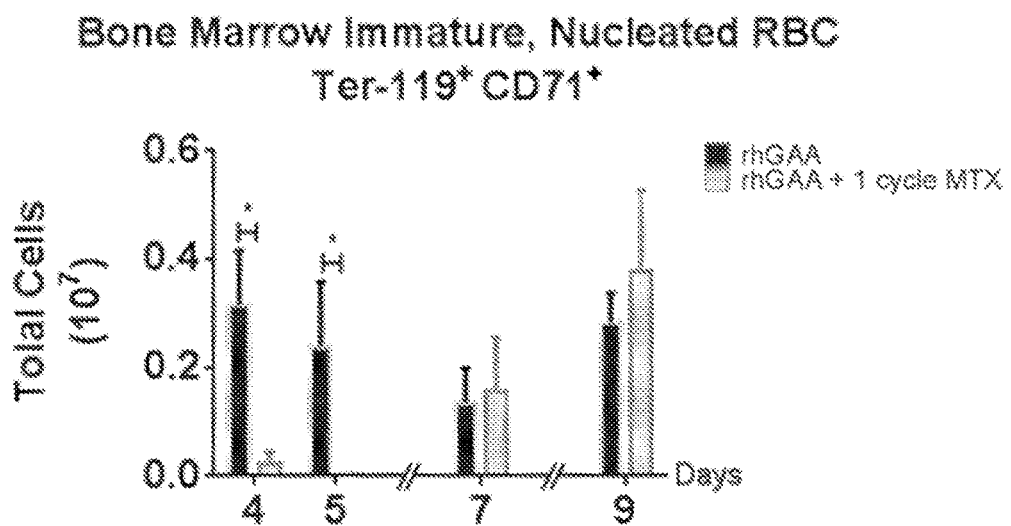
FIG. 7B shows numbers of immature, nucleated RBC subset on days 4, 5. 7, and 9 in bone marrow samples of mice after rhGAA initiation as determined by flow cytometry. Six C57BL/6NTac mice/ group were treated with rhGAA in the absence or presence of a single cycle of low-dose methotrexate. The total numbers of erythroid cells were derived from a single femur and examined by flow cytometry as described in Example 2. Mice were dosed with either rhGAA alone (rhGAA) or rhGAA concomitantly with a single cycle of low-dose methotrexate (rhGAA+1 cycle MIX). These data are from two separate experiments. Student t tests were performed and significance is noted as *≤0.05. Vertical bars represent standard deviation. The results demonstrated that the exemplary transient low-dose methotrexate regimen leads to an early, transient depletion of total and immature, nucleated RBCs, but the RBCs shortly return to homeostatic levels in the bone marrow.

Erythroid Cells are Depleted but Return to Homeostatic Levels in the Bone Marrow Following Low-Dose Methotrexate Induction Regimen Erythroid cell responses to single cycle low-dose methotrexate in the bone marrow showed no Differences in the Total RBCs on Day 4 when compared to mice given rhGAA alone (FIG. 7A). However, the immature, nucleated RBCs were significantly reduced on day 4 in the tolerized group (FIG. 7B). On day 5, both the total and immature, nucleated RBCs were significantly reduced in the tolerized group. By day 7 and 9, total and immature, nucleated RBCs showed no differences between tolerized mice and mice dosed with rhGAA alone. Thus, in the bone marrow, an early significant reduction of RBCs is also observed but the erythroid levels return to homeostatic levels by day 7.

Transient Low-Dose Methotrexate Induces Erythropoiesis in the Spleen

Figure 8A:
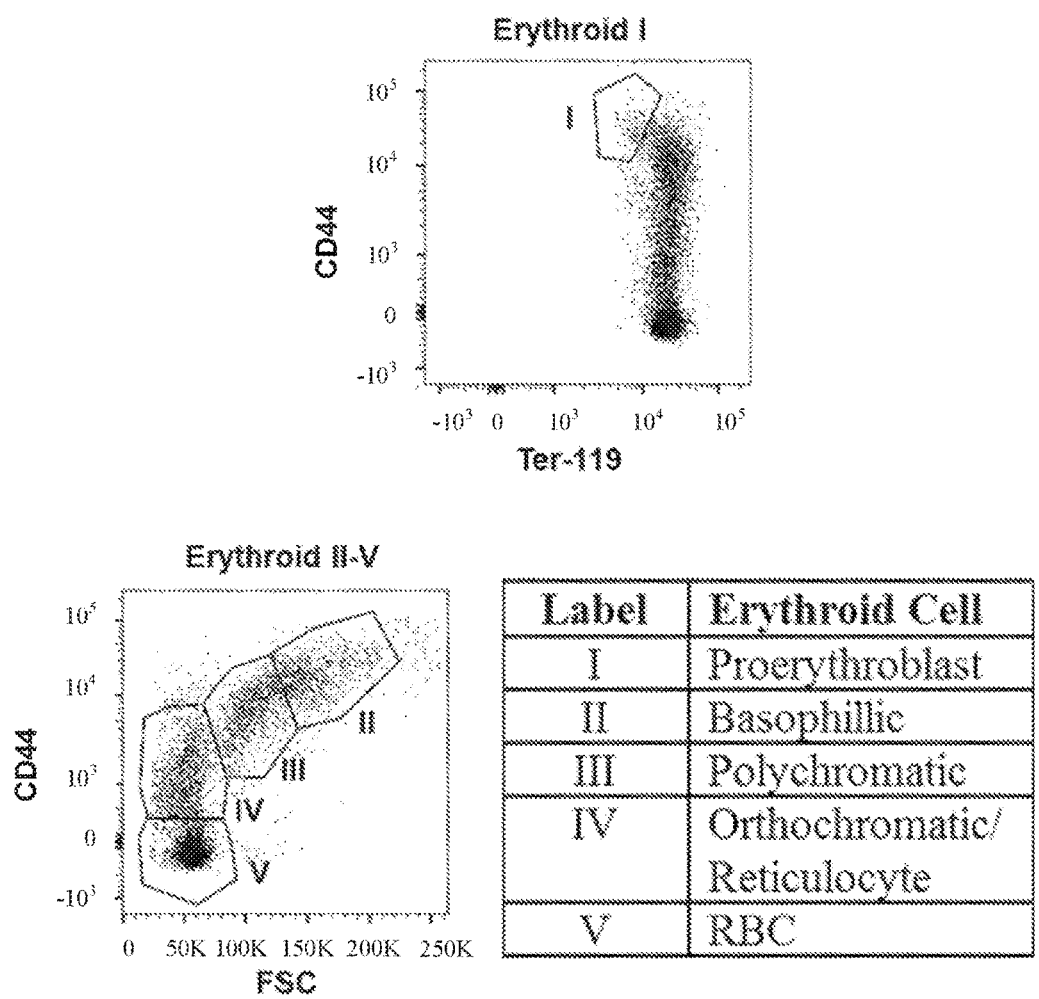
FIG. 8A shows the gating, strategy in flow cytometry to select for erythroid cells in different stages in development. Differential expression of CD44 and ESC (forward scatter)
Figure 8B:
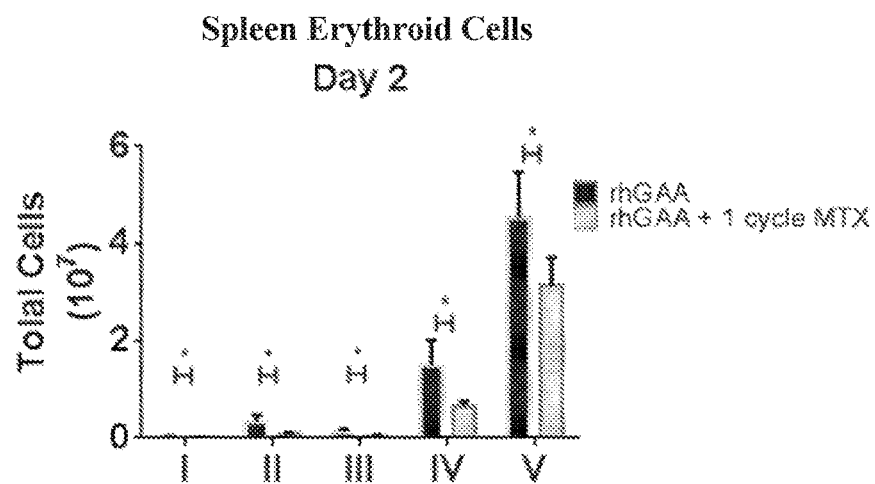
FIG. 8B shows the numbers of erythroid cells in spleen samples of mice on day 2 after rhGAA initiation.
Figure 8C:
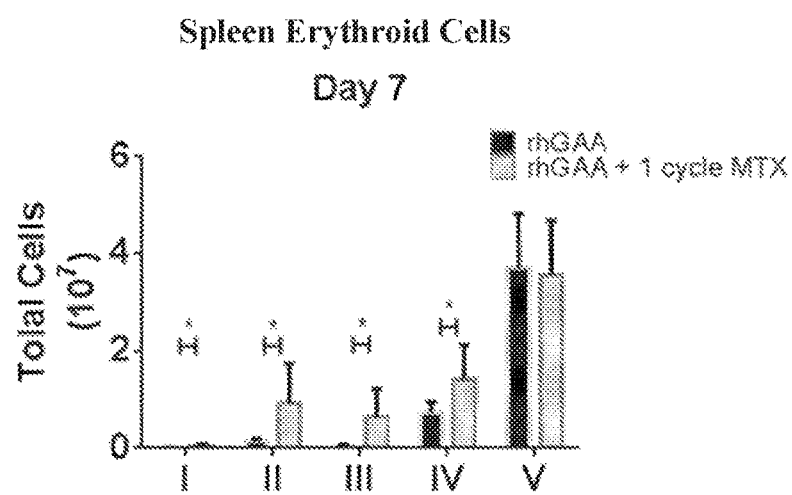
FIG. 8C shows the numbers of erythroid cells in spleen samples of mice on day 7 after rhGAA Each spleen sample was derived from a single homogenized spleen.

As shown in FIG. 8A, Differential expression of the adhesion molecule CD44 was utilized to examine the distinct stages of erythropoiesis from proerythroblasts to mature red blood cells during transient low-dose methotrexate ITI regimen. At day 2 after rhGAA initiation, all stages of early erythroid cells, including proerythroblasts, basophilic erythroblasts, polychromatic erythroblasts, orthothromatic erythroblasts and reticulocytes are significantly diminished in the single cycle low-dose methotrexate group in the spleen (FIG. 8B). Mature RBCs are also significantly reduced in the tolerized groups on day 2. At 7 days after rhGAA initiation, a significant enrichment of proerythroblasts, basophilic, polychromatic and orthochromatic erythroblasts as well as reticulocytes can be observed in the single cycle low-dose methotrexate group (FIG. 8C. There are no differences in mature RBCs on day 7 in the spleen. The enrichment of immature, nucleated RBCs at day 7 following rhGAA initiations in the spleen coincides with the enrichment of multiple B cell populations capable of conferring immune tolerance in recipient naïve mice, namely B10 regulatory B cells, follicular B cells, and B cells that express Foxp3, TGF-β, and IL-10 (Joly et. al., 2014).

Figure 8D:
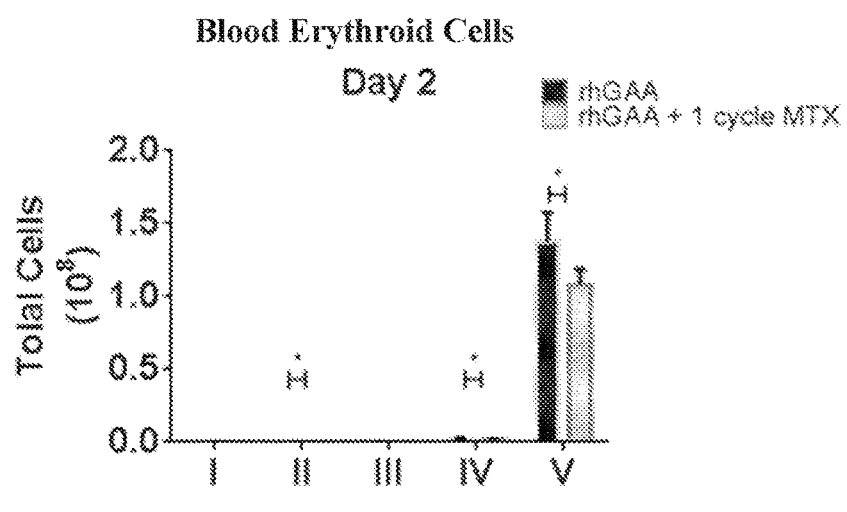
FIG. 8G shows the numbers of erythroid cells in bone marrow samples of mice on day 5 after rhGAA initiation.
FIG. 8I shows the numbers of erythroid cells in bone marrow samples of mice on day 9 after rhGAA. initiation. Each bone marrow sample was derived from a single femur. Five to ten C57BL/6NTac mice/group were treated with rhGAA fifteen minutes within a single cycle of low-dose methotrexate. Mice were dosed with either rhGAA alone (rhGAA) or rhGAA together with a single cycle of low-dose methotrexate (rhGAA+1 cycle MTX). These data are from two or more separate experiments. Student t tests were performed and significance is noted as *≤0.05. Vertical bars represent standard deviation. The results demonstrated that erythropoiesis triggered by the exemplary transient low-dose methotrexate regimen dominantly occurs in the spleen of mice.
Figure 8E:
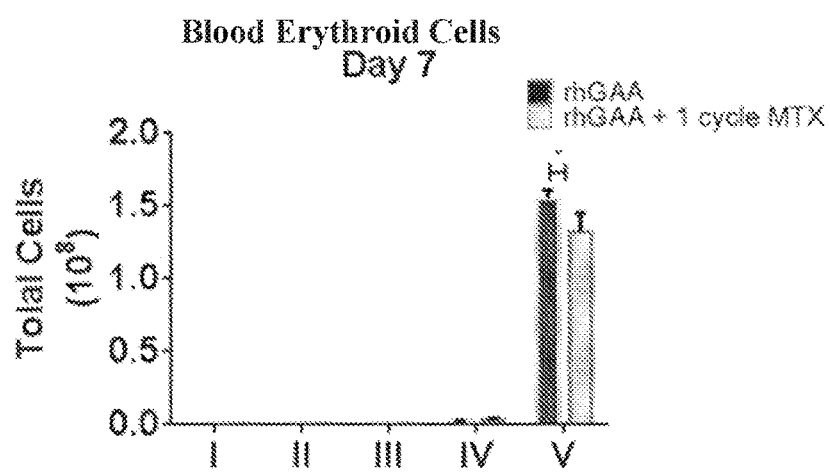

In the blood, a small but significant reduction in basophilic erythroblasts, orthochromatic erythroblasts, reticulocytes and mature red blood cells can be observed on day 2 after rhGAA initiation in the single cycle lose-dose methotrexate group (FIG. 8D). However, no changes in immature, nucleated RBCs are observed on day 7 after rhGAA initiation in the blood (FIG. 8E). On day 7, a significant reduction in mature RBCs can be observed in the blood of tolerized mice.

Figure 8F:
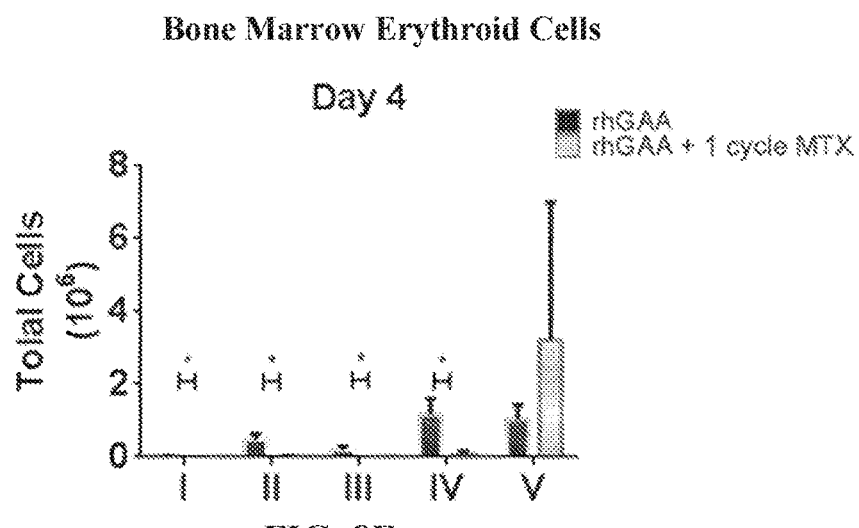
Figure 8G:
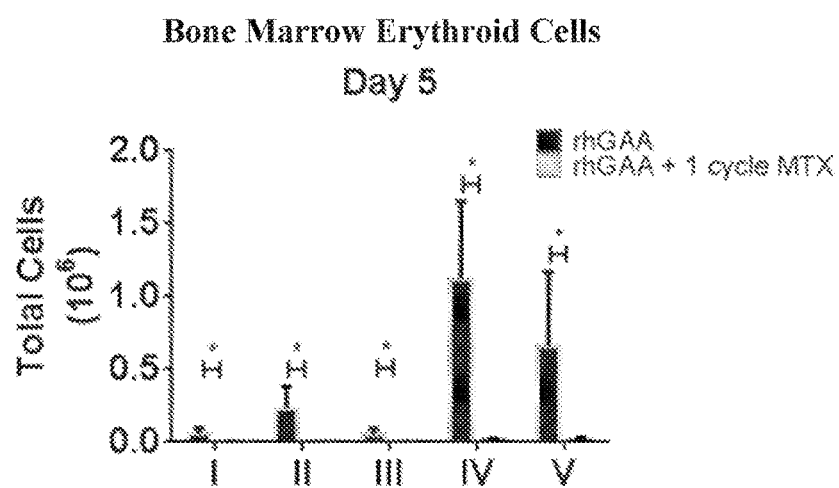
Figure 8H:
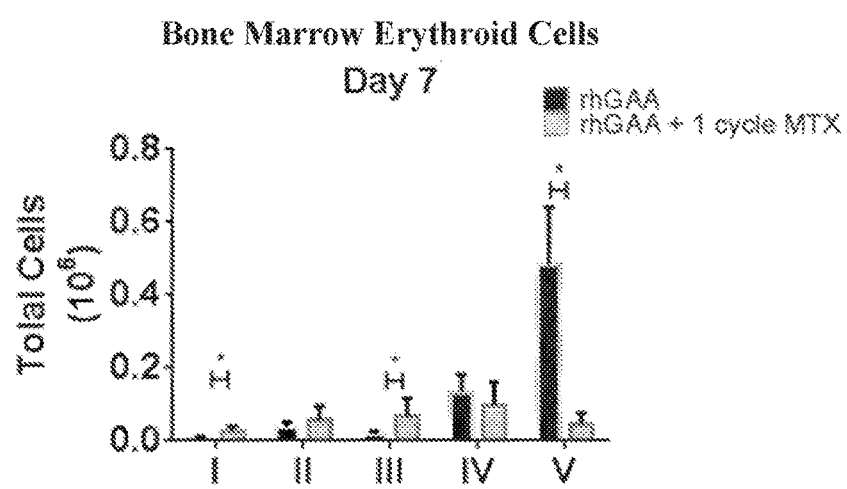
Figure 8I:
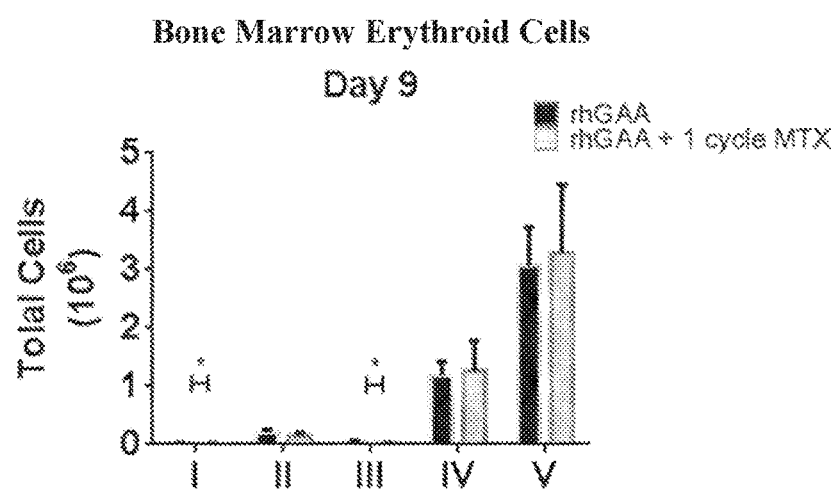

The bone marrow shows a significant depletion in all stages of early erythroid including proerythroblasts, basophilic erythroblasts, polychromatic erythroblasts, orthochromatic erythroblasts and reticulocytes on day 4 after rhGAA initiation in the transient low-dose methotrexate group but no statistically significant differences in mature RBCs (FIG. 8F). Depletion in all erythroid cell stages, including early and mature RBCs, could be observed on day 5 in the tolerized group (FIG. 8G). By day 7, a small but significant enrichment of proerythroblasts and. polychromatic erythroblasts can be observed in the tolerized group (FIG. 8H). However, the mature RBCs are significantly reduced in the tolerized group. On day 9, a small but significant enrichment of proerythroblasts and polychromatic erythroblasts can be observed in the tolerized group but there are no differences in mature RBCs in the bone marrow between groups (FIG. 8I).

Figure 9A:
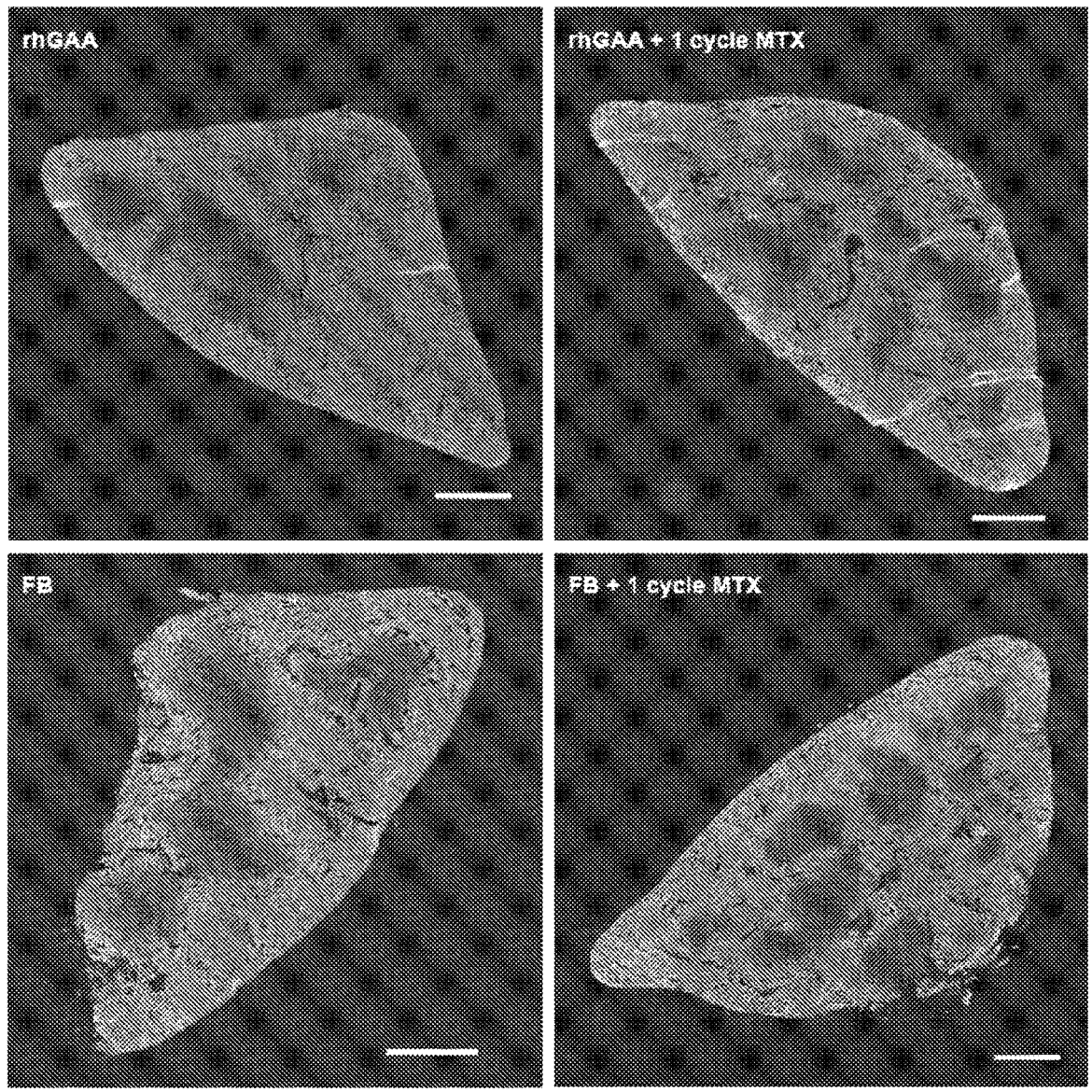
FIG. 9A shows that the exemplary transient low-dose methotrexate regimen increases appearance of nucleated cells (including hematopoietic precursors) in splenic red pulp. Four to six C57BL/6NTac mice/group were treated with rhGAA with and without a single cycle of low-dose methotrexate. Experimental control groups of mice treated with FB with and without the exemplary transient low-dose methotrexate regimen were included. Splenic samples were collected 7 days after rhGAA initiation and processed for immunofluorescence. Splenic samples were collected 7 days after rhGAA initiation and subjected to cryosectioning in OCT medium, immunofluorescence staining for CD71 and Ter-119 and analysis on AxioScan slide scanner (Carl Zeiss; Peabody, MA) configured for multi-channel fluorescence imaging and equipped with a PlanApo 20x, 0.8NA objective. (A) Shown were representative whole slide scans in which CD71 immunofluorescence staining was shown in red (PE) and TER119 in green (FITC). Samples were also stained with DAPI (blue) to visualize nuclei. Areas devoid of CD71 or Ter-119 staining represent white pulp. Areas with CD71 and/or Ter-119 staining represent red pulp. Scale bars represent 500 µm.
Figure 9B:
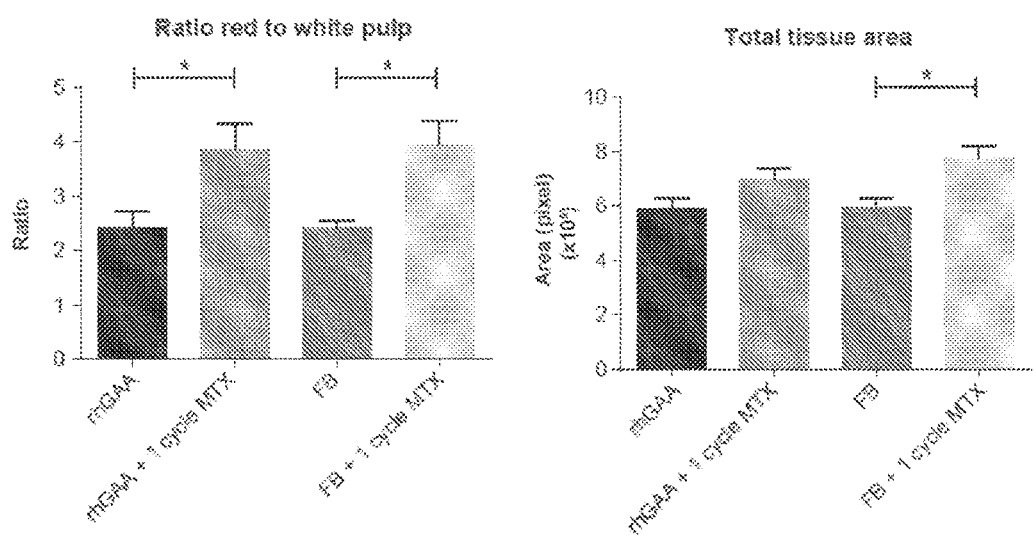
FIG. 9B shows graphical representation of the results of the morphometric quantification of red to white pulp area ratio (top) and total tissue area (bottom). Vertical bars represent the standard error of mean (SEM) with Bonferroni adjusted p values where *≤0.05.

Frequency of Nucleated Cells are Increased in the Splenic Red Pulp of Tolerized Mice The enlarged spleen in mice given transient low-dose methotrexate suggested a possible change in spleen morphology. To evaluate this, mice were given rhGAA with and without transient low-dose methotrexate (e.g., ITI regimen) and spleens were collected 7 days after rhGAA initiation. Microscopic evaluation of the spleen revealed significantly increased red pulp area relative to the white pulp area in mice given transient low-dose methotrexate when compared to mice given rhGAA alone (FIGS. 9A-9B). Mice given transient low-dose methotrexate with FB similarly exhibited significantly increased red pulp area relative to the white pulp area when compared to mice given FB alone. The nucleated cells are likely hematopoietic precursuors as suggested by the cellular studies using flow cytometry.

Figure 10:
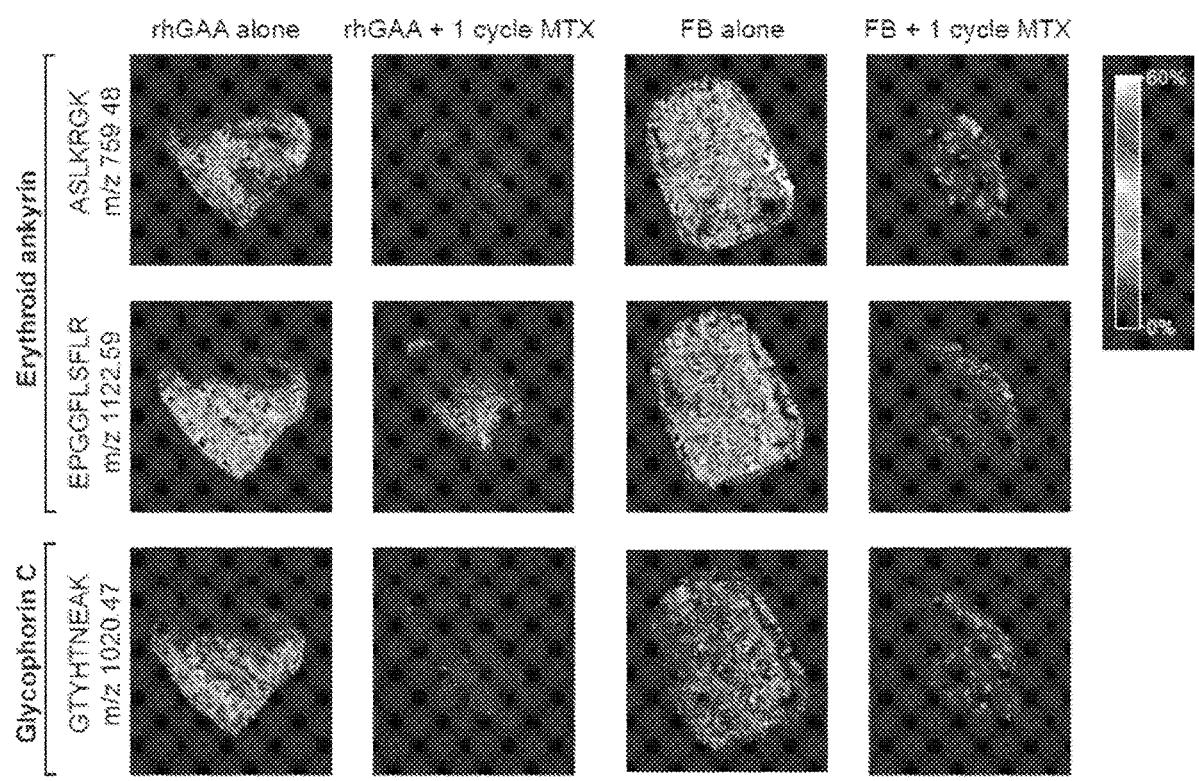
FIG. 10 shows that the proteins erythroid ankyrin and glycophorin C are diminished in the spleen of mice treated with the exemplary transient low-dose methotrexate regimen. Four to six C57BL/6NTac mice/group were treated with rhGAA with and without a single cycle of low-dose methotrexate. Experimental control groups of mice treated with FB with and without the exemplary transient low-dose methotrexate regimen were included. Splenic samples were collected 7 days after rhGAA initiation and processed for tissue mass spectrometry imaging. Shown is 10 µM splenic section exhibiting signal for erythroid ankyrin and glycophorin C. Spatial resolution is 30 µM.

Appearance of Proteins Associated to Mature RBCs are Reduced in Spleen of Tolerized Mice The spatial distribution of proteins in the spleen was examined by tissue mass spectrometry imaging. Mice were treated with rhGAA in the presence and absence of methotrexate as described above. Experimental control groups of mice treated with FB buffer with and without methotrexate were included. Spleens were collected 7 days after rhGAA initiation and frozen en bloc. Examination of 10 μM spleen sections shows the protein erythroid ankyrin and glycophorin C to be evenly distributed across the spleen in the groups treated with rhGAA. alone or with FB (FIG. 10). In the groups given rhGAA or FB together with transient low-dose methotrexate regimen, the erythroid ankyrin and glycophorin C signal diminished. Erythroid ankyrin and glycophorin C are erythroid-specific proteins that are highly expressed in mature RBCs (Chen et. al., 2009). The reduction of these proteins is consistent with the temporary loss of mature RBCs followed by generation of new RBCs in the spleen due to transient low-dose methotrexate ITI regimen.

Example 3

Erythroid Cell Transfusion from Tolerized Mice to Naïve Mice

Introduction

To determine whether total erythrocytes, which include immature, nucleated RBCS and mature RBCs, from tolerized mice could confer immune tolerance, erythrocyte transfusion studies were performed to transfuse erythrocytes from mice treated with rhGAA with and without transient low-dose methotrexate into nave mice. Immune tolerance was assessed by measuring anti-rhGAA antibody titers in the serum of naive mice receiving the erythrocyte transfusion.

Materials and Methods

Serum Anti-rhGAA Antibody Titers

Quantitation of anti-rhGAA antibody titers from mouse serum was measured by ELBA as previously described (holy, Martin et. al. 2014). Briefly, 96-well plates (Corning catalog 29442-322) were coated overnight (5 mg/mL rhGAA m sodium acetate buffer, pH 5.0), treated with blocking reagent (0.1% BSA in PBS), and incubated with serial dilutions of mouse serum in duplicate (1 hour at 37° C.). After a wash, samples were treated with HRP-conjugated goat anti-mouse IgG secondary antibody (Southern Biotechnology Associates catalog 1030-05), washed, and developed by addition of TMB (3,3′,5,5′-tetramethylbenzidine) substrate (BioFX Laboratories catalog TMBW-1000-01) for 15 minutes at room temperature. The reaction was stopped by addition of 1 N HCl and absorbance was immediately measured at 450/650 nm on a SpectraMax M2 (Molecular Devices). End-point titers were derived from the reciprocal of the sample dilution resulting in an absorbance value of 0.2.

Erythroid Cell Transfusion

Harvest of erythroid cells from age-matched, gender-matched donor mice performed on day 7 (erythroid cell isolation from spleen) and day 9 (erythroid cell isolation from blood) after rhGAA treatment with and without a single cycle of transient low-dose methotrexate ITI regimen as described above. Blood and spleen were aseptically collected and processed as described above. Blood was collected into sterile EDTA Monoject blood collection tubes (Covidien catalog 8881311149). Pooled blood was passed through a murine adapted Acrodisk PSE 25-mm WBC filter with Leukosorb media (Pall catalog AP-4851) for leukoreduction. Erythroid cells from pooled spleen samples were isolated with mouse anti-Ter-119 MicroBeads (Miitenyi Biotec catalog 130-049-901) by positive selection per manufacturer's instructions. Purified erythroid cells from blood (≥99.9%, verified by flow cytometry) and from spleen (≥93.3%, verified by flow cytometry) were washed in sterile PBS. Purified erythroid cells were injected into recipient mice by i.v. tail vein administration. Mice received weekly doses of rhGAA after prophylactic administration of diphenhydramine as described above. Bi-weekly blood collection was performed by retro-orbital bleeds into EDTA anticoagulant Capiject micro collection tubes as described above. Sera were collected for evaluation of anti-rhGAA antibody titers by ELISA.

Results

Figure 11A:
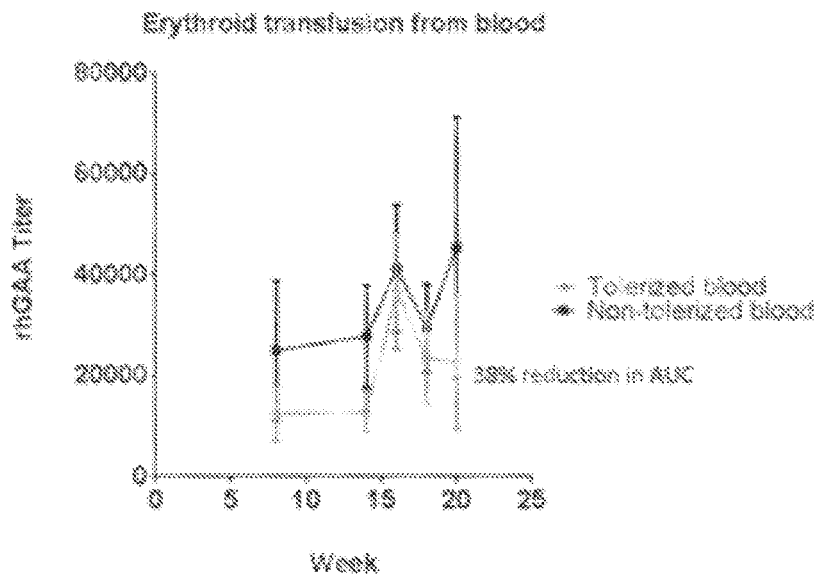
FIGS. 11A-11C shows serum anti-rhGAA antibody titers in mice receiving 200 million total erythrocytes from the blood of donor mice. Splenic immature, nucleated RBC's isolated from mice treated with transient low-dose methotrexate ITI regimen 7 days after rhGAA initiation appear to display a trend of immune tolerance induction in naive mice. Total erythroid cells were isolated from mice treated with rhGAA with (tolerized mice) and without (non-tolerized mice) transient low-dose methotrexate ITI regimen into nave recipient mice. After the transfusion and weekly thereafter, recipient mice were dosed with i.v. rhGAA. Subsequent doses of rhGAA were accompanied by a prophylactic dose of diphenhydramine. Serum was collected for evaluation of anti-rhGAA IgG antibody titers by ELISA.
Figure 11B:
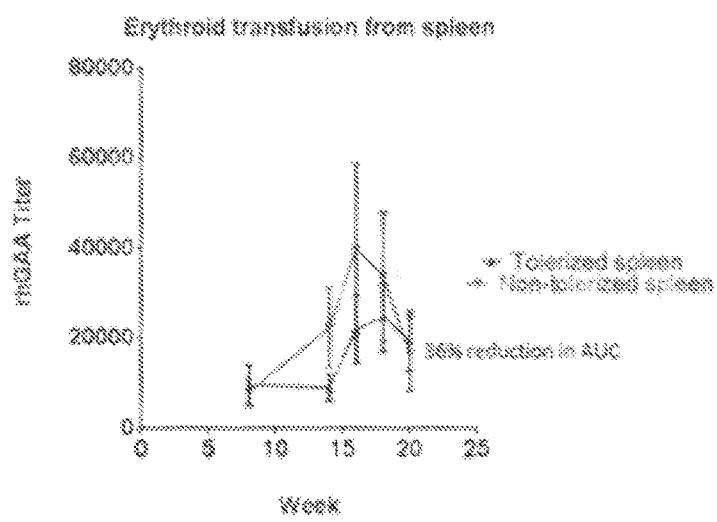
Figure 11C:
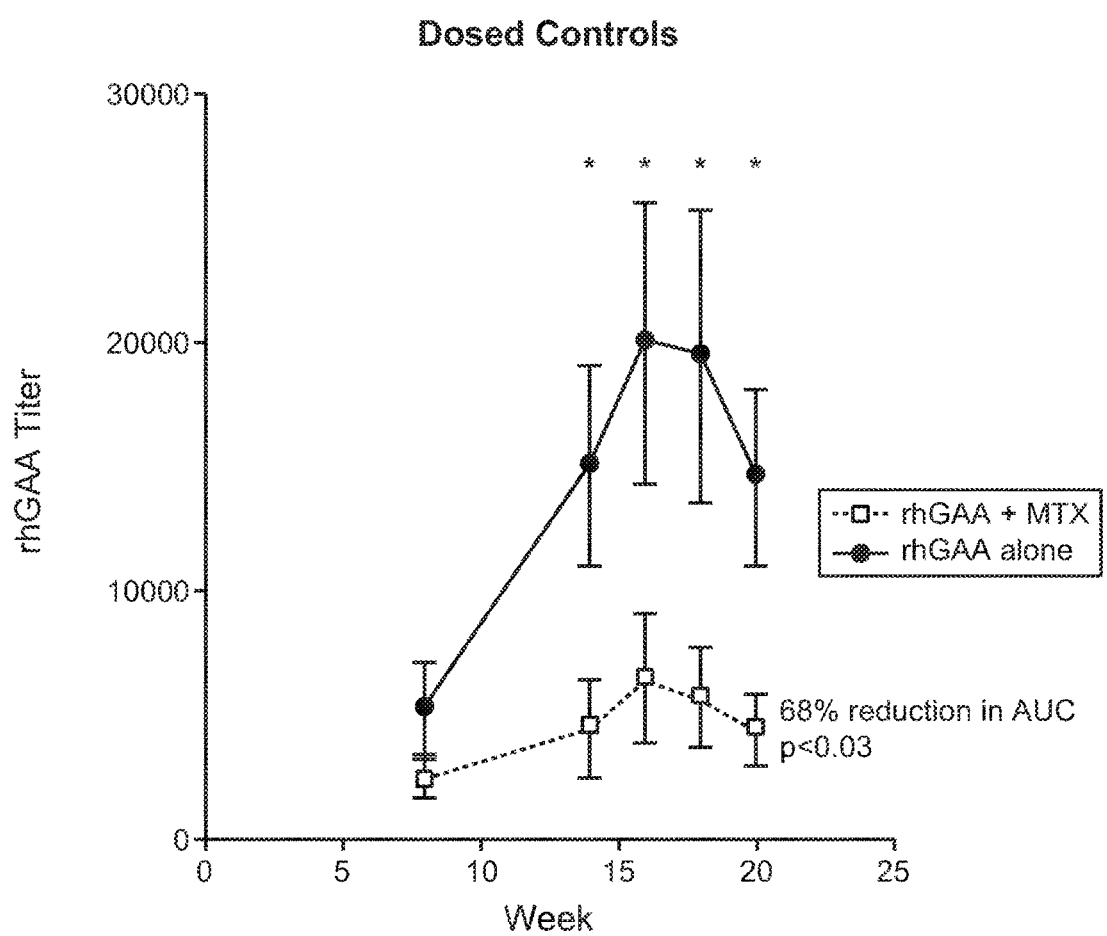

Splenic Immature, Nucleated RBCs Isolated from Tolerized Mice to rhGAA by Methotrexate Confers Immune Tolerance To Naïve Mice Transfusion of erythroid cells from mice treated with rhGAA. with and without transient low-dose methotrexate ITI regimen were performed in naive mice to determine whether total erythroid cells, which include immature, nucleated RBC's and mature RBC's, could confer immune tolerance. 75 million erythroid cells (≥93.3%) from the spleen of donor mice, 7 days after rhGAA initiation, or 200 million donor erythrocytes purified from blood (≥99.9%), 9 days after rhGAA initiation, were delivered into naïve recipient Mice. After the transfusion and weekly thereafter, recipient mice were dosed with i.v. rhGAA. Serum was collected hi-weekly through the twentieth week for evaluation of anti-rhGAA IgG antibody titers by ELISA (FIGS. 11A-11C). In the dosed controls (FIG. 11C), the titers for weeks 14, 16, 18 and 20 and the area under the curve (AUC; 38% reduction in AUC) were significantly reduced in the group treated with rhGAA with transient low-dose methotrexate ITI regimen (rhGAA+MTX) when compared to the group treated with rhGAA alone. A trend of reduced titers for weeks 14. 15, 18 and 20 and reduced AUC were observed for mice that received total erythrocytes from blood (tolerized blood, 38% reduction in AUC) (FIG. 11A) or spleen (tolerized spleen, 36% reduction in AUC) (FIG. 11B) from donor mice that were treated with rhGAA in combination with transient low-dose methotrexate ITI regimen. Statistical significance was assessed by removing an outlier (highest rhGAA titer value) from each group and comparing the AUC difference between the respective groups.

To determine whether total erythroid cells from mice treated with rhGAA in combination with transient low-dose methotrexate ITI regimen could confer immune tolerance, transfusion studies were carried out into naive recipient mice. Historical data has shown groups treated rhGAA with transient low-dose methotrexate ITI regimen have significantly reduced rhGAA titers and AUC when compared to groups treated with rhGAA. alone. However, no differences were observed between groups in the dosed control groups, possibly due to a high outlier (data not shown). Significance differences between groups were observed when the outlier was removed. To avoid bias, a high outlier was removed from each group. Transfusion studies suggest total isolated erythroid cells from donor mice treated with rhGAA in combination with transient low-dose methotrexate ITI regimen appear to show a trend of conferred immune tolerance to nave recipient mice whether isolated from blood or spleen. The transfusion study was performed once.

REFERENCES

Allman, D., B. Srivastava and R. C. Lindsley (2004). "Alternative routes to maturity: branch points and pathways for generating follicular and marginal zone B cells." *Immunol Rev* 197: 147-460.

Banugaria, S. G., S. N. Prater, T. T. Patel, S. M. Dearmey, C. Milleson, K. B. Sheets, D. S. Bali, C. W. Rehder, J. A. Raiman, R. A. Wang, F. Labarthe, J. Charrow, P. Harmatz, P. Chakraborty, A. S. Rosenberg and P. S. Kishnani (2013). "Algorithm for the early diagnosis and treatment of patients with cross reactive immunologic material-negative classic infantile Pompe disease: a step towards improving the efficacy of ERT." *PLoS One* 8(6): e67052.

Burrow, T. A., Y. Sun, C. E. Prada, L. Bailey, W. Zhang, A. Brewer, S. W. Wu, K. D. Setchell, D. Witte, M. B. Cohen and G A. Grabowski (2015). "CNS, lung, and lymph node involvement in Gaucher disease type 3 after 11 years of therapy: clinical, histopathologic, and biochemical findings." *Mol Genet Metal* 114(2): 233-241.

Chen, K., J. Liu, S. Heck, J. A. Chasis, X. An and N. Mohandas (2009). "Resolving the distinct stages in erythroid differentiation based on dynamic changes in membrane protein expression during erythropoiesis." *Proc Natl Acad Sci USA* 106(41): 17413-17418.

Collins, P. W., M. Mathias, J. Hanley, D. Keeling, R. Keenan, M. Laffan, D. Perry, R. Liesner and U. K. H. C. D. Organisation (2009). "Rituximab and immune tolerance in severe hemophilia A: a consecutive national cohort." *J Thromb Haemost* 7(5): 787-794.

Cremel, M., N. Guerin, G Cainpello, Q. Bartle, W. Berlier, F. Horand and Y. Godfrin (2015). "Innovative approach in Pompe disease therapy: Induction of immune tolerance by antigen-encapsulated red blood cells." *Int J Pharm* 491(1-2): 69-77.

Cremel, M., N. Guerin, F. Morand, Bann and Y. Godfrin (2013). "Red blood cells as innovative antigen carrier to induce specific immune tolerance." *Int J Pharm* 443(1-2): 39-49.

Cronstein, B. N. (2005). "Low-dose methotrexate: a mainstay in the treatment of rheumatoid arthritis." *Pharmacol Rev* 57(2): 163-472.

Daugas, E., C. Cande and G. Kromer (2001). "Erythrocytes: death of a mummy." Cell Death Differ 8(12): 1131-1133.

Dong, H. Y., S. Wilkes and H. Yang (2011). "CD71 is selectively and ubiquitously expressed at high levels in erythroid precursors of all maturation stages: a comparative immunochemical study with glycophorin A and hemoglobin A." *Am J Sur Pathol* 35(5): 723-732.

Elahi, S., J. M. Ertelt, J. M. Kinder, T. T. Jiang, X. Zhang, L. Xin, Chaturvedi, B. S. Strong, J. E. Qualls, K. A. Steinbrecher, T. A. Kalfa, A. F. Shaaban and S. S. Way (2013). "Immunosuppressive CD71+erythroid cells compromise neonatal host deference against infection." *Nature* 504(7478): 158-162.

Ernst, R B., J. C. Garrison and L. F. Thompson (2010). "Much ado about adenosine: adenosine synthesis and function in regulatory T cell biology." *J Immunol* 185(4): 1993-1998.

Franchini, N I, C. Mengoli., G. Lippi, G. Targher, M. Montagnana, G. L. Salvagno, M. Zaffanello and M. Cruciani. (2008). "Immune tolerance with rituximab in congenital haemophilia with inhibitors: a systematic literature review based on individual patients analysis." Haemophilia. 14(5): 903-912.

Garman, R D., K. Munroe and S. M. Richards (2004). "Methotrexate reduces antibody responses to recombinant human alpha-galactosidase A therapy in a mouse model of Fabry disease." *Clin Exp Immunol* 137(3): 496-501

Getts, D. R, D. P. McCarthy and S. D. Miller (2013). "Exploiting apoptosis for therapeutic tolerance induction." *J Immunol* 191(11): 5341-5346.

Grimm, A. J., S. Kontos, G. Diaceri, X. Quaglia-Thermes and J. A. Hubbell (2015). "Memory of tolerance and induction of regulatory T cells by erythrocyte-targeted antigens." *Sci Rep* 5: 15907.

Han, K. L., S. V. Thomas, S. M. Koontz, C. M. Changpriroa, S. K. Ha, H. L. Malech and E. M. Kang (2013). "Adenosine A(2)A receptor agonist-mediated increase in donor-derived regulatory T cells suppresses development of graft-versus-host disease." *J Immunol* 190(1): 458-468.

Joly, M. S., R. P. Martin, S. Mitra-Kaushik, L. Phillips, A. D'Angona, S. M. Richards and A. M. Joseph (2014). "Transient low-dose methotrexate generates B regulatory cells that mediate antigen-specific tolerance to alglucosidase alfa." *J Immunol* 193(8): 3947-3958.

Joseph, A., K. Munroe, M. Housman, R. Garman and S. Richards (2008). "Immune tolerance induction to enzyme-replacement therapy by co-administration of short-term, low-dose methotrexate in a murine Pompe disease model." *Clin Exp Immunol* 152(1): 138-146.

Joseph, A., K. Neff, J. Richard, L. Gao, D. Bangari, M. Joly, K. Culm-Merdek, K. Garman, J. Williams, S. Richards and M. Ruzek (2012). "Transient low-dose methotrexate induces tolerance to murine anti-thymocyte globulin and together they promote long-term allograft survival." *J Immuno*1 189(2): 732-743.

Kina, T., K. Ikuta, E. Takayama, K. Wada, A. S. Majumdar, I. L. Weissman and Y. Katsura (2000). "The monoclonal antibody TER-119 recognizes a molecule associated with glycophorin A and specifically marks the late stages of murine erythroid lineage." *Br J Haematol* 109(2): 280-287.

Kishnani. P. S., D. Corzo, M. Nicolino, B. Byrne, H. Mandel, W. L. Hwu, N. Leslie, J. Levine, C. Spencer, M. McDonald, J. Li, J. Dumontier, M. Halberthal, Y. H. Chien, R Hopkin, S. Vijayaragha.van, D. Gruskin, D. Bartholomew, A. van der Ploeg. J. P. Clancy, Parini, G. Morin, M. Beck, G. S. De la Gastine, M. Jokic, B. Thurberg, S. Richards, D. Bali, M. Davison, M. A. Wordeti, Y. T. Chen and J. E. Wraith (2007). "Recombinant human acid [alpha]-glucosidase: major clinical benefits in infantile-onset Pompe disease." *Neurology* 68(2): 99-109.

Kontos, S., I. C. Kourtis, K. Y. Dane and J. A. Hubbell (2013). "Engineering antigens for in situ erythrocyte binding- induces T-cell deletion." *Proc Natl Acad Sci USA* 110(1): E60-68.

Koulnis, M., R. Pop, E. Porpiglia, J. R. Shearsione,11 Hidalgo and M. Socolovsky (2011). "Identification and analysis of mouse erythroid progenitors using the CD71/ TER119 flow-cytometric assay." *J Vis Exp* (54).

Kremer, J. M. (2004). "Toward a better understanding of methotrexate." *Arthritis Rheum* 50(5): 1370-1382.

Lorentz, K. M., S. Kontos, G. Diacert, H. Henry and J. A. Hubbell (2015). "Engineered binding to erythrocytes induces immunological tolerance to *E. coli* asparaginase." *Sci Adv* 1(6): e1500112.

Mendelsohn, N. J., Y. H. Messinger, A. S. Rosenberg and P. S. Kishnani (2009). "Elimination of antibodies to recombinant enzyme in Pompe disease." *N Engl J Med* 360(2): 194-195.

Messinger, Y. H., N. J. Mendelsohn, W. Rhead, D. Dimmock, E. Hershkovitz, M. Champion, S. A. Jones, K Olson, A. White, C. Wells, D. Bali, L. E. Case, S. P. Young, A. S. Rosenberg and P. S. Kishnani (2012). "Successful immune tolerance induction to enzyme replacement therapy in CRIM-negative infantile Pompe disease." *Genet Med* 14(1): 135-142.

Nandalcumar, S. K., J. C. Ulirsch and V. G. Sankaran (2016). "Advances in understanding erythropoiesis: evolving perspectives." *Br J Haematol* 173(2): 206-218.

Pan, B. T. and R M. Johnstone (1983). "Fate of the transferrin receptor during maturation of sheep reticulocytes in vitro: selective externalization of the receptor." *Cell* 33(3): 967-978.

Schakel, K., M. von Kietzell, A. Hansel, A., Ebling, L. Schulze, M. Haase, C. Senamler, M. Sarfati, A. N. Barclay, G. J. Randolph, M. Meurer and E. P. Bieber (2006). "Human 6-sulfo LacNAc-expressing dendritic cells are principal producers of earls, interleukin-12 and are controlled by erythrocytes." *Immunity* 24(6): 767-777.

Taylor, W. J., Korendowych, P. Nash, P. S. Helliwell, E. Choy, G. C. Krueger, E. R. Soriano, N. J. McHugh and C. F. Rosen (2008). "Drug use and toxicity in psoriatic disease: focus on methotrexate." *J Rheumatol* 35(7): 1454-1457.

Testa, U. (2004). "Apoptotic mechanisms in the control of erythropoiesis." Leukemia 18(7): 1176-1199.

Van Putter, L. M. (1958). "The life span of red cells in the rat and the mouse as determined by labeling with DFP32 in vivo." *Blood* 13(8): 789-794.

Yi., T., J. Li, H. Chen, J. Wu, J. An, Y. Xu, Y. Hu, C. A. Lowell and J. G. Cyster (2015). "Splenic Dendritic Cells Survey Red Blood Cells for Missing Self-CD47 to Trigger Adaptive Immune Responses." *Immunity* 43(4): 764-775.

What is claimed is:

1. A method for treating Pompe disease in a subject in need of treatment with human acid α-glucosidase, comprising:
    (a) administering to the subject an effective amount of methotrexate;
    (b) administering to the subject an effective amount of human acid α-glucosidase;
    (c) detecting an erythropoiesis biomarker in a sample obtained from the subject between at least one day and about 30 days after administration of methotrexate, wherein the detecting the erythropoiesis biomarker is detecting the expression of a gene encoding transferrin receptor; and
    (d) continuing further treatment with human acid α-glucosidase with or without administering rituximab based on a level of the erythropoiesis biomarker compared to that of a control.

2. The method of claim 1, wherein a change in the level of the erythropoiesis biomarker is associated with induction of erythropoiesis.

3. The method of claim 2, wherein if the level of the erythropoiesis biomarker is approximately equal to or less than that of a control, step (d) comprises administering rituximib concurrently with further treatment with human acid α-glucosidase; or wherein if the level of the erythropoiesis biomarker is elevated with respect to that of a control, step (d) comprises continuing further treatment with human acid α-glucosidase without administering rituximib.

4. The method of claim 1, wherein the sample is a blood sample.

5. The method of claim 1, wherein the effective amount of methotrexate is administered in a single cycle or in three cycles.

6. The method of claim 1, wherein the sample is obtained from the subject at least about one day to about 30 days following the last administration of the methotrexate.

7. The method of claim 1, wherein the Pompe disease is infantile-onset Pompe disease.

8. The method of claim 1, wherein the subject is cross reactive immunological material (CRIM)-negative.

9. The method of claim 4, wherein the blood sample is a blood fraction comprising peripheral blood mononuclear cells (PBMC).

10. The method of claim 9, wherein the blood sample is a serum sample or a plasma sample.

11. The method of claim 1, wherein the control is a historical control or a placebo control.

12. The method of claim 5, wherein a cycle of methotrexate consists of 1 day of methotrexate administration or 2, 3, 4, 5, 6, 7, 8, 9, 10, or 11 consecutive days of methotrexate administration.

13. The method of claim 1, wherein the methotrexate is administered to the subject at a time selected from one or more of before, during, and after administration of human acid α-glucosidase.

14. The method of claim 13, wherein the methotrexate is administered between 48 hours prior to and 48 hours after administration of human acid α-glucosidase.

15. The method of claim 1, wherein the methotrexate is administered at about 0.1 mg/kg to about 5 mg/kg.

16. The method of claim 1, wherein the sample is obtained from the subject at about 7 days to about 14 days following the last administration of the methotrexate.

17. The method of claim 1, wherein samples are obtained on a plurality of days following the last administration of the methotrexate.

18. The method of claim 1, wherein a sample is obtained on one or more of day 1, day 2, day 3, day 4, day 5, day 6, day 7, day 14, day 21, or day 28 following the last administration of the methotrexate.

* * * * *

UNITED STATES PATENT AND TRADEMARK OFFICE
CERTIFICATE OF CORRECTION

PATENT NO. : 12,213,979 B2
APPLICATION NO. : 16/955391
DATED : February 4, 2025
INVENTOR(S) : Alexandra Joseph et al.

Page 1 of 1

It is certified that error appears in the above-identified patent and that said Letters Patent is hereby corrected as shown below:

In the Claims

At Column 74, Claim number 3, Line number 48, please replace "rituximib" with --rituximab--; and At Column 74, Claim number 3, Line number 52, please replace "without administering rituximib." with --without administering rituximab.--.

Signed and Sealed this
Tenth Day of June, 2025

Coke Morgan Stewart
*Acting Director of the United States Patent and Trademark Office*